(12) United States Patent
Capanema et al.

(10) Patent No.: US 10,385,140 B2
(45) Date of Patent: Aug. 20, 2019

(54) CELLULOSE-CONTAINING COMPOSITIONS AND METHODS OF MAKING SAME

(71) Applicant: RENMATIX, INC., King of Prussia, PA (US)

(72) Inventors: Ewellyn A. Capanema, Wayne, PA (US); Mikhail Y. Balakshin, Wayne, PA (US); Patrick David Fitzgibbon, Avondale, PA (US); Matyas Kosa, Vancouver (CA); Todd Michael McLarty, Acworth, GA (US); Charles Sebastian Sanderson, Wayne, PA (US)

(73) Assignee: Renmatix, Inc., King of Prussia, PA (US)

(*) Notice: Subject to any disclaimer, the term of this patent is extended or adjusted under 35 U.S.C. 154(b) by 63 days.

(21) Appl. No.: 15/511,183

(22) PCT Filed: Sep. 25, 2015

(86) PCT No.: PCT/US2015/052435
§ 371 (c)(1),
(2) Date: Mar. 14, 2017

(87) PCT Pub. No.: WO2016/049567
PCT Pub. Date: Mar. 31, 2016

(65) Prior Publication Data
US 2017/0275385 A1    Sep. 28, 2017

Related U.S. Application Data

(60) Provisional application No. 62/056,072, filed on Sep. 26, 2014.

(51) Int. Cl.
C08B 15/08 (2006.01)
C08B 15/00 (2006.01)
(Continued)

(52) U.S. Cl.
CPC .............. C08B 15/08 (2013.01); C07G 1/00 (2013.01); C08B 11/18 (2013.01); C08B 15/00 (2013.01);
(Continued)

(58) Field of Classification Search
None
See application file for complete search history.

(56) References Cited

U.S. PATENT DOCUMENTS 4,652,363 A    3/1987  Miller
4,946,953 A    8/1990  Okuma et al.
(Continued)

FOREIGN PATENT DOCUMENTS

AU    2015320328    9/2015
BR    1120170059975    9/2015
(Continued)

OTHER PUBLICATIONS

Sasaki et al, production of cellulose II from native cellulose by near and supercritical water solubilization, J. Agric. Food Chem., 51, 5376-5381 (Year: 2003).*
(Continued)

Primary Examiner — Melvin C. Mayes
Assistant Examiner — Stefanie J Cohen
(74) Attorney, Agent, or Firm — Ballard Spahr LLP

(57) ABSTRACT

Cellulose-containing compositions and method of making same are disclosed. The compositions comprise a cellulose product comprising a type-I cellulose, a type-II cellulose, amorphous cellulose, or a combination thereof. Further, methods are disclosed for making these compositions and for further hydrolyzing these compositions. Additionally, uses for the cellulose-containing compositions are disclosed.

20 Claims, 17 Drawing Sheets

(51) Int. Cl.
*C08L 1/02* (2006.01)
*C08B 37/00* (2006.01)
*C08H 7/00* (2011.01)
*C08L 97/00* (2006.01)
*C08B 15/02* (2006.01)
*C07G 1/00* (2011.01)
*C08B 11/18* (2006.01)
*C08B 15/06* (2006.01)
*C08L 97/02* (2006.01)
*C09J 101/02* (2006.01)
*C09J 161/06* (2006.01)
*C09J 175/04* (2006.01)
*C09J 11/06* (2006.01)
*C09J 201/00* (2006.01)
*G01N 23/20* (2018.01)

(52) U.S. Cl.
CPC .......... *C08B 15/02* (2013.01); *C08B 15/06* (2013.01); *C08B 37/0057* (2013.01); *C08H 6/00* (2013.01); *C08L 1/02* (2013.01); *C08L 97/005* (2013.01); *C08L 97/02* (2013.01); *C09J 101/02* (2013.01); *C09J 161/06* (2013.01); *C09J 175/04* (2013.01); *C09J 11/06* (2013.01); *C09J 201/00* (2013.01); *G01N 23/20* (2013.01)

(56) References Cited

U.S. PATENT DOCUMENTS

| | | | |
|---|---|---|---|
| 5,104,520 | A | 4/1992 | Maronde et al. |
| 6,921,820 | B2 | 7/2005 | Arai et al. |
| 8,729,325 | B2 | 5/2014 | Powell |
| 2003/0017187 | A1 | 1/2003 | Brode et al. |
| 2003/0018187 | A1 | 1/2003 | Arai et al. |
| 2004/0074615 | A1* | 4/2004 | Nguyen .............. C08B 1/00 162/9 |
| 2010/0048884 | A1 | 2/2010 | Kilambi |
| 2010/0285295 | A1* | 11/2010 | Wang .............. C09J 11/04 428/292.4 |
| 2011/0182990 | A1 | 7/2011 | Su et al. |
| 2012/0285445 | A1 | 11/2012 | Kilambi et al. |
| 2012/0291774 | A1 | 11/2012 | Kilambi et al. |
| 2013/0172546 | A1 | 7/2013 | Floyd et al. |
| 2013/0172547 | A1 | 7/2013 | Floyd et al. |
| 2013/0239954 | A1 | 9/2013 | Kilambi et al. |
| 2014/0014092 | A1 | 1/2014 | Kazachkin et al. |
| 2014/0039144 | A1 | 2/2014 | Simard et al. |
| 2014/0200335 | A1* | 7/2014 | Olkowski .............. D21C 3/04 530/500 |
| 2014/0275501 | A1 | 9/2014 | Capanema et al. |
| 2015/0176091 | A1 | 6/2015 | Kazachkin et al. |
| 2015/0191499 | A1 | 7/2015 | Floyd et al. |
| 2015/0191500 | A1 | 7/2015 | Floyd et al. |
| 2016/0108182 | A1 | 4/2016 | Kilambi et al. |
| 2016/0244852 | A1 | 8/2016 | Kilambi et al. |

FOREIGN PATENT DOCUMENTS

| | | |
|---|---|---|
| CA | 2962606 | 9/2015 |
| CA | 2962606 C | 1/2019 |
| CN | 101395320 A | 3/2009 |
| CN | 2015800518719 | 9/2015 |
| EP | 1547170 A4 | 6/2005 |
| EP | 15843632.9 | 9/2015 |
| GB | 1003537 A | 9/1965 |
| IN | 201737008305 | 9/2015 |
| JP | 2003-213037 A | 7/2003 |
| JP | 2008-248202 A | 10/2008 |
| NZ | 730223 | 9/2015 |
| SG | 11201701740 | 9/2015 |
| WO | WO-2011/091044 A1 | 7/2011 |
| WO | WO-2013/101397 A1 | 7/2013 |
| WO | WO-2013/101402 A1 | 7/2013 |
| WO | WO-2013/101403 A1 | 7/2013 |
| WO | WO-2013/165308 A1 | 11/2013 |
| WO | WO-2014/012030 A1 | 1/2014 |
| WO | WO-2014/144746 A1 | 9/2014 |
| WO | WO-2015/104459 A1 | 7/2015 |
| WO | PCT/US2015/052435 | 9/2015 |
| WO | WO-2016/049564 A1 | 3/2016 |
| WO | WO-2016/049567 A1 | 3/2016 |
| WO | WO-2016/049569 A1 | 3/2016 |
| ZA | 2017/02794 | 9/2015 |

OTHER PUBLICATIONS

Li et al, Preparation and characterization of cellulose nanofibers from partly mercerized cotton by mixed acid hydrolysis, Dec. 18, 2013, Cellulose, 21, pp. 301-309 (Year: 2013).*
Abdullah et al, hydrothermal decomposition of various crystalline celluloses as treated by semi-flow hot compressed water, Published online May 24, 2014, J. Wood Sci, 60, pp. 278-286 (Year: 2014).*
Ververis et al, Fiber dimensions, lignin and cellulose content of various plant materials and their suitability for paper productions, 2004, industrial crops and products, 19, pp. 245-254 (Year: 2004).*
Pilla et al, Handbook of bioplastics and biocomposites engineering applications, 2011, p. 465 (Year: 2011).*
Supplementary European Search Report and Written Opinion dated Mar. 27, 2018 by the European Patent Office for Patent Application No. 15843632.9, which was filed Sep. 25, 2015 and published as EP 3186286 on Jul. 5, 2017 (Inventor—Capanema et al.; Applicant—Renmatix, Inc.) (6 pages).
Avicel PH-200. FMC BioPolymer: Certificate of Analysis—Avicel® Microcrystalline Cellulose, NF, Ph. Eur, JP. FMC International (1 page).
Avicel® PH-200—Microcrystalline Cellulose NF, Ph. Eur., JP. Product Specification Bulletin. FMC International: FMC BioPolymer (2 pages).
Avicel® RC-591—Microcrystalline Cellulose and Carboxymethylcellulose Sodium, NF, BP. Pharmaceutical Emulsions and Suspensions: Stabilization Technology for Liquid and Semi-Solid Dosage Forms. FMC International: FMC BioPolymer (1994) (20 pages).
Beaumont, M. et al., A Nanostructured Cellulose II Gel Consisting of Spherical Particles. ACS Sustainable Chem Eng. 2016; pp. 1-26 (27 pages).
Benavides, E.E.U., Cellulose Nanocrystals Properties and Applications in Renewable Nanocomposites. Doctoral Thesis. Graduate School of Clemson University: Chemical Engineering (2011) (197 pages).
Buffiere, J., Cellulose Dissolution in Near- and Supercritical Water for Cello-Oligosaccharides Production. Master's Thesis. Aalto University School of Chemical Technology (2014) (95 pages).
DuPont, A.L., Cellulose in Lithium Chloride/N,N-dimethylacetamide, Optimization of a Dissolution Method Using Paper Substrates and Stability of the Solutions. Polymer. 2003; 44:4117-26.
El Seoud, O.A. et al., Chemistry and Applications of Polysaccharide Solutions in Strong Electrolytes/Dipolar Aprotic Solvents: An Overview. Molecules. 2013; 18:1270-313.
Habibi, Y. et al., Cellulose Nanocrystals: Chemistry, Self-Assembly, and Applications. Chem Rev. A-V (22 pages).
Hennings, U. et al., Dissolution Behavior of Different Celluloses. Biomacromolecules. 2011; 12:871-9.
Masuelli, Mark-Houwink Parameters for Aqueous-Soluble Polymers and Biopolymers at Various Temperatures. J Polymer Biopolymer Physics Chem. 2014; 2(2):37-43.
Matsunga, M. et al., Chemical Conversion of Wood by Treatment in a Semi-Batch Reactor with Subcritical Water. J Supercritical Fluids. 2008; 44:364-9.
Newman, R.H. and T.C. Davidson, Molecular Conformations at the Cellulose-Water Interface. Cellulose. 2004; 11:23-32.
Potthast, A. et al., A Novel Method for the Determination of Carbonyl Groups in Cellulosics by Fluoresence labeling. 3. Monitoring Oxidative Processes. Biomacromolecules. 2003; 4:743-9.

(56) References Cited

OTHER PUBLICATIONS

Potthast, A. et al., Comparison Testing of Methods for Gel Permeation Chromatography of Cellulose: Coming Closer to a Standard Protocol. Cellulose. 2015; 22(3):1591-613.
Reier, G.E., Avicel® PH Microcrystalline Cellulose, NF, Ph Eur., JP, BP. Section 11. FMC International (2000) (27 pages).
Röhrling et al., A Novel Method for the Determination of Carbonyl Groups in Cellulosics by Fluorescence Labeling. 1. Method Development. Biomacromolecules. 2002; 3:959-68.
Röhrling et al., A Novel Method for the Determination of Carbonyl Groups in Cellulosics by Fluorescence Labeling. 2. Validation and Application. Biomacromolecules. 2002; 3:969-75.
Sasaki, M. et al., Kinetics of Cellulose Conversion at 25 MPa in Sub- and Supercritical Water. Amer Inst Chem Eng. 2004; 50(1):192-202.
Sasaki, M. et al., Production of Cellulose II from Native Cellulose by Near- and Supercritical Water Solubilization. J Agric Food Chem. 2003; 51:5376-81.
Sasaki, M. et al., Rapid and Selective Conversion of Cellulose to Valuable Chemical Intermediates with Supercritical Water. Proc. 6th International Symposium on Supercritical Fluids. 2003; Tome 2:1417-22.
Segal, L. et al., An Empirical Method for Estimating the Degree of Crystallinity of Native Cellulose Using the X-Ray Diffractometer. Tex Res J. 1959; 29(10):786-94 (Abstract; 2 pages).
Terinte, N. et al., Overview on Native Cellulose and Microcrystalline Cellulose I Structure Studied by X-Ray Diffraction (WAXD): Comparison Between Measurement Techniques. Lenzinger Berichte. 2011; 89:118-31.
Tolonen, L.K. et al., Supercritical Water Treatment for Cello-Oligosaccharide Production from Microcrystalline Cellulose. Carbohydr Res. 2015; 401:16-23.
Yu, Y. and H. Wu, Characteristics and Precipitation of Glucose Oligomers in the Fresh Liquid Products Obtained from the Hydrolysis of Cellulose in Hot-Compressed Water. Ind Eng Chem Res. 2009; 48:10682-90.
Yu, Y., Formation and Characteristics of Glucose Oligomers During the Hydrolysis of Cellulose in Hot-Compressed Water. Doctoral Thesis. Curtin University of Technology: Dept Chem Eng (2009) (192 pages).
Zuckerstatter, G. et al., The Elucidation of Cellulose Supramolecular Structure by $_{13}$C CP-MAS NMR. Lenzinger Berichte. 2009; 87:38-46.
International Search Report and Written Opinion dated Jan. 26, 2016 by the International Searching Authority for Patent Application No. PCT/US2015/052435, which was filed Sep. 25, 2015 and published as WO 2016/049567 on Mar. 31, 2016 (Inventor—Capanema et al.; Applicant—Renmatix, Inc.) (8 pages).
International Preliminary Report on Patentability dated Mar. 28, 2017 by the International Searching Authority for Patent Application No. PCT/US2015/052435, which was filed on Sep. 25, 2015 and published as WO 2016/049567 on Mar. 31, 2016 (Inventor—Capanema et al.; Applicant—Renmatix, Inc.) (6 pages).
U.S. Appl. No. 62/056,072, filed Sep. 26, 2014, Capanema (Renmatix, Inc.).
Abdullah R., "Hydrothermal decomposition of various crystalline celluloses as treated by semi-flow hot-compressed Water", Journal of Wood Science, vol. 60, pp. 278-286.
Li, Y., "Preparation and characterization of cellulose nanofibers from partly mercerized cotton by mixed acid hydrolysis", Cellulose, vol. 21 pp. 301-309.
Examination Report was issued on Feb. 20, 2019 by Australian Patent Office for AU Application No. 2015320328, which was filed on Sep. 25, 2015 and published as AU 2015320328 A1 on Apr. 27, 2017(Applicant- Renmatix, Inc.) (6 pages).
Office Action was issued on Mar. 4, 2019 by SIPO for CN Application No. 201580051871.9, which was filed on Sep. 25, 2015 and published as CN107074981A on Aug. 18, 2017 (Applicant—Renmatix, Inc.) (Original— 12 pages).

\* cited by examiner

CELLULOSE-CONTAINING COMPOSITIONS AND METHODS OF MAKING SAME

CROSS-REFERENCE TO RELATED APPLICATIONS

This application is a U.S. National Phase Application of International Application No. PCT/US2015/052435, filed Sep. 25, 2015, which claims the benefit of U.S. Application No. 62/056,072 filed Sep. 26, 2014, the entire disclosures of which are incorporated herein by reference in their entirety.

FIELD OF THE INVENTION

Described herein are cellulose-containing compositions and methods of making same. More particularly, compositions comprising a type-I cellulose, a type-II cellulose, or a combination thereof are described herein. Furthermore, methods of making and using these compositions are described herein. The compositions disclosed herein can be utilized, for example, for pharmaceutical, cosmetic, and/or industrial applications, and the methods disclosed herein can be utilized, for example, to form a type-I and/or type-II cellulose, shorter chain glucose oligomers, glucose monomer, and/or purified lignin.

BACKGROUND OF THE INVENTION

Cellulose materials merit special consideration in the current global concern over the environment and raw materials, because they are renewable, biodegradable, and are the world's most abundant natural polymer. It has been estimated that between about $10^{10}$ to about $10^{11}$ tons of cellulose are consumed globally each year in industrial applications for making textiles, paper products, plastics, food and pharmaceuticals additives, cosmetic additives, propellants, and as an affordable renewable energy source.

Lignocellulosic biomass typically contains cellulose, hemicellulose, lignin, and minerals, and in some instances minor amounts of proteins and lipids (fats, waxes, and oils). About two thirds of the dry mass of cellulosic materials is present as cellulose and hemicellulose with lignin making up the bulk of the remaining dry mass. There are a number of processes for converting lignocellulosic biomass into liquid streams of various sugars, extracting lignin, and/or recovering unreacted cellulose, such as in the pulp and paper industry. Many of these processes are complicated, capital intensive, time consuming, and require the use of harsh toxic chemicals. Therefore, there is a need for compositions containing cellulose, methods for preparing them, and methods for using them. The invention is directed to these, as well as other, important ends.

SUMMARY OF THE INVENTION

In one embodiment, the invention relates to a composition comprising, consisting of, or consisting essentially of a cellulose product in an amount about 45% by weight to about 100% by weight, based on the total weight of the composition on a dry basis, wherein the cellulose product comprises a type-I cellulose and a type-II cellulose, wherein the cellulose product comprises cellulose having a weight-average molecular weight of about 3,000 g/mol to about 25,000 g/mol as determined on a sample of the cellulose product that has been prepared for gel-permeation chromatography analysis according to a first condition, and wherein cellulose in the cellulose product has a carbonyl content of at least about 60 µmol/g, as determined on a sample of the cellulose product that has been prepared for gel-permeation chromatography analysis according to a second condition.

In another embodiment, about 100% by weight, based on the total weight of the cellulose product on a dry basis, of the cellulose product is cellulose having a weight-average molecular weight of about 3,000 g/mol to about 25,000 g/mol as determined on a sample of the cellulose product that has been prepared for gel-permeation chromatography analysis according to a first condition. In a further embodiment, at least about 80% by weight, based on the total weight of the cellulose product on a dry basis, of the cellulose product is cellulose having a weight-average molecular weight of about 5,000 g/mol to about 18,000 g/mol as determined on a sample of the cellulose product that has been prepared for gel-permeation chromatography analysis according to a first condition. In a yet further embodiment, at least about 80% by weight, based on the total weight of the cellulose product on a dry basis, of the cellulose product is cellulose having a weight-average molecular weight of about 3,000 g/mol to about 12,000 g/mol as determined on a sample of the cellulose product that has been prepared for gel-permeation chromatography analysis according to a first condition.

In a further embodiment, the composition comprises an alcohol-soluble fraction. The alcohol-soluble fraction can comprise lignin in some embodiments. In yet another embodiment, the composition comprises a water-soluble fraction comprising at least one cello-oligosaccharide.

In some embodiments, the composition further comprises at least one pharmaceutically-active ingredient.

In some embodiments, the cellulose product can be used in adhesives, e.g., adhesive resins such as phenolic resins and phenol-formaldehyde resins.

In some embodiments, a method is disclosed for preparing glucose and glucose oligomers from a feedstock comprising type-I cellulose. In some embodiments, the invention is directed to a method comprising, consisting of, or consisting essentially of: providing a feedstock comprising a type-I cellulose; converting at least portion of the type-I cellulose to a type-II cellulose; and hydrolyzing at least a portion of the type-II cellulose. In some embodiments, the invention is directed to a method comprising, consisting of, or consisting essentially of: providing a feedstock comprising a type-I cellulose; converting at least portion of the type-I cellulose to a type-II cellulose; and hydrolyzing in a different step at least a portion of the unconverted type-I cellulose at the same or different conditions than the converting (e.g., at lower temperature, lower pressure, acidic conditions, enzymatic conditions, or any combination thereof). In certain embodiments, the feedstock is selected from the group consisting of lignocellulosic biomass, cellulosic biomass, processed cellulosic biomass, municipal solid waste, fractionated biomass, unfractionated biomass, and any combination thereof. In yet other embodiments, the converting comprises contacting the feedstock with a fluid. In certain embodiments, the fluid comprises water, wherein the water is hot compressed water or supercritical water.

In further embodiments, the invention is directed to a method comprising, consisting of, or consisting essentially of: providing a reactant comprising a material selected from the group consisting of lignocellulosic biomass, cellulosic biomass, processed cellulosic biomass, municipal waste, and a combination thereof; contacting the reactant with a fluid comprising water, wherein the water is sub-critical, near-critical, or supercritical water, to form a first reactant mixture, wherein the first reactant mixture is at a fifth temperature and at a fifth pressure, and maintaining the first reactant mixture at the fifth temperature, and the fifth pressure for a fifth period of time; quenching the first reactant mixture to form a first product mixture comprising: i) a first liquid fraction; and ii) a first solid fraction; wherein the first solid fraction comprises a composition comprising a cellulose product; and processing the first product mixture; wherein the processing is at least one of: a) recovering at least a portion of the cellulose product from the first product mixture to form a recovered cellulose product, wherein a yield of the recovered cellulose product is from about 5% to about 100%, based on the amount of cellulose in the reactant; and b) hydrolyzing at least a portion of the first product mixture. As one of ordinary skill in the art would readily appreciate, in certain embodiments, the contacting may cause at least a portion of the reactant to hydrolyze.

In some embodiments, at least one of conditions (1)-(4) is satisfied: (1) the cellulose product comprises a type-I cellulose and type-II cellulose; (2) the cellulose product comprises type-II cellulose and does not comprise type-I cellulose, (3) the cellulose product has a weight-average molecular weight of about 3,000 g/mol to about 25,000 g/mol as determined on a sample of the cellulose product that has been prepared for gel-permeation chromatography analysis according to a first condition; and (4) cellulose in the cellulose product has a carbonyl content of at least about 60 µmol/g, as determined on a sample of the cellulose product that has been prepared for gel-permeation chromatography analysis according to a second condition.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention. In the drawings.

DETAILED DESCRIPTION OF THE INVENTION

Figure 1:
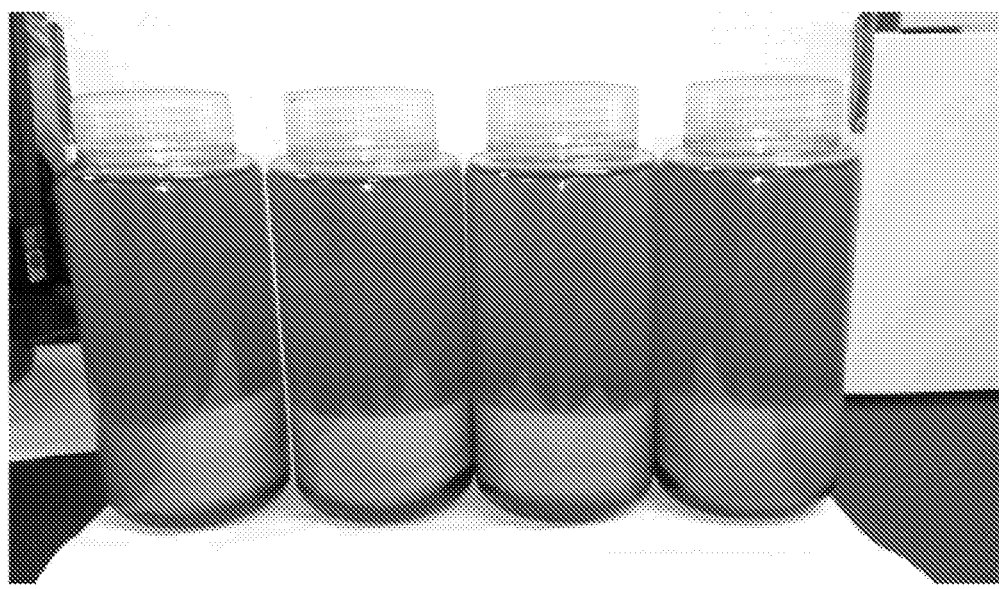
FIG. 1 shows a slurry that has been centrifuged after being subjected to supercritical hydrolysis.

The present invention can be understood more readily by reference to the following detailed description, examples, drawings, and claims, and their previous and following description. However, it is to be understood that this invention is not limited to the specific compositions, articles, devices, systems, and/or methods disclosed unless otherwise specified, and as such, of course, can vary. While aspects of the present invention can be described and claimed in a particular statutory class, such as the system statutory class, this is for convenience only and one of skill in the art will understand that each aspect of the present invention can be described and claimed in any statutory class.

The following description of the invention is also provided as an enabling teaching of the invention in its best, currently known aspect. To this end, those of ordinary skill in the relevant art will recognize and appreciate that changes and modifications may be made to the various aspects of the invention described herein, while still obtaining the beneficial results of the present invention. It will also be apparent that some of the benefits of the present invention may be obtained by selecting some of the features of the present invention without utilizing other features. Accordingly, those of ordinary skill in the relevant art will recognize that many modifications and adaptations to the present invention are possible and may even be desirable in certain circumstances, and are thus also a part of the present invention.

While the present invention is capable of being embodied in various forms, the description below of several embodiments is made with the understanding that the present disclosure is to be considered as an exemplification of the invention, and is not intended to limit the invention to the specific embodiments illustrated. Headings are provided for convenience only and are not to be construed to limit the invention in any manner. Embodiments illustrated under any heading or in any portion of the disclosure may be combined with embodiments illustrated under any other heading or other portion of the disclosure.

Any combination of the elements described herein in all possible variations thereof is encompassed by the invention unless otherwise indicated herein or otherwise clearly contradicted by context.

Unless otherwise expressly stated, it is in no way intended that any method or aspect set forth herein be construed as requiring that its steps be performed in a specific order. Accordingly, where a method claim does not specifically state in the claims or description that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of embodiments described in the specification. It is to be understood that both the foregoing general description and the following detailed description are exemplary and explanatory only and are not restrictive.

All publications mentioned herein are incorporated herein by reference to disclose and describe the methods and/or materials in connection with which the publications are cited.

It is to be understood that the terminology used herein is for the purpose of describing particular aspects only and is not intended to be limiting. Unless defined otherwise, all technical and scientific terms used herein have the same meaning as commonly understood by one of ordinary skill in the art to which this invention belongs. In this specification and in the claims which follow, reference will be made to a number of terms which are defined herein.

As used in the specification and the appended claims, the singular forms "a," "an" and "the" include plural referents unless the context clearly dictates otherwise.

As used herein, the terms "optional" or "optionally" mean that the subsequently described event, condition, component, or circumstance may or may not occur, and that the description includes instances where said event, condition, component, or circumstance occurs and instances where it does not.

As used herein, the phrase "sufficient to" (e.g., "conditions sufficient to") refers to such a value or a condition that is capable of performing the function or property for which a sufficient value or condition is expressed. As will be pointed out below, the exact value or particular condition required may vary from one embodiment to another, depending on recognized variables, such as the materials employed and/or the processing conditions.

The term "by weight," when used in conjunction with a component, unless specifically stated to the contrary, is based on the total weight of the formulation or composition in which the component is included. For example, if a particular element or component in a composition or article is said to have 8% by weight, it is understood that this percentage is in relation to a total compositional percentage of 100%. In some instances, the weight percent of a component is based on the total weight of the composition "on a dry basis," which indicates the weight of the composition without water (e.g., less than about 1%, less than about 0.5%, less than about 0.1%, less than about 0.05%, or about 0% of water by weight, based on the total weight of the composition).

When disclosing numerical values herein, for example, 1, 2, 3, 4, 5, 6, 7, 8, 9, 10, the following sentence typically follows such numerical values: "Each of the foregoing numbers can be preceded by the term 'about,' 'at least about,' or 'less than about,' and any of the foregoing numbers can be used singly to describe an open-ended range or in combination to describe a close-ended range." This sentence means that each of the aforementioned numbers can be used alone (e.g., 4), can be prefaced with the word "about" (e.g., about 8), prefaced with the phrase "at least about" (e.g., at least about 2), prefaced with the phrase "less than about" (e.g., less than about 7), or used in any combination with or without any of the prefatory words or phrases to define a range (e.g., 2 to 9, about 1 to 4, 8 to about 9, about 1 to about 10, and so on). Moreover, when a range is described as "about X or less," this phrase is the same as a range that is a combination of "about X" and "less than about X" in the alternative. For example, "about 10 or less" is the same as "about 10, or less than about 10." Such interchangeable range descriptions are contemplated herein. Other range formats are disclosed herein, but the difference in formats should not be construed to imply that there is a difference in substance.

As used herein, the term "biomass" means a renewable energy source generally comprising carbon-based biological material derived from living or recently-living organisms. In some embodiments, the biomass may serve as a feedstock and, as such, the terms may be used interchangeably. Suitable feedstocks include lignocellulosic feedstock, cellulosic feedstock, hemicellulosic feedstock, starch-containing feedstocks, and the like. The lignocellulosic feedstock may be from any lignocellulosic biomass, such as plants (e.g., duckweed, annual fibers, etc.), trees (softwood, e.g., fir, pine, spruce, etc.; tropical wood, e.g., balsa, iroko, teak, etc.; or hardwood, e.g., elm, oak, aspen, pine, poplar, willow, eucalyptus, etc.), bushes, grass (e.g., miscanthus, switchgrass, rye, reed canary grass, giant reed, or sorghum), dedicated energy crops, municipal waste (e.g., municipal solid waste), and/or a by-product of an agricultural product (e.g., corn, sugarcane, sugar beets, pearl millet, grapes, rice, straw). The biomass may be from a virgin source (e.g., a forest, woodland, or farm) and/or a by-product of a processed source (e.g., off-cuts, bark, and/or sawdust from a paper mill or saw mill, sugarcane bagasse, corn stover, palm oil industry residues, branches, leaves, roots, and/or hemp). Suitable feedstocks may also include the constituent parts of any of the aforementioned feedstocks, including, without limitation, lignin, C6 saccharides (including cellulose, C6 oligosaccharides, and C6 monosaccharides), C5 saccharides (including hemicellulose, C5 oligosaccharides, and C5 monosaccharides), and mixtures thereof. Suitable feedstocks can also include fractionated biomass, in which at least a portion of the original components has been removed (e.g., fractionated biomass in which at least a portion, some, most, or all of originally present hemicellulose has been removed, e.g., 30, 35, 40, 45, 50, 55, 60, 65, 70, 75, 80, 85, 90, 95, or 99 wt. % of the hemicellulose originally present has been removed (each of the foregoing numbers can be preceded by the word "about," "at least about," or "less than about," and any of the foregoing numbers can be used singly to describe an open-ended range or in combination to describe a close-ended range)). Suitable feedstocks can also include unfractionated biomass, in which the at least a portion, some, most, or all of the hemicellulose present in the biomass has not been removed.

As used herein, "dry biomass" (or equivalently "bone dry biomass") refers to biomass substantially without any water (i.e., about 0% moisture content), or with only residual water remaining (i.e. no more than about 1%, no more than about 0.5%, no more than about 0.1%, no more than about 0.05%, or no more than about 0.01% moisture content). When referring to dry biomass, the biomass itself is not necessarily in a bone dry state, but rather the weight of the dry biomass is expressed as if all or substantially all of the water has been removed.

As used herein, "oligosaccharide" refers to linear or branched carbohydrate molecules of the same or different monosaccharide units joined together by glycosidic bonds having the general formula of $C_x(H_2O)_y$. Oligosaccharides may be thought of as shorter chain polysaccharides, i.e., polysaccharides simply having less monomeric residues in the polymeric chain. When an oligosaccharide contains $C_6$ monosaccharide residues, the general formula may be represented as $(C_6H_{10}O_5)_n$, where n is about 2 to about 9 (i.e., the number of hexose monomers in the oligosaccharide). As used herein, an oligomer (e.g., cello-oligosaccharide) has a DP of 2 to about 9, whereas a polymer (e.g., cellulose) has a DP of at least about 10.

As used herein, "monosaccharide" refers to any of the class of sugars that cannot be hydrolyzed to give a simpler sugar. Monosaccharides typically are $C_5$ (e.g., xylose) and $C_6$ sugars (e.g., glucose), but may also include monosaccharides having other numbers of carbon, such as $C_3$, $C_4$, $C_7$, $C_8$, and so on. Expressed another way, monosaccharides are the simplest building blocks of oligosaccharides and polysaccharides.

As used herein, "continuous" indicates a process that is uninterrupted for its duration, or interrupted, paused, or suspended only momentarily relative to the duration of the process. Treatment of biomass is "continuous" when biomass is fed into an apparatus without interruption or without a substantial interruption, or processing of said biomass is not done in a batch process.

As used herein, the terms "microcrystalline cellulose" and "MCC" are used interchangeably and refer to purified, partially depolymerized cellulose prepared by hydrolysis of cellulose fibers. Cellulose fiber typically comprises cellulose microfibers comprising amorphous, paracrystalline, and crystalline regions. The hydrolysis process largely removes the amorphous fraction, destroying the fiber-like morphology of the cellulose and forming the cellulose microcrystals containing wholly or mostly crystalline regions. In some embodiments, the microcrystalline cellulose may be characterized by substantially low content of inorganic impurities. Commercially available MCC includes, but is not limited to, AVICEL® products available from FMC BioPolymer.

As used herein, the term "nanocellulose" refers to a cellulosic material having at least one dimension in the nanometer range. The nanocellulose may comprise cellulose fibrils having a high aspect ratio. The nanocellulose may exhibit pseudo-plastic characteristics when incorporated into a fluid. A fluid containing nanocellulose can exhibit properties of certain gels or fluids that are viscous under normal conditions and develop a high storage modulus on standing. The nanocellulose fibrils may exhibit sufficiently high surface area and bonding ability.

As used herein, the term "substantially free of" refers to a composition having less than about 1% by weight, e.g., less than about 0.5% by weight, less than about 0.1% by weight, less than about 0.05% by weight, or less than about 0.01% by weight of the stated material, based on the total weight of the composition.

As used herein, the term "substantially," when used in reference to a composition, refers to at least about 60% by weight, e.g., at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or about 100% by weight, based on the total weight of the composition, of a specified feature or component.

All molecular weights and other values associated with molecular weights (e.g., polydispersity index, etc.) disclosed herein are measured by GPC after preparing the sample for measurement using the "first condition," as described elsewhere herein, unless specifically indicated otherwise or contradicted by context. When employing the first condition to prepare samples for GPC measurement, prior to the first condition the sample is first subjected to at least one gravity separation (one or more of centrifugation, hydrocyclone, etc.) to obtain a fractionated cellulosic portion that is enriched in cellulose compared to the sample prior to using the gravity separation. Gravity separation, as used herein, does not include mere settling using natural gravity, but rather is an induced gravity separation (e.g., centrifugation, hydrocyclone, etc.).

A supercritical fluid is a fluid at a temperature above its critical temperature and at a pressure above its critical pressure. A supercritical fluid exists at or above its "critical point," the point of highest temperature and pressure at which the liquid and vapor (gas) phases can exist in equilibrium with one another. At or above critical pressure and critical temperature, the distinction between liquid and gas phases disappears. A supercritical fluid possesses approximately the penetration properties of a gas simultaneously with the solvent properties of a liquid. Accordingly, supercritical fluid extraction has the benefit of high penetrability and good solvation.

Reported critical temperatures and pressures include: for pure water, a critical temperature of about 374.2° C., and a critical pressure of about 221 bar; for carbon dioxide, a critical temperature of about 31° C. and a critical pressure of about 72.9 atmospheres (about 1072 psig). Near-critical water has a temperature at or above about 300° C. and below the critical temperature of water (374.2° C.), and a pressure high enough to ensure that all fluid is in the liquid phase. Sub-critical water has a temperature of less than about 300° C. and a pressure high enough to ensure that all fluid is in the liquid phase. Sub-critical water temperature may be greater than about 250° C. and less than about 300° C., and in many instances sub-critical water has a temperature between about 250° C. and about 280° C. The term "hot compressed water" is defined herein as near-critical or sub-critical water, or at any temperature at least about 50° C. (preferably, at least about 100° C., at least about 150° C., at least about 200° C., at least about 250° C., at least about 300° C., or at least about 350° C.) but less than supercritical (e.g., less than about 374° C.), and at pressures such that the water (e.g., all of the water) is in a liquid state.

As used herein, a fluid which is "supercritical" (e.g., supercritical water, supercritical $CO_2$, etc.) indicates a fluid which would be supercritical if present in pure form under a given set of temperature and pressure conditions. For example, "supercritical water" indicates water present at a temperature of at least about 374.2° C. and a pressure of at least about 221 bar, whether the water is pure water, or present as a mixture (e.g., water and ethanol, water and $CO_2$, etc.). Thus, for example, "a mixture of sub-critical water and supercritical carbon dioxide" indicates a mixture of water and carbon dioxide at a temperature and pressure above that of the critical point for carbon dioxide but below the critical point for water, regardless of whether any supercritical phase contains water and regardless of whether the water phase contains any carbon dioxide. For example, a mixture of sub-critical water and supercritical $CO_2$ may have a temperature of about 250° C. to about 280° C. and a pressure of at least about 225 bar.

As used herein, the terms "molar mass distribution," "MMD," and "molecular weight distribution" are used interchangeably and describe the relationship between the number of moles of each polymer species or a number of polymer chains ($N_i$), and the molar mass ($M_i$) of that species or polymer chain. The molar mass distribution of a polymer may be modified by polymer fractionation. Different average values may be defined depending on the statistical method that is applied and are described herein.

As used herein, the term "number average molecular weight" ($M_n$, or $\overline{M}_n$) refers to the statistical average molecular weight of all the polymer chains in the sample and is defined by the formula:

$$M_n = \frac{\sum N_i M_i}{\sum N_i},$$

where $M_i$ is the molecular weight of a chain and $N_i$ is the number of chains of that molecular weight. $M_n$ may be determined for polymers, e.g., polycarbonate polymers, by methods well known to a person having ordinary skill in the art using molecular weight standards, e.g., polycarbonate standards or polystyrene standards, preferably certified or traceable molecular weight standards.

As used herein, the term "weight-average molecular weight" (Mw, or $\overline{M}$w) is defined by the formula:

$$M_w = \frac{\sum N_i M_i^2}{\sum N_i M_i},$$

where $M_i$ is the molecular weight of a chain and $N_i$ is the number of chains of that molecular weight. Compared to $M_n$, $M_w$ takes into account the molecular weight of a given chain in determining contributions to the molecular weight-average. Thus, the greater the molecular weight of a given chain, the more the chain contributes to the $M_w$. $M_w$ may be determined for polymers, e.g., polycarbonate polymers, by methods well known to a person having ordinary skill in the art using molecular weight standards, e.g., polycarbonate standards, polystyrene, or poly(methyl methacrylate) standards, preferably certified or traceable molecular weight standards.

As used herein, the term "viscosity average molar mass" (Mv, or $\overline{M}$v) is defined by the formula:

$$M_v = \left[\frac{\sum M_i^{1+a} N_i}{\sum M_i N_i}\right]$$

wherein $M_i$ is the molecular weight of a chain, $N_i$ is the number of chains of that molecular weight, and a is the Mark-Houwink-Sakurada coefficient. In one embodiment, when a is equal to 1 (as observed for certain inherently stiff or highly extended chains), then $M_v = M_w$. The viscosity average molar weight $M_v$ depends upon the complete molar weight distribution of a resin. For a normally distributed resin $M_v$ falls between the number- and weight-average molar weights. It may be precisely measured from the viscosities of a series of very dilute polymer solutions. More commonly, it is estimated from molar mass weight distributions obtained from size exclusion chromatography.

As used herein, the term "Z average molar mass" ($M_z$, or $\overline{M}_z$) is defined by the formula:

$$M_z = \frac{\sum M_i^3 N_i}{\sum M_i^2 N_i}$$

wherein $M_i$ is the molecular weight of a chain, and $N_i$ is the number of chains of that molecular weight. $M_z$ may be determined by ultracentrifugation techniques, static laser light scattering, or size exclusion chromatography.

As used herein, the term "peak molar mass" ($M_p$, or $\overline{M}_p$) is defined as a molecular weight of the highest peak in size exclusion chromatography. $M_p$ is quoted for very narrowly distributed polymers, such as polymer standards used in calibrations.

As used herein, the term "polydispersity index" (PDI) is defined by the formula:

$$PDI = \frac{M_w}{M_n}.$$

The PDI has a value equal to or greater than 1. As the polymer chains approach uniform chain length, the PDI approaches unity.

As used herein, the term "degree of polymerization" (DP) is defined as the number of monomeric units in a macromolecule or polymer or oligomer. For example and without limitation, the number-average degree of polymerization is given by:

$$DP_n = X_n = \frac{M_n}{M_0}$$

where $M_n$ is the number-average molecular weight and $M_0$ is the molecular weight of the monomer unit.

As used herein, the term "degradation products" includes, without limitation, furfural, hydroxylmethyl furfural (HMF), glycolaldehyde, glyceraldehydes, formic acid, levulinic acid, lactic acid, pyrubaldehyde, dihydroxyacetone, formalfdehyde, glucorinic acid, furan, or any combinations thereof.

As used herein, the term "lignin" refers to a phenolic based constituent of the cell walls of the plant. Depending on the species, lignin may be synthesized using up to three different phenyl propane monomers in a bionsynthetic pathway: coniferyl alcohol, syringyl alcohol, and coumaryl alcohol units:

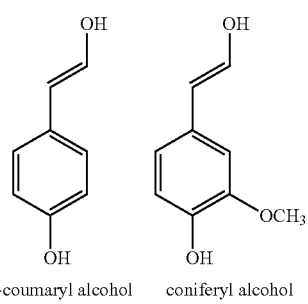

p-coumaryl alcohol   coniferyl alcohol

-continued

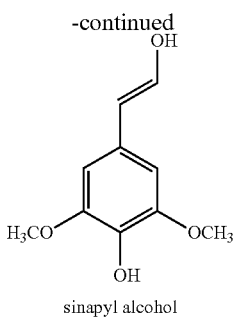

sinapyl alcohol

The lignin structure may comprise a number of possible bonding patterns between individual units.

As used herein, the term "unconverted type-I cellulose" refers to a type-I cellulose that that has not been converted to a type-II cellulose when a feedstock as defined herein is contacted with a fluid comprising water, wherein the water is subcritical, near-critical, or supercritical.

As used herein, the term "inorganic solvent" refers to a solvent that does not contain carbon, except for the exceptions noted below. In one embodiment, an inorganic solvent may comprise or consist of water. In another embodiment, an inorganic solvent may comprise nonaqueous solvents. For example and without limitation, an inorganic nonaqueous solvent can include ammonia, sulfur dioxide, sulfuryl chloride, sulfuryl chloride fluoride, phosphoryl chloride, dinitrogen tetroxide, antimony trichloride, bromine pentafluoride, sulfuric acid, nitric acid, phosphorous tribromide, hydrogen fluoride, supercritical carbon dioxide, carbon dioxide, carbon disulfide, various molten salts, and the like. While supercritical carbon dioxide, carbon dioxide, carbon disulfide contain carbon, for the purposes of the disclosure they are considered inorganic solvents.

As used herein, the term "insoluble species" refers to any species present in a composition that cannot be dissolved in a reference solvent, or that precipitates when immersed into the reference solvent. The reference solvent can include, but is not limited to, an organic solvent, inorganic solvent, aqueous solution, water, inorganic acid, inorganic base, organic acid, organic base, polar solvent, non-polar solvent, protic solvent, aprotic solvent, ionic liquids, and the like. In certain embodiments, the species described herein cannot be dissolved when immersed into a solvent under certain special conditions, wherein the special conditions include, but are not limited to, increase in a temperature, decrease in a temperature, increase in a pressure, decrease in a pressure, mechanical mixing, ultrasound assisted mixing, and the like. For example and without limitation, the insoluble species comprise species that do not dissolve in water (where water is the reference solvent), methanol (where methanol is the reference solvent), a solution of 8% by weight LiCl in N,N-Dimethylacetamide (DMAc) (where the solution of 8% by weight of LiCl in DMAc is the reference solvent), dioxane (when dioxane is the reference solvent), and/or a mixture of dioxane and water (when mixture of dioxane and water is the reference solvent). Typically, the solubility is determined at ambient conditions (i.e., room temperature and at 1 atm).

As used herein, Size-Exclusion Chromatography (SEC) and Gel Permeation Chromatography (GPC) are used interchangeably herein and refer to chromatographic separation methods in which molecules in solution are separated by their size. The separation is achieved by the differential exclusion of the sample molecules as they pass through a bed of porous particles, known as a separation column. SEC may be used to determine a substantially accurate molar mass distribution of polymer molecules. For example, the liquid fraction (an eluent) passing though the column is collected in constant volumes. As the polymer elutes through the column, molecules that are too large to penetrate the column pores are excluded from the packing pore volume and elute at earlier retention times, whereas the smaller molecules penetrate into the column pores and elute at a later time. The concentration of eluted polymers may be measured by spectroscopic techniques, such as, for example, refractive index (RI) and ultraviolet (UV). The eluent flow may also be analyzed continuously with RI, Low-Angle Laser Light Scattering (LALLS), Multi-Angle Laser Light Scattering (MALLS), UV, and/or viscosity measurements. Typically, the GPC/SEC information reported herein is measured for the entire peak or peaks pertaining to an eluted compound, even if such compound is in the form of a multiplet (e.g., doublet). However, in some instances, it may make more sense to employ only the "main" peak and not the "tail" when analyzing a GPC trace to give more accurate results. As such, the parameters reported herein for GPC/SEC, e.g., degree of polymerization (DP), molecular weight (e.g., $M_w$, $M_n$, etc.), etc., may pertain to the entire peak or peaks for the compound, or may only pertain to the main peak, as will be clear from context.

Any property disclosed herein for any material or compound (e.g., cellulose product), for example, degree of polymerization (DP), molecular weight (e.g., $M_w$, $M_n$, etc.), polydispersity index, Mark-Houwink constants (a and K), carbonyl group content, etc., may apply to materials derived from comminuted biomass, digested steam exploded biomass, or both, as will be clear from context.

As used herein, the term "quenching" refers to a process causing a change in condition that, for example, causes a quick decrease in reaction rate (e.g., hydrolysis rate), such as by rapid temperature decrease, rapid pressure decrease, or rapid decrease in both temperature and pressure.

All pressures disclosed herein are gauge pressures, unless clearly contradicted by context.

As used herein, the term "excipient" refers to any constituent of a medicinal product other than the active substance and packaging material. In one embodiment, the excipient may represent an inactive substance formulated alongside an "active pharmaceutical ingredient" (API) of a pharmaceutical formulation. In another embodiment, the excipient can serve various therapeutic-enhancing purposes, such as and without limitation, facilitating drug absorption or solubility, or other pharmacokinetic considerations. In a further embodiment, excipients can also be used to improve powder flowability during a tablet formation, and to help prevent denaturation of the API over the expected shelf life. As one of ordinary skill in the art would readily appreciate, the selection of excipients may depend on various factors, including, for example and without limitation, the specific API, the specific application, the medicinal product administration route, and/or the dosage.

As used herein, the term "self-assembled" refers to a process in which existing system components spontaneously assemble via local interactions to form a specific structure, pattern, or a larger functional unit. Typically self-assembly takes place without external direction.

As used herein, the term "loss on drying" (LOD) refers to a method designed to measure the amount of water and/or volatile matter in a sample, when the sample is dried under specified conditions. LOD techniques are well-known in the art.

As used herein, the term "dried particles" refers to particles that have been substantially dried by any suitable drying method known to one of ordinary skill in the art, and dried particles typically contain less than about 1% by weight, e.g., less than about 0.5% by weight, less than about 0.1% by weight, less than about 0.05% by weight, or less than about 0.01% by weight of moisture, based on the total weight of the composition. As used herein, simply separating solids and liquids, e.g., by filtration or other such techniques, sometimes called "dewatering" in the art, does not result in "dried particles," as defined herein.

As used herein, the term "undried particles" refers to particles that have not been dried by a suitable technique. Undried particles contain more than about 1% by weight, e.g., more than about 5% by weight, more than about 25% by weight, more than about 50% by weight, or more than about 100% by weight of moisture, or are present as a suspension in any liquid media.

As used herein, the term "spheronizing agent" refers to a material used to facilitate production of spheroids of uniform size and sphericity.

As used herein, the term "compressibility" refers to a defined compression force required to achieve a given hardness of a tablet, for example.

As used herein, the term "carrying capacity" refers to the performance of a substance, typically an excipient, in allowing a composition to be formed into a tablet having satisfactory hardness and/or friability. As one of ordinary skill in the art would readily appreciate, the more drug substance that may be added to the excipient, or alternatively, the less excipient that is needed, the better the carrying capacity of the excipient. The cellulose product can be employed in a pharmaceutical formulation and formed into a tablet exhibiting suitable hardness and/or friability.

The use of numerical values in the various quantitative values specified in this application, unless expressly indicated otherwise, are stated as approximations as though the minimum and maximum values within the stated ranges were both preceded by the word "about." In this manner, slight variations from a stated value may be used to achieve substantially the same results as the stated value. Also, the disclosure of ranges is intended as a continuous range including every value between the minimum and maximum values recited as well as any ranges that may be formed by such values. Also disclosed herein are any and all ratios (and ranges of any such ratios) that may be formed by dividing a recited numeric value into any other recited numeric value. Accordingly, the skilled person will appreciate that many such ratios, ranges, and ranges of ratios may be unambiguously derived from the numerical values presented herein and in all instances such ratios, ranges, and ranges of ratios represent various embodiments of the present invention.

In some embodiments, the current invention relates to a composition comprising a cellulose product. In some embodiments, the composition comprises a cellulose product in an amount of at least about 45% by weight, based on the total weight of the composition on a dry basis, and the maximum amount of the cellulose product is not particularly limited. In another embodiment, the composition comprises a cellulose product in an amount of less than about 100% by weight, based on the total weight of the composition on a dry basis, and the minimum amount of the cellulose product is not particularly limited. For example, the composition can comprise a cellulose product in an amount of 44%, 45%, 46%, 48%, 50%, 52%, 54%, 56%, 58%, 60%, 62%, 64%, 66%, 68%, 70%, 72%, 74%, 76%, 78%, 80%, 82%, 84%, 86%, 88%, 90%, 92%, 94%, 96%, 98%, 99%, or 100%. Each of the foregoing numbers can be preceded by the word "about," "at least about," or "less than about," and any of the foregoing numbers can be used singly to describe an open-ended range or in combination to describe a close-ended range. For example and without limitation, the amount of the cellulose product in the composition can be at least about 45% by weight, about 45% by weight to about 100% by weight, or at least about 100%, by weight based on the total weight of the composition on a dry basis.

In one embodiment, and as readily appreciated by one of ordinary skill in the art, the cellulose product may comprise a number of crystalline structures. Natural cellulose, known as a type-I cellulose, can comprise $I_\alpha$ and $I_\beta$ structures. The amount of $I_\alpha$ and $I_\beta$ structures depends on the type of the natural cellulose. For example and without limitation, the cellulose produced by bacteria and algae may be enriched in $I_\alpha$, while cellulose of plants consists mainly of $I_\beta$. Type-I cellulose may be converted to a stable crystalline form of cellulose known as a type-II cellulose. The conversion of the type-I cellulose to the type-II cellulose may be achieved by different routes, for example and without limitation, by mercerization (alkali treatment), regeneration (solubilization followed by recrystallization), subcritical and supercritical water, ball milling of cellulose in presence of water and the like. The conversion may be irreversible, suggesting that the type-I cellulose is metastable and the type-II cellulose is stable. In another embodiment, additional types of the cellulose may be included. For example, and without limitation, a type-III cellulose and type-IV cellulose may be produced by various chemical treatments, such as treatment with liquid ammonia or certain amides such as ethylene diamine, or high temperature treatment in glycerol.

The type-I cellulose and type-II cellulose may be present in any amount in the cellulose product. In one embodiment, the cellulose product comprises type-I cellulose and type-II cellulose. In some embodiments, the cellulose product contains no type-II cellulose or substantially no type-II cellulose. In some embodiments, the cellulose product comprises type-II cellulose and unconverted type-I cellulose. In some embodiments, the cellulose product comprises unconverted type-I cellulose and no type-II cellulose or substantially no type-II cellulose. In some embodiments, the cellulose product further comprises cello-oligosaccharides. In some embodiments, the cellulose product further comprises lignin. It should be understood that each respective component present in the cellulose product may be present in any amount relative to the total weight percentage of the cellulose product. For example, and without limitation, the cellulose product can comprise type-I cellulose or type-II cellulose in any amount. The amounts described herein can apply to the amount of type-I cellulose in the cellulose product, the amount of type-II cellulose in the cellulose product, or the combined amount of type-I cellulose and type-II cellulose in the cellulose product, as will be clear by context. For example, the amount of type-I and/or type-II cellulose in the cellulose product can be 5%, 10%, 15%, 20%, 25%, 30%, 35%, 40%, 45%, 50%, 55%, 60%, 65%, 70%, 75%, 80%, 85%, 90%, 95%, or 100% by weight. Each of the foregoing numbers can be preceded by the word "about," "at least about," or "less than about," and any of the foregoing numbers can be used singly to describe an open-ended range or in combination to describe a close-ended range. For example, the type-I and/or type-II cellulose can be present in an amount of at least about 35% by weight, about 15% by weight to about 70% by weight, or less than about 80% by weight.

In some embodiments, there may be a type-III cellulose and/or a type-IV cellulose present in the cellulose product. The numerical weight percent ranges disclosed herein for the type-I cellulose and/or type-II cellulose may be used to describe the amount of any of these additional cellulose types, if present, either alone or in combination with one another as will be clear by context, and weight percent values are based on the total weight of the cellulose product (i.e., the total weight of all cellulose types, including amorphous if present, making up the cellulose product).

In some embodiments, the cellulose product can comprise cellulose having a weight-average molecular weight ($M_w$ in g/mol) of 2200, 2400, 2600, 2800, 3000, 3200, 3400, 3500, 3600, 3800, 4000, 4200, 4400, 4500, 4600, 4800, 5000, 5200, 5400, 5500, 5600, 5800, 6000, 6200, 6400, 6500, 6600, 6800, 7000, 7200, 7400, 7500, 7600, 7800, 8000, 8500, 9000, 9500, 10000, 10500, 11000, 11500, 12000, 12500, 13000, 13500, 14000, 14500, 15000, 15500, 16000, 16500, 17000, 17500, 18000, 18500, 19000, 19500, 20000, 20500, 21000, 21500, 22000, 22500, 23000, 23500, 24000, 24500, or 25000. Each of the foregoing numbers can be preceded by the word "about," "at least about," or "less than about," and any of the foregoing numbers can be used singly to describe an open-ended range or in combination to describe a close-ended range. For example, the $M_w$ of the cellulose product can be at least about 14000 g/mol, about 12000 g/mol to about 15500 g/mol, about 3000 g/mol to about 12000 g/mol, about 20000 g/mol to about 23500 g/mol, or less than about 13000 g/mol, as determined on a sample of the cellulose product that has been prepared for gel-permeation chromatography analysis according to a first condition.

The cellulose product can have any suitable $M_n$. For example, the $M_n$ (g/mol) can be 2000, 2500, 3000, 3500, 4000, 4500, 5000, 5500, 6000, 6500, 7000, 7500, 8000, 8500, 9000, 9500, 10000, 10500, or 11000. Each of the foregoing numbers can be preceded by the word "about," "at least about," or "less than about," and any of the foregoing numbers can be used singly to describe an open-ended range or in combination to describe a close-ended range.

The cellulose product can have any suitable $M_z$. For example, the $M_z$ (g/mol) can be 5000, 5500, 6000, 6500, 7000, 7500, 8000, 8500, 9000, 9500, 10000, 10500, 11000, 11500, 12000, 12500, 13000, 13500, 14000, 14500, 15000, 16000, 17000, 18000, 19000, 20000, 21000, 22000, 23000, 24000, 25000, 26000, 27000, 28000, 29000, 30000, 40000, 45000, 50000, 55000, 60000, 65000, 70000, 75000, 80000, 85000, 90000, 95000, or 100000. Each of the foregoing numbers can be preceded by the word "about," "at least about," or "less than about," and any of the foregoing numbers can be used singly to describe an open-ended range or in combination to describe a close-ended range.

The cellulose product can have any suitable $M_v$. For example, the $M_v$ (g/mol) can be 3000, 3500, 4000, 4500, 5000, 5500, 6000, 6500, 7000, 7500, 8000, 8500, 9000, 9500, 10000, 10500, 11000, 11500, 12000, 12500, 13000, 13500, 14000, 14500, 15000, 15500, 16000, 16500, 17000, 17500, 18000, 18500, 19000, 19500, or 20000. Each of the foregoing numbers can be preceded by the word "about," "at least about," or "less than about," and any of the foregoing numbers can be used singly to describe an open-ended range or in combination to describe a close-ended range.

In some embodiments, the cellulose product can comprise cellulose having a degree of polymerization (DP) of 10, 12, 14, 15, 16, 18, 20, 22, 24, 25, 26, 28, 30, 32, 34, 35, 36, 38, 40, 42, 44, 45, 46, 48, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, or 250. Each of the foregoing numbers can be preceded by the word "about," "at least about," or "less than about," and any of the foregoing numbers can be used singly to describe an open-ended range or in combination to describe a close-ended range. For example and without limitation, the DP can be at least about 215, at least about 55, about 85 to about 120, about 40 to about 95, about 45 to about 80, or less than about 145, as determined on a sample of the cellulose product that has been prepared for gel-permeation chromatography analysis according to a first condition. DP, as used herein (sometimes termed $DP_w$), is calculated from $M_w$, using the anhydroglucose molar weight of 162 mol/g.

The $M_w$, $M_n$, $M_z$, $M_v$, and DP reported herein for the cellulose product are different than those same parameters measured for microcrystalline cellulose (MCC), when solubilized for GPC measurement according to the first condition. See, for example, Example 13. The MCC used in this comparison was Acros Organics, cellulose microcrystalline, extra pure, average particle size 90 μm, product #382310010, and this MCC should be used for comparison purposes if available. If not available, then a comparable MCC should be used for comparison. Accordingly, in some embodiments, the cellulose product herein has an $M_n$ that is 0.05, 0.1, 0.15, 0.2, 0.25, 0.3, 0.35, 0.4, 0.45, 0.5, 0.55, 0.6, 0.65, or 0.7 times the $M_n$ of MCC. In some embodiments, the cellulose product herein has an $M_w$ that is 0.04, 0.02, 0.04, 0.06, 0.08, 0.1, 0.12, 0.14, 0.16, 0.18, 0.2, 0.22, 0.24, 0.26, 0.28, 0.3, 0.32, 0.34, 0.36, 0.38, 0.4, 0.42, 0.44, 0.46, 0.48, or 0.5 times the $M_w$ of MCC. In some embodiments, the cellulose product herein has an $M_z$ that is 0.01, 0.02, 0.03, 0.04, 0.05, 0.06, 0.07, 0.08, 0.09, 0.1, 0.12, 0.14, 0.15, 0.16, 0.18, 0.2, 0.22, 0.24, 0.26, 0.28, 0.3, 0.32, 0.34, or 0.36 times the $M_z$ of MCC. In some embodiments, the cellulose product herein has DP that is 0.04, 0.02, 0.04, 0.06, 0.08, 0.1, 0.12, 0.14, 0.16, 0.18, 0.2, 0.22, 0.24, 0.26, 0.28, 0.3, 0.32, 0.34, 0.36, 0.38, 0.4, 0.42, 0.44, 0.46, 0.48, or 0.5 times the DP of MCC. In some embodiments, the cellulose product herein has an $M_v$ that is 0.01, 0.02, 0.03, 0.04, 0.05, 0.06, 0.07, 0.08, 0.09, 0.1, 0.12, 0.14, 0.15, 0.16, 0.18, 0.2, 0.22, 0.24, 0.26, 0.28, 0.3, 0.32, 0.34, 0.36, 0.38, or 0.4 times the $M_v$ of MCC. Each of the foregoing numbers relating to the comparison of $M_w$, $M_n$, $M_z$, $M_v$, and DP for MCC and cellulose product can be preceded by "about," "at least about," or "less than about," and any of the foregoing numbers can be used singly to describe an open-ended range or in combination to describe a close-ended range. For example, the cellulose product has an $M_w$ that is less than about 0.5 times the $M_w$ of MCC.

The cellulose product can have any suitable hydrodynamic radius ($R_h(w)$), calculated from $M_w$ in nm. The $R_h(w)$ can be 1, 1.2, 1.4, 1.6, 1.8, 2, 2.2, 2.4, 2.6, 2.8, 3, 3.2, 3.4, 3.6, 3.8, 4, 4.2, 4.4, 4.6, 4.8, 5, 5.2, 5.4, 5.6, 5.8, 6, 6.2, 6.4, 6.6, 6.8, 7, 7.2, 7.4, 7.6, 7.8, 8, 8.2, 8.4, 8.6, 8.8, 10, 10.2, 10.4, 10.6, 10.8, 11, 11.5, or 12. Each of the foregoing numbers can be preceded by the word "about," "at least about," or "less than about," and any of the foregoing numbers can be used singly to describe an open-ended range or in combination to describe a close-ended range.

The cellulose product can have any suitable Mark-Houwink "a" constant, a parameter that can be measured using techniques well-known in the art. See, e.g., Masuelli, "Mark-Houwink Parameters for Aqueous-Soluble Polymers and Biopolymers at Various Temperatures" *Journal of Polymer and Biopolymer Physics Chemistry*, 2(2): 37-43 (2014), herein incorporated by reference in its entirety. For example, the "a" constant can be 0.2, 0.25, 0.3, 0.35, 0.4, 0.45, 0.5, 0.55, 0.6, 0.65, 0.7, or 0.75. Each of the foregoing numbers can be preceded by the word "about," "at least about," or "less than about," and any of the foregoing numbers can be used singly to describe an open-ended range or in combination to describe a close-ended range. Typically, "a" values of 0.5≤a≤0.8 are considered to have random-coil/flexible chains, whereas "a" values of a≤0.5 are compact/spherical chains.

The cellulose product can have any suitable PDI. For example, the PDI can be 1, 1.2, 1.4, 1.6, 1.8, 2, 2.2, 2.4, 2.6, 2.8, 3, 3.2, 3.4, 3.6, 3.8, or 4. Each of the foregoing numbers can be preceded by the word "about," "at least about," or "less than about," and any of the foregoing numbers can be used singly to describe an open-ended range or in combination to describe a close-ended range.

In some embodiments, the cellulose product can comprise any suitable proportion of cellulose having the properties disclosed herein. For example, the cellulose product can comprise any suitable proportion of cellulose having a $M_w$ as disclosed herein, any suitable proportion of cellulose having a DP as disclosed herein, etc. The proportions disclosed herein can apply to any $M_w$ range disclosed herein, any DP range as disclosed herein, and the like. For example, the cellulose product can comprise 80%, 82%, 84%, 86%, 88%, 90%, 92%, 94%, 96%, 98%, 99%, or 100% by weight of cellulose having a property specified herein (e.g., $M_w$, DP, etc.), based on the total weight of the cellulose product on a dry basis. Each of the foregoing numbers can be preceded by the word "about," "at least about," or "less than about," and any of the foregoing numbers can be used singly to describe an open-ended range or in combination to describe a close-ended range. For example and without limitation, about 100% by weight, based on the total weight of the cellulose product on a dry basis, of cellulose in the cellulose product has a weight-average molecular weight of about 3,000 g/mol to about 25,000 g/mol, and/or a degree of polymerization of about 50 to about 155, as determined on a sample of the cellulose product that has been solubilized according to the first condition. In other embodiments, at least about 80% by weight, based on the total weight of the cellulose product on a dry basis, of cellulose in the cellulose product has a weight-average molecular weight of about 5,000 g/mol to about 18,000 g/mol, and/or a degree of polymerization of about 30 to about 110, as determined on a sample of the cellulose product that has been solubilized according to the first condition. In some embodiments, less than about 100% by weight, based on the total weight of the cellulose product on a dry basis, of cellulose in the cellulose product has a weight-average molecular weight of about 3,000 g/mol to about 25,000 g/mol, as determined on a sample of the cellulose product that has been solubilized according to the first condition. In some embodiments, about at least about 85% by weight, based on the total weight of the cellulose product on a dry basis, of cellulose in the cellulose product has a degree of polymerization of about 55 to about 150, as determined on a sample of the cellulose product that has been solubilized according to the first condition. In some embodiments, at least about 80% by weight, based on the total weight of the cellulose product on a dry basis, of cellulose in the cellulose product has a weight-average molecular weight of about 3,000 g/mol to about 10,000 g/mol, and/or a degree of polymerization of about 20 to about 200, as determined on a sample of the cellulose product that has been solubilized according to the first condition.

In some embodiments, a substantial portion of the cellulose product can be solubilized when subjected to a series of steps adapted from the article: Dupont, *Polymer*, "Cellulose in lithium chloride/N,N-dimethylacetamide, optimization of a dissolution method using paper substrates and stability of the solutions," Vol. 44, (2003), 4117-4126, hereby incorporated by reference in its entirety. As used herein, the series of steps that enables solubilization of a substantial portion of the cellulose product, and also allows characterization by GPC, is termed the "first condition." The first condition consists of or consists essentially of the following sequential steps: (i) swelling the cellulose product twice in DI water for 1 hour each while stirring at room temperature (filter and re-suspend solids in fresh DI water after each swelling), (ii) activating the resulting solids twice in methanol for 45 minutes each at room temperature while stirring (filter and re-suspend solids in fresh methanol after each activating), (iii) activating the resulting solids in N,N-Dimethylacetamide (DMAc) (without LiCl) overnight at room temperature with stirring (followed by filtration of solids), (iv) stirring the resulting solids in 8% by weight LiCl in DMAc for 24 hours at room temperature, followed by (v) subjecting the same LiCl/DMAc mixture (without any filtration) at 2-8° C. for up to 3 days without stirring. All of the steps of the first condition are performed at ambient pressure. The weight-average molecular weight as determined by GPC typically is performed on the cellulose that has been solubilized according to the first condition, except the final solution of cellulose in 8 wt. % LiCl in DMAc has been diluted to 0.8 wt. % LiCl in DMAc prior to analyzing using GPC (see, e.g., Example 4). Unless stated otherwise, all molecular weight and associated measurements (e.g., PDI, Mark-Houwink constants, etc.) are made by GPC using a sample that has been prepared according to the "first condition."

As used herein, the "second condition" is a procedure used to prepare a cellulose sample for an analysis by GPC. The sample preparation procedure is described in Röhrling et al., discussed elsewhere herein. The "second condition" has aspects of the "first condition," but is somewhat different in that the second condition employs a fluorescence labeling technique that allows determination, e.g., of carbonyl groups. In the "second condition," a solution of the fluorescence label ([2-(2-aminooxyethoxy)ethoxy]amide "CCOA") is prepared by dissolving CCOA in 50 mL of 20 mM zinc acetate buffer, pH 4. About 20-25 mg of dry cellulose sample is then suspended in 4 mL of the acetate buffer containing the label. The suspension was then agitated at 40° C. for 168 h. The suspension was then filtered, and the solids activated by performing a solvent exchange from water to DMAc, followed by filtration. The activated solids were then dissolved in 2 mL of DMAc/LiCl (9%, w/v) at room temperature. The solutions were then diluted to 0.9% (w/v), filtered through a 0.45 μm filter, and then analyzed by GPC. The GPC system employed fluorescence, MALLS, and refractive index (RI) detectors with four serial columns. A dn/dc of 0.140 mL/g was used. The eluent was DMAc/LiCl (0.9%, w/v), flow of 1.00 mL/min, four columns in series (PL gel mixedA ALS, 20 μm, 7.5×300 mm), fluorescence detection (290 nm excitation, 340 nm emission), injection volume 100 μL, and run time 45 min.

As one of ordinary skill in the art would readily appreciate, the different crystalline phases of the cellulose product may be analyzed using X-ray diffraction (XRD). The specific XRD pattern of a crystalline solid reflects the crystal structure. Using Cu Kα radiation, the XRD spectrum of the type-I cellulose show two peaks at 2θ: a primary peak around 22.5° and a secondary peak around 15.5°. The XRD spectrum of the type-II cellulose shows a primary peak at 2θ around 19.9° and a secondary peak around 12.1°.

In one embodiment, at least a portion of the cellulose product exhibits a degree of crystallinity of 70%, 72%, 74%, 76%, 78%, 80%, 82%, 84%, 86%, 88%, 90%, 92%, 94%, 96%, 98%, 99%, or 100%. Each of the foregoing numbers can be preceded by the word "about," "at least about," or "less than about," and any of the foregoing numbers can be used singly to describe an open-ended range or in combination to describe a close-ended range. For example, the crystallinity can be about at least 90%, about 86% to about 96%, or less than about 88%.

Relative amounts of type-I cellulose, type-II cellulose, and amorphous cellulose can be measured using solid-state $^{13}C$ CP-MAS NMR spectroscopy, as described more fully in the examples herein. In some embodiments, the cellulose product comprises, consists of, or consists essentially of cellulose having a type-I structure, a type-II structure, an amorphous structure, or any combination thereof. In other words, the cellulose in the cellulose product can be type-I cellulose, type-II cellulose, amorphous cellulose, or any combination thereof. In some embodiments, the ratio of type-I cellulose to type-II cellulose in the cellulose product, on a dry weight basis, is about 0.5:9.5, 1:9, 1.5:9.5, 2:8, 2.5:7.5, 3:7, 3.5:6.5, 4:6, 4.5:5.5, 5:5, 5.5:4.5, 6:4, 6.5:3.5, 7:3, 7.5:2.5, 8:2, 8.5:1.5, 9:1, or 9.5:0.5. Each of the foregoing numbers can be preceded by the word "about," "at least about," or "less than about," and any of the foregoing numbers can be used singly to describe an open-ended range or in combination to describe a close-ended range. In some embodiments, the cellulose product comprises cellulose, wherein the cellulose is at least 99 wt. % type-II cellulose on a dry basis.

In some embodiments, the cellulose product can comprise type-I and type-II cellulose having any of the ratios herein, and the cellulose product can further comprise amorphous cellulose. The ratio of amorphous cellulose to total amount of type-I and type-II cellulose, on a dry weight basis, can be 0.5:9.5, 1:9, 1.5:9.5, 2:8, 2.5:7.5, 3:7, 3.5:6.5, 4:6, 4.5:5.5, 5:5, 5.5:4.5, 6:4, 6.5:3.5, 7:3, 7.5:2.5, 8:2, 8.5:1.5, 9:1, or 9.5:0.5. Each of the foregoing numbers can be preceded by the word "about," "at least about," or "less than about," and any of the foregoing numbers can be used singly to describe an open-ended range or in combination to describe a close-ended range.

In one embodiment, at least a portion of the cellulose product is present in a form of microcrystalline cellulose, nanocellulose, amorphous cellulose, or a combination thereof. In another embodiment, the cellulose product is substantially present in a form of nanocellulose. In a further embodiment the cellulose product is substantially present in a form of microcrystalline cellulose. In another embodiment, the cellulose product is substantially in a form of amorphous cellulose. In some embodiments, the cellulose product may further comprise self-assembled rods of cellulose. In other embodiments, the cellulose product may be present in any form and/or shape, including but not limited to, spherical, triangular, rhomboidal, rectangular, irregular, or combinations thereof.

In one embodiment, the cellulose product is characterized by an average particle size. As defined herein, the average particle size refers to the average diameter of the smallest sphere that can encompass the particle. The average particle size can be measured by any method known to one of ordinary skill in the art, including a light scattering technique (e.g., dynamic light scattering). The cellulose product can have an average particle size (nm) of 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, or 500. Each of the foregoing numbers can be preceded by the word "about," "at least about," or "less than about," and any of the foregoing numbers can be used singly to describe an open-ended range or in combination to describe a close-ended range. For example, the average particle size can be at least about 10 nm, about 95 nm to about 350 nm, or less than about 500 nm.

In certain embodiments, the cellulose product is present in a particulate form. Particulate forms of the cellulose product may have any desired particle size distribution characteristics. In one embodiment, the particle size distribution for the cellulose product is determined for the cellulose product that is substantially dried or that is substantially undried, as will be clear from context. Exemplary particle size distribution may include predetermined values of $D_{(n)}$, where (n) represents a mass percentage such as 5, 10, 15, 20, 25, 30, 35, 40, 45, 50, 55, 60, 65, 70, 75, 80, 85, 90, 95, or 100. The value of $D_{(n)}$ thus represents the particle size at which (n) percentage of the mass is finer. For example, the quantity $D_{(100)}$ represents the particle size at which 100% of the mass is finer. The quantity $D_{(90)}$ represents the particle size at which 90% of the mass is finer. The quantity $D_{(50)}$ is the median particle size of a mass for which 50% of the mass is finer. The quantity $D_{(25)}$ represents the particle size at which 25% of the mass is finer. The quantity $D_{(10)}$ represents the particle size at which 10% of the mass is finer. These particle sizes can apply to dry or undried particles.

In exemplary and non-limiting embodiments, the cellulose product has a particle size distribution with a $D_{10}$ (μm) of 0.4, 0.5, 0.6, 0.7, 0.8, 0.9, 1, 1.5, 2, 2.5, 3, 3.5, 4, 4.5, 5, 5.5, 6, 6.5, 7, 7.5, 8, 8.5, 9, 9.5, 10, 11, 12, 13, 14, 15, 16, 17, 18, 19, 20, 21, 22, 23, 24, 25, 26, 27, 28, 29, 30, 31, 32, 33, 34, or 35. Each of the foregoing numbers can be preceded by the word "about," "at least about," or "less than about," and any of the foregoing numbers can be used singly to describe an open-ended range or in combination to describe a close-ended range. For example, the $D_{10}$ can be at least about 0.4 μm, about 11 μm to about 29 μm, or less than about 20 μm.

In some embodiments, the cellulose product has a particle size distribution with a $D_{50}$ (μm) of 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, or 200. Each of the foregoing numbers can be preceded by the word "about," "at least about," or "less than about," and any of the foregoing numbers can be used singly to describe an open-ended range or in combination to describe a close-ended range. For example, the $D_{50}$ can be at least about 15 μm, about 25 μm to about 200 μm, or less than about 155 μm.

In some embodiments, the cellulose product has a particle size distribution with a $D_{90}$ (μm) of 40, 60, 80, 100, 120, 140, 160, 180, 200, 220, 240, 260, 280, 300, 320, 340, 360, 380, 400, 420, 440, 460, 480, 500, 520, 540, 560, 580, or 600. Each of the foregoing numbers can be preceded by the word "about," "at least about," or "less than about," and any of the foregoing numbers can be used singly to describe an open-ended range or in combination to describe a close-ended range. For example, the $D_{90}$ can be at least about 340 μm, about 80 μm to about 380 μm, or less than about 400 μm.

In some embodiments, the cellulose product disclosed herein can have a moisture content (%) of 0, 0.2, 0.4, 0.6, 0.8, 1, 1.2, 1.4, 1.6, 1.8, 2, 2.2, 2.4, 2.6, 2.8, 3, 3.2, 3.4, 3.6, 3.8, 4, 4.2, 4.4, 4.6, 4.8, 5, 5.2, 5.4, 5.6, 5.8, 6, 6.2, 6.4, 6.6, 6.8, 7, 7.2, 7.4, 7.6, 7.8, 8, 8.2, 8.4, 8.6, 8.8, 9, 9.2, 9.4, 9.6, 9.8, or 10. Each of the foregoing numbers can be preceded by the word "about," "at least about," or "less than about," and any of the foregoing numbers can be used singly to describe an open-ended range or in combination to describe a close-ended range. In certain embodiments, the cellulose product has a moisture content of at least about 1.2%, about 0.8% to about 2.9%, or less than about 4.6%. In some embodiments, the cellulose product has a moisture content of about 6.5% to about 8%. In other embodiments, the cellulose product has a moisture content of less than about 5%. In some embodiments, the cellulose product compactability can be affected by a moisture content. Test methods in accordance with USP <921> may be used for the moisture content determinations, hereby incorporated by reference in its entirety.

In certain embodiments, the cellulose product disclosed herein may exhibit any suitable loose bulk density (LBD). LBD is a common property for dry products and is a measure of the density of dry cellulose product. The LBD is the weight of the cellulose product relative to the volume of the cellulose product, without any substantial compaction. Test methods in accordance with USP <616> may be used for the loose bulk density determinations, hereby incorporated by reference in its entirety. The cellulose product can have a LBD (g/mL) of 0.15, 0.16, 0.18, 0.2, 0.22, 0.24, 0.26, 0.28, 0.3, 0.32, 0.34, 0.36, 0.38, 0.4, 0.42, 0.44, 0.46, 0.48, or 0.5. Each of the foregoing numbers can be preceded by the word "about," "at least about," or "less than about," and any of the foregoing numbers can be used singly to describe an open-ended range or in combination to describe a close-ended range. For example, the cellulose product has an LBD of at least 0.16 g/mL, about 0.24 g/mL to about 0.48 g/mL, or less than about 0.38 g/mL.

In certain embodiments, the water suspension of the cellulose product described herein can exhibit a pH of 5, 5.2, 5.4, 5.6, 5.8, 6, 6.2, 6.4, 6.6, 6.8, 7, 7.2, 7.4, 7.6, 7.8, 8, 8.2, 8.4, 8.6, 8.8, or 9. Each of the foregoing numbers can be preceded by the word "about," "at least about," or "less than about," and any of the foregoing numbers can be used singly to describe an open-ended range or in combination to describe a close-ended range. In some embodiments, the pH can be at least about 5.2, about 6.4 to about 7.1, or less than about 6.3. Test methods in accordance with USP <791> may be used for pH determinations, hereby incorporated by reference in its entirety.

In certain embodiments, the cellulose product described herein exhibits a loss on drying (LOD-%) of 0, 0.5, 1, 1.5, 2, 2.5, 3, 3.5, 4, 4.5, 5, 5.5, 6, 6.5, 7, 7.5, 8, 8.5, 9, 9.5, or 10. Each of the foregoing numbers can be preceded by the word "about," "at least about," or "less than about," and any of the foregoing numbers can be used singly to describe an open-ended range or in combination to describe a close-ended range. For example, the LOD can be at least about 1.5%, about 3.5% to about 7%, less than about 10%, or about 1% to about 7% by weight, based on the weight of the cellulose product. Test methods in accordance with USP <731> may be used for LOD determinations, hereby incorporated by reference in its entirety.

Cellulose materials of the invention may be used for human or animal consumption. To be in compliance with the regulations of the United States Food and Drug Administration (FDA) and other governmental agencies throughout the world, the cellulose product disclosed herein may be substantially free of hazardous impurities. In one embodiment, the cellulose product may comprise heavy metals in an amount (ppm) of 0, 0.02, 0.04, 0.06, 0.08, 0.1, 0.15, 0.2, 0.4, 0.6, 0.8, 1, 1.2, 1.4, 1.6, 1.8, 2, 2.2, 2.4, 2.6, 2.8, 3, 3.2, 3.4, 3.6, 3.8, 4, 4.2, 4.4, 4.6, 4.8, 5, 5.2, 5.4, 5.6, 5.8, 6, 6.2, 6.4, 6.6, 6.8, 7, 7.2, 7.4, 7.6, 7.8, 8, 8.2, 8.4, 8.6, 8.8, 9, 9.2, 9.4, 9.6, 9.8, or 10. Each of the foregoing numbers can be preceded by the word "about," "at least about," or "less than about," and any of the foregoing numbers can be used singly to describe an open-ended range or in combination to describe a close-ended range. For example, the heavy metals can be present in an amount of at least about 0.05 ppm, about 0.2 ppm to about 10 ppm, or less than about 4.8 ppm. Test methods in accordance with USP <231> may be used for the heavy metals determinations, hereby incorporated by reference in its entirety.

As used herein, heavy metals refer to the toxic metals. There is no standard definition assigning metals as heavy metals. Some lighter metals and metalloids are toxic and thus are termed heavy metals, while some heavy metals, such as gold, typically are not toxic. In some embodiments, the heavy metals described herein include but are not limited to the group of transition metals, some metalloids, lanthanides, actinides, and any combination thereof. In other embodiments, the heavy metals include but are not limited to lead, cadmium, vanadium, nickel, cobalt, mercury, chromium, arsenic, selenium, copper, manganese, iron, zinc, beryllium, aluminum, or any combination thereof.

In certain embodiments, the cellulose product can exhibit any suitable conductivity. For example, the conductivity (µS/cm) can be 0.055, 0.1, 0.5, 1, 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, or 80. For example, the conductivity can be less than about 58 µS/cm, about 16 µS/cm to about 74 µS/cm, or at least about 4 µS/cm. Suitable methods to measure conductivity are well known in the art. Each of the foregoing numbers can be preceded by the word "about," "at least about," or "less than about," and any of the foregoing numbers can be used singly to describe an open-ended range or in combination to describe a close-ended range.

In some embodiments, the cellulose product can have any suitable viscosity. For example, a dispersion of about 5.4 wt. % cellulose product in DI water at about 23° C. when measured at 1 rpm using spindle 21 can have a viscosity (cps) of 1500, 1550, 1600, 1650, 1700, 1750, 1800, 1850, 1900, 1950, 2000, 2050, 2100, 2150, 2200, 2250, 2300, 2350, 2400, 2450, 2500, 2550, 2600, 2700, 2800, 2900, 3000, 3100, 3200, 3300, 3400, 3500, 3600, 3700, 3800, 3900, or 4000. Each of the foregoing numbers can be preceded by the word "about," "at least about," or "less than about," and any of the foregoing numbers can be used singly to describe an open-ended range or in combination to describe a close-ended range.

In some embodiments, the cellulose product can have any suitable carbonyl content (CO), as determined on a sample of the cellulose product that has been prepared for gel-permeation chromatography analysis according to a second condition, as described in Röhrling et al. "A Novel Method for the Determination of Carbonyl Groups in Cellulosics by Fluorescence Labeling. 2. Validation and Applications," (*Biomacromolecules* (2002) 3, 969-975), hereby incorporated by reference in its entirety. Samples to be measured by this method are prepared as described in Example 14. For example, the CO content (µmol/g) can be 60, 62, 64, 66, 68, 70, 72, 74, 76, 78, 80, 82, 84, 86, 88, 90, 92, 94, 96, 98, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, or 300. Each of the foregoing numbers can be preceded by the word "about," "at least about," or "less than about," and any of the foregoing numbers can be used singly to describe an open-ended range or in combination to describe a close-ended range.

In certain embodiments, the composition described herein comprises an alcohol-soluble fraction, i.e., one or more components of the composition are capable of dissolving in an alcohol solvent. In another embodiment, the alcohol-soluble fraction is present in an amount (weight %, dry basis) of 0, 1, 2, 3, 4, 5, 6, 7, 8, 9, 10, 11, 12, 3, 14, 15, 6, 17, 18, 19, 20, 21, 22, 3, 24, 25, 26, 27, 28, 29, or 30. Each of the foregoing numbers can be preceded by the word "about," "at least about," or "less than about," and any of the foregoing numbers can be used singly to describe an open-ended range or in combination to describe a close-ended range. For example, the alcohol-soluble portion can be present in an amount of at least about 4% by weight, about 3% by weight to about 22% by weight, or less than about 5% by weight. In some embodiments, the composition comprises about 0% by weight of an alcohol-soluble portion, based on the weight of the composition on a dry basis. In some embodiments, the alcohol-soluble portion comprises lignin.

The solvent that is capable of dissolving the alcohol-soluble fraction of the composition can comprise any organic compound in which the hydroxyl functional group (—OH) is bound to a carbon atom. As one of ordinary skill in the art would readily appreciate, any possible alcohol is included in this disclosure. For example and without limitation, the alcohol can be selected from the group consisting of a primary, a secondary, and a tertiary alcohol, wherein the classification is based upon the number of carbon atoms connected to the carbon atom bounded to the hydroxyl (OH) functional group. The primary alcohols have the general formula $RCH_2OH$; secondary alcohols have the general formula $RR'CHOH$; and tertiary alcohols have the general formula $RR'R''COH$, where R, R', and R'' stand for alkyl groups. For example and without limitation, the alcohol can be methanol, ethanol, propanol, butanol, isopropanol, tert-butylalcohol, benzyl alcohol, 1,4-butadienol, 1,2,4-butanetriol, dietheylene glycol, ethylene glycol, 2-ethyhexanol, furfuryl alcohol, glycerol, isobutanol, 2-(2-methoxyethan-oxy)ethanol, 2-methyl-1-butanol, 2-methyl-1-pentanol, 3-methyl-2-butanol, neopentyl alcohol, 2-pentanol, 1,3-propanediol, propylene glycol, or a combination thereof, and like. In certain embodiments, the alcohol is methanol, ethanol, or a combination thereof.

In one embodiment, the alcohol-soluble fraction of the composition comprises lignin having any suitable weight-average molecular weight. For example, the weight-average molecular weight (g/mol) can be 1000, 1250, 1500, 1750, 2000, 2250, 2500, 2750, 3000, 3250, 3500, 3750, 4000, 4250, 4500, 4750, 5000, 5250, 5500, 5750, 6000, 6250, 6500, 6750, 7000, 7250, 7500, 7750, 8000, 8250, 8500, 8750, 9000, 9250, 9500, 9750, or 1000. Each of the foregoing numbers can be preceded by the word "about," "at least about," or "less than about," and any of the foregoing numbers can be used singly to describe an open-ended range or in combination to describe a close-ended range. For example, the weight-average molecular weight of lignin in the alcohol-soluble fraction of the composition can be at least about 1,250 g/mol, about 2,500 g/mol to about 7,500 g/mol, less than about 2,500 g/mol, or about 1,750 g/mol to about 2,000 g/mol. In some embodiments, the alcohol-soluble fraction can be obtained from step (ii) of the first condition, as described elsewhere herein.

In certain embodiments, the composition further comprises a water-soluble fraction. In certain embodiments, the water-soluble fraction comprises at least one cello-oligosaccharide. In some embodiments, the water-soluble fraction comprises at least one cello-oligosaccharide in an amount (wt. %, based on total weight of the composition on a dry basis) of 0, 1, 2, 3, 4, 5, 6, 7, 8, 9, 10, 11, 12, 13, 14, 15, 16, 17, 18, 19, or 20. Each of the foregoing numbers can be preceded by the word "about," "at least about," or "less than about," and any of the foregoing numbers can be used singly to describe an open-ended range or in combination to describe a close-ended range. For example, the at least one cello-oligosaccharide can be present in an amount of at least about 12% by weight, about 2% by weight to about 18% by weight, or less than about 16% by weight, based on the total weight of the composition on a dry basis. The terms "cello-oligosaccharide" and "gluco-oligosaccharide" are used interchangeably herein.

In one embodiment, the cellulose product described herein comprises water-soluble substances in an amount (wt. %, based on total weight of the cellulose product on a dry basis) of 0, 0.02, 0.04, 0.06, 0.08, 0.1, 0.12, 0.14, 0.16, 0.18, 0.2, 0.22, 0.24, 0.26, 0.28, or 0.3. Each of the foregoing numbers can be preceded by the word "about," "at least about," or "less than about," and any of the foregoing numbers can be used singly to describe an open-ended range or in combination to describe a close-ended range. For example, the amount of the water-soluble substances can be at least about 0.14%, about 0.01% to about 0.24%, or less than about 0.2%, based on the total weight of the cellulose product on a dry basis. Test methods in accordance with the flask method of OECD 105 may be used for the water-soluble substances determinations, hereby incorporated by reference in its entirety.

In one embodiment, the at least one cello-oligosaccharide has a weight-average molecular weight (g/mol) of 200, 250, 300, 350, 400, 450, 500, 550, 600, 650, 700, 750, 800, 850, 900, 950, 1000, 1050, 1100, 1150, 1200, 1250, 1300, 1350, 1400, 1450, or 1500. Each of the foregoing numbers can be preceded by the word "about," "at least about," or "less than about," and any of the foregoing numbers can be used singly to describe an open-ended range or in combination to describe a close-ended range. For example and without limitation, the weight-average molecular weight is at least about 300 g/mol, about 450 g/mol to about 1,350 g/mol, or less than about 1,150 g/mol. In some embodiments, the weight-average molecular weight can be about 600 g/mol to about 750 g/mol, or about 500 g/mol to about 800 g/mol. In some embodiments, the cello-oligosaccharides can be extracted in the liquid fraction of step (i) of the first condition.

In certain embodiments, the at least one cello-oligosaccharide comprises at least one compound selected from the group consisting of cellohexaose, cellopentaose, cellotetraose, cellotriose, cellobiose, glucose, and any combination thereof. In some embodiments, the composition comprises at least two cello-oligosaccharides. In embodiments where the at least two cello-oligosaccharides are present, it should be understood that each respective cello-oligosaccharide may be present in any desired amount relative to the total weight percentage of the at least two cello-oligosaccharides.

In some embodiments, the water-soluble fraction further comprises a degradation product. In certain embodiments, the degradation product is hydroxymethylfurfural, glycolaldehyde, glyceraldehyde, formic acid, levulinic acid, lactic acid, pyruvaldehyde, dihydroxyacetone, furfural, formaldehyde, glucuronic acid, furan, or any combination thereof.

In certain embodiments, the composition comprises a C5 saccharide selected from the group consisting of xylose, xylo-oligosaccharides, xylan, and any combination thereof, based on the total weight of the composition on a dry basis. The amount (wt. %, dry basis, based on total weight of the composition) of this C5 saccharide can be 0, 0.5, 1, 1.5, 2, 2.5, 3, 3.5, 4, 4.5, or 5. Each of the foregoing numbers can be preceded by the word "about," "at least about," or "less than about," and any of the foregoing numbers can be used singly to describe an open-ended range or in combination to describe a close-ended range. For example, the C5 saccharide can be present in an amount of at least about 0% by weight, about 0% by weight to about 5% by weight, or less than about 5% by weight based on the total weight of the composition on a dry basis. In some embodiments, the C5 saccharide comprises or consists of xylose. In another embodiment, the C5 saccharide comprises or consists of xylan. In yet another embodiment, the C5 saccharide comprises or consists of xylose and xylan. In some embodiments, the composition comprises 0% (or about 0%) C5 saccharide by weight, based on the total weight of the composition on a dry basis.

In certain embodiments, the composition further comprises an insoluble species. The insoluble species can be char particles, high molecular weight lignin, high molecular weight polyfuran, saccharide crystals (e.g., crystalline xylose, crystalline glucose, crystalline cellulose, crystalline xylan, crystalline cello-oligosaccharides, crystalline xylo-oligosaccharides, or any combination thereof), or a combination thereof. The amount (wt. %, dry basis, based on total weight of the composition) of insoluble species can be 0, 0.5, 1, 1.5, 2, 2.5, 3, 3.5, 4, 4.5, 5, 5.5, 6, 6.5, 7, 7.5, or 8. Each of the foregoing numbers can be preceded by the word "about," "at least about," or "less than about," and any of the foregoing numbers can be used singly to describe an open-ended range or in combination to describe a close-ended range. For example, the insoluble species can be present in an amount of at least about 2.5% by weight, about 0.5% by weight to about 6% by weight, or less than about 7% by weight. In some embodiments, the insoluble species is not present (i.e., is present in an amount of 0% by weight).

In certain embodiments, the composition can exhibit a white color. In other embodiments, the composition can exhibit a brown color. In a yet further embodiment, the composition can exhibit a gray color. As one of ordinary skill in the art would readily appreciate, the composition is not limited to any specific color.

The cellulose product of the invention may be used in multiple fields and applications, for example and without limitation, paper products, various fibers manufacturing, consumables, food, pharmaceuticals, cosmetics, as a renewable energy source, building materials and many more. In certain embodiments, the cellulose product may be used in various pharmaceutical applications. In some embodiments, the pharmaceutical applications comprise use of the cellulose product as a carrier material, a spheronizing agent, a topical drug deliverer, an excipient, or any combination thereof.

In certain embodiments, the composition disclosed herein further comprises at least one pharmaceutically-active ingredient. In some embodiments, the composition comprising the at least one pharmaceutically-active ingredient may form a pharmaceutical composition.

In some embodiments, a pharmaceutically active ingredient comprises any substance or mixture of substances that, for example, furnish pharmacological activity or otherwise directly affect the diagnosis, cure, mitigation, treatment, or prevention of disease or to affect the structure, function, or metabolism of the body.

In certain pharmaceutical applications, the cellulose product may be directly compressed alone without the aid of a lubricant. In some embodiments, the compression may be carried out at a specified humidity, for example, at less than about 55%. In some embodiments, when a specific formulation is required, a lubrication aid may need to be added. As one of ordinary skill in the art would readily appreciate, in the manufacture of pharmaceuticals to form tablets, various additives may be used. For example and without limitation, additives such as magnesium stearate, calcium stearate, and/or sodium stearyl fumarate can be used. In some embodiments, the cellulose products having larger particles are more sensitive to the presence of a lubricant than the cellulose products having smaller particles. It is believed that the difference in particle surface area can affect a substance's sensitivity to a lubricant. For example, and without limitation, the cellulose product having a particle size about 0.4 μm to about 100 μm may be less sensitive to the lubricant than the cellulose product having a particle size about 100 μm to about 600 μm.

In some embodiments, when compressed, the cellulose product may undergo plastic deformation. In certain embodiments, the strength of the formed tablets comprising the cellulose product may result from the hydrogen bonding between the plastically deformed, high surface area cellulose particles. In some embodiments, due to the high compressibility of the cellulose product, less compression force may be required to produce a tablet of a given hardness than may be required for other compression excipients.

In some embodiments, the cellulose product can be used as a direct compression excipient in a direct compression formulation. The amount (wt. %, based on the weight of the formulation) of cellulose product in the direct compression formulation can be 5, 6, 8, 10, 12, 14, 15, 16, 18, 20, 22, 24, 25, 26, 28, 30, 32, 34, 35, 36, 38, 40, 42, 44, 45, 46, 48, 50, 52, 54, 55, 56, 58, 60, 62, 64, 65, 66, 68, or 70. Each of the foregoing numbers can be preceded by the word "about," "at least about," or "less than about," and any of the foregoing numbers can be used singly to describe an open-ended range or in combination to describe a close-ended range. For example, the amount of the cellulose product in the direct compression formulation can be at least about 15%, about 25% to about 66%, less than about 28%, about 5% to about 15%, or about 40% to about 65%.

In one embodiment, the cellulose product is used to form a compact. As one of ordinary skill in the art would readily appreciate, pore volume and median pore diameter of particles can be important for compactability. In some embodiments, to form the compact, a powder comprising the cellulose product is compacted. In certain embodiments, the formed compact may possess a porosity having a certain median pore diameter that may depend, at least in part, on the particle size of the cellulose product used for the compaction. In some embodiments, the median pore diameter (μm) of the pores in the formed compact can be 10, 15, 20, 25, 30, 35, 40, 45, 50, 55, 60, 65, 70, 75, 80, 85, 90, 95, or 100. Each of the foregoing numbers can be preceded by the word "about," "at least about," or "less than about," and any of the foregoing numbers can be used singly to describe an open-ended range or in combination to describe a close-ended range. In some embodiment, the median pore diameter can depend on an initial size of the cellulose product particles. For example, and without limitation, the cellulose product comprising particles having a particle size of about 160 µm to about 350 µm can form a compact having porosity with a median pore diameter of about 40 µm to about 100 µm. In yet another embodiment, the cellulose product comprising particles having a particle size less than about 160 µm can form a compact having porosity with a median pore diameter of about 10 µm to about 40 µm. In other embodiments, the compact can have any of the median pore diameter disclosed herein that can be combined with and applied to any of the particle size ranges disclosed herein.

In one embodiment, the composition described herein further comprises a dispersing agent. As used herein, the dispersing agent refers to any substance that when added to the sample suspension improves the separation of particles and assists in prevention of stickiness or settling. The dispersing agent can include a non-surface active substance or a surface-active substance. Addition of dispersing agents may affect chemical and physical properties of the sample, for example, dispersing agents may deflocculate solids or reduce the viscosity of a final dispersion or paste. In some embodiments, addition of a dispersing agent may allow formation of final dispersions having higher amounts of dispersed powdered material. As one of ordinary skill in the art would readily appreciate, the dispersing additive may be useful to produce stable formulations and ensure longer shelf life and storage. Suitable dispersing agents include acacia, alginic acid, colloidal silicon oxide, gelatin, hydroxyl propyl cellulose, hydroxyl propyl methyl cellulose, hypromellose, microcrystalline cellulose, methyl cellulose, carboxymethylcellulose, sodium carboxymethylcellulose, paraben derivatives, sucrose, sodium alignate, or any combination thereof. In yet another embodiment, the dispersing agent comprises carboxymethylcellulose, paraben derivatives, or a combination thereof. In a further embodiment, the dispersing agent is carboxymethylcellulose having a degree of substitution of 0.4, 0.5, 0.6, 0.7, 0.8, 0.9, 1, 1.2, 1.3, 1.4, or 1.5. Each of the foregoing numbers can be preceded by the word "about," "at least about," or "less than about," and any of the foregoing numbers can be used singly to describe an open-ended range or in combination to describe a close-ended range. For example, the degree of the substitution can be at least about 0.5, about 0.7 to about 1.3, or less than about 0.8.

In certain embodiments, a weight ratio of the cellulose product to the carboxymethylcellulose is 70:30, 72:28, 74:26, 76:24, 78:22, 79:21, 80:20, 81:19, 82:18, 84:16, 86:14, 88:12, 90:10, 92:8, 93:7, 94:6, or 95:5. Each of the foregoing numbers can be preceded by the word "about," "at least about," or "less than about," and any of the foregoing numbers can be used singly to describe an open-ended range or in combination to describe a close-ended range. For example, the weight ratio can be at least about 79:21, about 81:19 to about 93:7, or less than about 90:10.

In certain embodiments, the invention described herein relates to a method comprising: providing a feedstock comprising a type-I cellulose; converting at least a portion of the type-I cellulose to a type-II cellulose; and hydrolyzing at least a portion of the type-II cellulose.

In one embodiment, the feedstock includes a lignocellulosic feedstock, cellulosic feedstock, hemicellulosic feedstock, starch-containing feedstocks, and any other feedstock as described elsewhere herein. In another embodiment, the feedstock comprises lignocellulosic biomass. Other suitable feedstocks are disclosed hereinabove (e.g., any "biomass" as defined hereinabove). In some embodiments, the feedstock is fractionated biomass, as defined herein. In some embodiments, the feedstock is unfractionated biomass (i.e., biomass that has not been fractionated as defined herein).

In one embodiment, the converting comprises contacting the feedstock with a fluid. The fluid may be any suitable fluid, including without limitation, a single component fluid or a multi-component fluid. In one embodiment, the fluid is selected from the group consisting of water, carbon dioxide, sulfur dioxide, methanol, ethanol, isopropanol, propanol, butanol, pentanol, and any combination thereof. In another embodiment, the fluid comprises, consists of, or consists essentially of water. In some embodiments, the fluid is a combination of water and ethanol, water and carbon dioxide, or water and sulfur dioxide. In some embodiments, and as described elsewhere herein, the contacting may be a physical contact of a feedstock stream with the fluid. In some embodiments, the contacting refers to forming a mixture of the feedstock stream and the fluid that, when exposed to specified conditions, can generate a fluid at the specified conditions (e.g., can generate a fluid in a particular state, such as a sub-critical, near-critical, or supercritical state). In these embodiments, the feedstock is in contact with the fluid at the specified conditions. In some embodiments, the converting comprises contacting type-I cellulose with a fluid as described herein, followed by reducing the temperature, pressure, or both, or otherwise quenching the reaction as defined elsewhere herein. Without wishing to be bound by theory, it may be possible that at least a portion of the type-I cellulose is solubilized as shorter chain cellulose polymers upon contacting with the fluid. Upon reducing the temperature, pressure, or both, or otherwise quenching, type-II cellulose may crystallize from the solubilized cellulose. It is hypothesized that this type-II cellulose is more susceptible to hydrolysis than type-I cellulose, which may be one reason that higher than expected yields are observed when employing a recycling step—the type-II cellulose recycled to the raw biomass feed hydrolyzes easier than the type-I cellulose, thereby increasing yields (see examples herein).

In certain embodiments, the fluid is in a sub-critical state, near-critical state, or supercritical state prior to the contacting. In some embodiments, the converting is carried out under conditions sufficient to maintain a sub-critical fluid state, near-critical fluid state, or supercritical fluid state (i.e., even after contacting). In other embodiments, the term "under conditions sufficient to" refers to conditions that control the state of the fluid and include, but are not limited to, pressure and temperature. In certain embodiments, the pressures and temperatures for the sub-critical fluid, near-critical fluid, or supercritical fluid will vary with the choice of the fluid or fluids used in the contacting. In some embodiments, the fluid at conditions sufficient to maintain sub-critical fluid state, near-critical fluid state, or supercritical fluid state may be present in a single phase, or may be present in multiple phases. In one embodiment, the fluid comprises hot compressed water. In another embodiment, the fluid comprises supercritical water. In a further embodiment, the converting is carried out under conditions sufficient to maintain water in a sub-critical state or a near-critical state. In a yet further embodiment, the converting is carried out under conditions sufficient to maintain water in a supercritical state. In some embodiments, the sub-critical fluid, near-critical fluid, or supercritical fluid is substantially free of an exogenous acid (i.e., is substantially free of an acid that has been deliberately added to the contacting fluid). In certain embodiments, the converting is carried out using a fluid, and the converting is carried out under a pressure sufficient to maintain all of the fluid in liquid form or supercritical form.

The temperature of the converting will be chosen, at least in part, on the identity of the fluid or fluids employed. In some embodiments, the temperature (° C.) can be 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, or 500. Each of the foregoing numbers can be preceded by the word "about," "at least about," or "less than about," and any of the foregoing numbers can be used singly to describe an open-ended range or in combination to describe a close-ended range. For example, the temperature can be at least about 120° C., about 360° C. to about 390° C., less than about 400° C., or about 360° C. to about 420° C.

The contacting may be performed at any suitable pressure. In some embodiments, the pressure (bar) can be 1, 5, 10, 20, 30, 40, 50, 60, 70, 80, 90, 100, 110, 120, 125, 130, 140, 150, 160, 170, 175, 180, 190, 200, 210, 220, 225, 230, 240, 250, 260, 270, 275, 280, 290, 300, 310, 320, 325, 330, 340, 350, 360, 370, 380, 390, or 400. Each of the foregoing numbers can be preceded by the word "about," "at least about," or "less than about," and any of the foregoing numbers can be used singly to describe an open-ended range or in combination to describe a close-ended range. For example, the pressure can be at least about 20 bar, about 70 bar to about 275 bar, or less than about 250 bar. In some embodiments, the pressure is sufficient to maintain the fluid in liquid form. In some embodiments, the pressure is sufficient to maintain the fluid in supercritical form.

The converting may be performed for any suitable residence time. In some embodiments, the residence time (sec) can be 0.05, 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.5, 3, 3.5, 4, 4.5, 5, 6, 7, 8, 9, 10, 20, 30, 40, 50, or 60. Each of the foregoing numbers can be preceded by the word "about," "at least about," or "less than about," and any of the foregoing numbers can be used singly to describe an open-ended range or in combination to describe a close-ended range. In some embodiments, the residence time (min) can be 2, 4, 6, 8, 10, 20, 30, 40, 50, 60, 70, 80, 90, 100, 110, 120, 130, 140, 150, 160, 170, 180, 190, 200, 220, 240, 260, 280, or 300. Each of the foregoing numbers can be preceded by the word "about," "at least about," or "less than about," and any of the foregoing numbers can be used singly to describe an open-ended range or in combination to describe a close-ended range. For example, the residence time can be at least about 0.1 sec, about 0.5 sec to about 2 sec, less than about 90 min, about 0.3 sec to about 1.5 sec, or about 60 min to about 150 min.

In certain embodiments, the converting produces a composition comprising a cellulose product, wherein the cellulose product comprises an unconverted type-I cellulose and type-II cellulose. In certain embodiments, the type-II cellulose in the composition is not hydrolyzed to oligosaccharides for a specified period of time after the converting is completed (i.e., for a specified time period from the end of the residence time of the converting). The specified time period is greater than 0 sec, since the hydrolyzing and the converting are no contemporaneous. In some embodiments, the specified period of time (sec) can be 0.01, 0.1, 0.5, 1, 1.5, 2, 2.5, 3, 3.5, 4, 4.5, 5, 5.5, 6, 6.5, 7, 7.5, 8, 8.5, 9, 9.5, 10, 15, 20, 25, 30, 60, 120, 150, 200, 250, 300, 400, 500, 600, 700, 800, 900, 1000, 1200, 1400, 1600, 1800, 2000, 2200, 2400, 2600, 2800, 3000, 3200, 3400, or 3600. Each of the foregoing numbers can be preceded by the word "about," "at least about," or "less than about," and any of the foregoing numbers can be used singly to describe an open-ended range or in combination to describe a close-ended range. For example, the specified period of time can be at least about 0.5 sec, about 1 sec to about 10 sec, or less than about 3000 sec.

In further embodiments, the hydrolyzing is carried out on the composition produced in the converting. In other embodiments, at least a portion of the unconverted type-I cellulose is separated from the type-II cellulose in the composition prior to the hydrolyzing. As used herein, the "converting" step is a different step from the "hydrolyzing" step. For example, the converting may take place in a converting reactor, and the hydrolyzing will then take place somewhere that is not the converting reactor; however, this does not mean that different reactors are needed to carry out the two steps. Rather, the two steps could be carried out in the same reactor, or in adjacent portions of an apparatus, or elsewhere, provided that the steps are different in some material way, e.g., different conditions such as temperature or pressure, or a separate run of the "converted" material in the same converting reactor that effects the "hydrolyzing."

In other words, the converting and hydrolyzing are different steps, which steps are different by location, condition, or point in time (converting at point in time x vs. hydrolyzing at a point in time that is later, e.g., x+1). It is not contemplated that the hydrolyzing and converting steps take place simultaneously in a single step. While some amount of hydrolyzing may be taking place during a converting step, the majority of hydrolysis of the converted material will take place in a separate step, and it is this separate nature of the converting and hydrolyzing steps that is contemplated herein. For example, converting may take place at 400° C. for 2 seconds in a tubular reactor, followed by cooling to a temperature of 200° C. downstream of the tubular reactor, where the cooled mixture is held for about 1 min during a hydrolysis step, followed by cooling to ambient temperature. In this case, the 400° C. condition is the converting step, and the 200° C. condition is the hydrolysis step. However, any hydrolysis that may be happening during the 400° C. converting step is not a "hydrolyzing step" as used herein, since this hydrolysis is happening in the converting step.

In some embodiments, the composition produced by the method described herein further comprises lignin. In one embodiment, the method further comprises separating the lignin from the cellulose product using, for example, gravity separation, centrifugal separation, centripetal separation, filtration, or any combination thereof. In another embodiment, the method comprises separating the lignin from the cellulose product using a hydrocyclone. In another embodiment, at least a portion of the lignin is removed in an underflow of the hydrocyclone. In yet another embodiment, at least a portion of the cellulose product is removed in an overflow of the hydrocyclone.

Without wishing to be bound by theory, it is believed that the setting rate of particles in gravitational or centrifugal force fields is proportional to the difference between particle and liquid densities. Thus, the denser particles are generally removed in the underflow of a hydrocyclone and the less dense particles are generally removed in the overflow. In order to remove denser particles (e.g., cellulosic oligomers) in the overflow stream, those particles need to be made much smaller than the less dense lignin type particles. A rapid quench of a solution of supersaturated dissolved cellulose oligomers produces desirably small particle sizes. In this way, the denser particles can be made smaller than the less dense particles, and the denser particles can then be removed in the overflow of the hydrocyclone. As a result, the finer cellulosic oligomer particles can be separated from the lignin particles prior to filtration (e.g., using a filter press) to avoid problems encountered when attempting to filter fine particles (e.g., slow filtration, and the tendency of the small particles to become entrapped in the lignin-rich filter cake, which can avoid a yield loss).

In certain embodiments, the hydrolyzing comprises a method selected from the group consisting of supercritical hydrolysis, sub-critical hydrolysis, near-critical hydrolysis, hot compressed water hydrolysis, acid hydrolysis, enzyme hydrolysis, heat hydrolysis, and any combination thereof.

The hydrolyzing can be carried out at any suitable temperature. In some embodiments, the hydrolyzing is carried out at the same temperature as the converting. In some embodiments, the hydrolyzing is carried out at a lower temperature than the converting. In some embodiments, the hydrolyzing can be carried out at a temperature that is lower (in %) than the converting temperature by 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, or 70%. Each of the foregoing numbers can be preceded by the word "about," "at least about," or "less than about," and any of the foregoing numbers can be used singly to describe an open-ended range or in combination to describe a close-ended range. For example, the hydrolyzing temperature can be at least about 4% lower, about 12% to about 42% lower, or less than about 50% lower than the converting temperature.

In some embodiments, the hydrolyzing temperature is lower (in ° C.) than the converting temperature by 5, 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, or 350° C. Each of the foregoing numbers can be preceded by the word "about," "at least about," or "less than about," and any of the foregoing numbers can be used singly to describe an open-ended range or in combination to describe a close-ended range. For example, the hydrolyzing temperature can be at least about 50° C., about 70° C. to about 250° C., or less than about 300° C. lower than the converting temperature. Any of these hydrolyzing temperatures may also apply to the "specified threshold temperature" as discussed in the following paragraph.

In certain embodiments, the converting involves the use of thermal energy. In some embodiments, the thermal energy comprises residual heat from another portion of the system. In some embodiments, at least a portion of the thermal energy used in the converting and/or the hydrolyzing is derived from (i.e., recovered and/or recycled from) the converting and/or the hydrolyzing. In some embodiments, heat is captured from the converting, for example, using heat exchangers and/or flash cooling, and this thermal energy is recycled to the hydrolyzing. In another embodiment, the hydrolyzing is carried out using residual heat from the converting. For example, the hot mixture that exits the converting is cooled slightly (e.g., using a flash tank and/or a heat exchanger) and held at the lower temperature (or above a "specified threshold temperature") for a predetermined period of time sufficient to effect the hydrolyzing, before finally being cooled further (e.g., using a flash tank, a heat exchanger, and/or passive cooling, etc.) (e.g., eventually to ambient conditions). In embodiments where a specified threshold temperature is employed, any of the temperatures disclosed hereinabove for the hydrolyzing temperature can be used as the specified threshold temperature. In some embodiments, the predetermined period of time (sec) can be 5, 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 330, 360, 390, 420, 450, 480, 510, 540, 570, 600, 750, 900, 1050, 1200, 1350, 1500, 1650, 1800, 1950, 2100, 2250, 2400, 2550, 2700, 2850, or 3000. Each of the foregoing numbers can be preceded by the word "about," "at least about," or "less than about," and any of the foregoing numbers can be used singly to describe an open-ended range or in combination to describe a close-ended range. For example, the predetermined period of time can be at least about 10 sec, about 20 sec to about 300 sec, about 20 sec to about 120 sec, about 30 sec to about 150 sec, or less than about 300 sec.

In some embodiments, the converting is conducted at a temperature above about 100° C., and the type-II cellulose produced in the converting is maintained at a temperature above about 100° C. prior to the hydrolyzing, and optionally during the hydrolyzing.

In some embodiments, the converting produces a stream at a first temperature, and the method further comprises: lowering the first temperature of the stream to a second temperature; maintaining the stream at the second temperature for a period of time, and changing the stream to a third temperature prior to the hydrolyzing, wherein the hydrolyzing is conducted at a fourth temperature that may be the same as or different from the third temperature. The first, second, and/or third temperatures can be any temperature recited hereinabove for the converting. For example, the first temperature can be about 50° C. to about 500° C., or any range associated therewith as disclosed hereinabove. In some embodiments, the first, second, third, and/or fourth temperatures can be described in relative terms (i.e., higher and/or lower than one another), and the temperatures disclosed hereinabove relating to the relative temperatures of the converting and hydrolyzing can also be applied to the first, second, third, and/or fourth temperatures. For example, in some embodiments, the third temperature can be greater than the second temperature by at least about 90° C., about 50° C. to about 160° C., or less than about 270° C. In a yet further embodiment, the third temperature can be lower than the second temperature by at least about 150° C., about 180° C. to about 300° C., or no more than about 210° C. In certain embodiments, the third temperature can be the same as the second temperature. In other embodiments, the fourth temperature can be greater or lower than the third temperature by at least about 30° C., about 190° C. to about 220° C., or less than about 140° C. In certain embodiments, the fourth temperature is the same as the third temperature.

The second temperature can be maintained for any suitable period of time. For example, the period of time (sec) can be 5, 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 330, 360, 390, 420, 450, 480, 510, 540, 570, or 600. Each of the foregoing numbers can be preceded by the word "about," "at least about," or "less than about," and any of the foregoing numbers can be used singly to describe an open-ended range or in combination to describe a close-ended range. For example, the period of time can be at least about 50 sec, about 40 sec to about 310 sec, about 20 sec to about 120 sec, about 30 sec to about 150 sec, or less than about 180 sec.

In some embodiments, the hydrolyzing produces at least one of a monosaccharide and an oligosaccharide. In certain embodiments, the monosaccharide comprises a saccharide selected from the group consisting of a C5 monosaccharide, a C6 monosaccharide, and a combination thereof. In certain embodiments, the oligosaccharide comprises a saccharide selected from the group consisting of a C5 oligosaccharide, a C6 oligosaccharide, and a combination thereof. C5 saccharides include arabinose, lyxose, ribose, xylulose, or combinations thereof. C6 saccharides include glucose, mannose, galactose, cello-oligosaccharides, or combinations thereof.

In some embodiments, the method further comprises hydrolyzing at least a portion of the type-II cellulose. In some embodiments, the method further comprises hydrolyzing at least a portion of the unconverted type-I cellulose at the same or different conditions than the converting. In some embodiments, hydrolyzing at least a portion of the unconverted type-I cellulose at the same conditions can be achieved by recycling the cellulose exiting the process back to the beginning of the process again to be combined with fresh feedstock, as described elsewhere herein. In some embodiments, the type-II cellulose may be selectively hydrolyzed over the unconverted type-I cellulose. In some embodiments, the type-I cellulose (e.g., unconverted type-I cellulose) may be selectively hydrolyzed over the type-II cellulose. The hydrolysis may be considered "selective" when a larger proportion of one cellulose type is hydrolyzed than another cellulose type, relative to the respective weight of each cellulose type (i.e., type-I and type-II) prior to the hydrolysis (i.e., in the cellulose product prior to hydrolysis). For example, the hydrolysis may be considered "selective" when at least about 1% more, e.g., at least about 2% more, at least about 5% more, at least about 7% more, at least about 10% more, at least about 12% more, at least about 15% more, at least about 20% more, at least about 25% more, at least about 30% more, at least about 35% more, at least about 40% more, at least about 45% more, at least about 50% more, at least about 55% more, at least about 60% more, at least about 65% more, at least about 70% more, at least about 75% more, at least about 80% more, at least about 85% more, at least about 90% more, at least about 95% more, or at least 99% more by weight of one type of cellulose (e.g., type-II cellulose) is hydrolyzed than another type of cellulose (e.g., type-I cellulose), relative to the respective weight of each cellulose type (i.e., type-I and type-II) prior to the hydrolysis (e.g., the total amount by weight of type-II cellulose and type-I cellulose that is hydrolyzed). For example, if a cellulose product initially contains 50 g of type-I cellulose and 20 g of type-II cellulose, and after hydrolysis 20 g of type-I cellulose has been hydrolyzed (i.e., 40 wt. % of original type-I hydrolyzed) and 10 g of type-II cellulose has been hydrolyzed (i.e., 50 wt. % of original type-II hydrolyzed), then the type-II cellulose has been selectively hydrolyzed over the type-I cellulose, since 10% more type-II cellulose was hydrolyzed than type-I cellulose, relative to the respective weight of each cellulose type (i.e., type-I and type-II) in the cellulose product prior to the hydrolysis.

In certain embodiments, the method disclosed herein further comprises recovering at least a portion of the unconverted type-I cellulose remaining after the hydrolyzing. As used herein, "recovering" does not include collecting the unconverted type-I cellulose for the purpose of disposal. In further embodiments, the recovered unconverted type-I cellulose may be utilized in additional processes or manufacturing, for example, incorporation into a pharmaceutical composition. In some embodiments, the cellulose product formed by the method disclosed herein may be used as a rheology modifier.

In some embodiments, the cellulose product is used as a rheology modifier. In some embodiments, the cellulosic solids exiting the near-critical or supercritical hydrolysis process are used as a rheology modifier. The cellulosic solids exiting the near-critical or supercritical process can be separated from the lignin as described elsewhere herein (e.g., filter press, squeeze press, hydrocyclone, centrifuge, etc., or any combination thereof). The rheological modification of a slurry upon the addition of cellulosic solids separated from the stream exiting the near-critical or supercritical reactor can be described in terms of the increase in solids content that can be achieved by the addition of these cellulosic solids. For example, addition of these cellulosic solids to a slurry of raw biomass allows the solids content of the slurry to increase without a substantial change in slurry viscosity. For example, increasing the solids content of a slurry of raw biomass from about 17 wt. % to about 19.5 wt. % results in approximately a doubling in the slurry viscosity. However, by combining these separated cellulosic solids with the raw biomass slurry in an amount of about 35 wt. % separated cellulosic solids to about 65 wt. % raw biomass, on a dry basis, a slurry of this mixture prepared at a solids content of 19.5 wt. % has substantially the same viscosity as a slurry of raw biomass at about 17 wt. % (all dry basis). Accordingly, in view of the above description, in some embodiments the solids content (%, dry basis) of the slurry can be increased by 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 0.2.5, 2.6, 2.7, 2.8, 2.9, 3, 3.1, 3.2, 3.3, 3.4, 3.5, 3.6, 3.7, 3.8, 3.9, 4, 4.2, 4.4, 4.6, 4.8, 5, 5.2, 5.4, 5.6, 5.8, 6, 6.2, 6.4, 6.6, 6.8, 7, 7.2, 7.4, 7.6, 7.8, 8, 8.2, 8.4, 8.6, 8.8, 9, 9.2, 9.4, 9.6, 9.8, 10, 10.5, 11, 11.5, 12, 12.5, 13, 13.5, 14, 14.5, or 15% by the addition of separated cellulosic solids, while still achieving substantially the same viscosity of the raw biomass slurry at the lower solids content and before any cellulosic solids addition. The exact viscosity measurement technique is not particularly important, provided that the measurement technique is the same when comparing the viscosity of the raw biomass slurry with the viscosity of the slurry that is a mixture of separated cellulosic solids and raw biomass.

The solids content of the slurry that is processed using near-critical or supercritical water is not particularly limited. For example, the solids content (%, on a dry basis) can be 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40. Each of the foregoing numbers can be preceded by the word "about," "at least about," or "less than about," and any of the foregoing numbers can be used singly to describe an open-ended range or in combination to describe a close-ended range. These solids contents can refer to the slurry prior to any addition of cellulose product or cellulosic solids from a recycle loop, or these solids contents can refer to the slurry after addition of cellulose product or cellulosic solids from a recycle loop (as discussed elsewhere herein).

In some embodiments, the method further comprises collecting and hydrolyzing the cellulose product. In other embodiments, the method further comprises employing the cellulose product as at least a portion of the feedstock in the same or a different process. In some embodiments, the method further comprises employing the cellulose product as at least a portion of the feedstock in the same or a different process and repeating the method at least one time, for example, as part of a recycle loop. For example, a recycle loop can be employed that recycles the unconverted type-I cellulose, the formed type-II cellulose, or both, to combine with fresh cellulosic feedstock (e.g., raw biomass) in the same process or in a different process. In this case, the recycled cellulose mixed with the fresh cellulosic feedstock, and the combined mixture is processed through the same or a different process (e.g., near-critical or supercritical hydrolysis). The cellulose product or cellulosic solids from the process can recycled in any suitable manner, including a continuous loop or a semi-continuous loop. The cellulose product or cellulose solids may also be collected separately, and then added as needed to the initial feedstock to make up the slurry for near-critical or supercritical processing.

Figure 16:
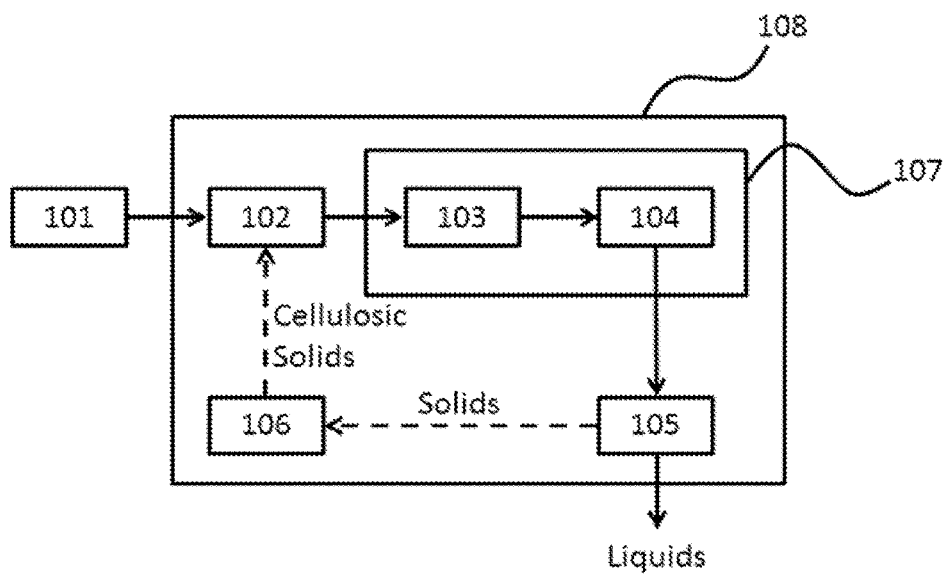
FIG. 16 shows a diagram of an embodiment of the invention showing a recycle loop (see examples).

FIG. 16 is a simplified diagram of the supercritical hydrolysis process that employs a recycle loop. Feedstock 101 that is either size-reduced raw biomass (i.e., a substantial amount of hemicellulose has not been extracted), size-reduced biomass that has already been subjected to conditions that remove hemicellulose (e.g., digestion, subcritical water extraction, near critical water extraction, supercritical water extraction, etc.), or a combination thereof, is added to feed tank 102. In feed tank 102, the biomass is combined with water to form a slurry. Other additives can be added at this or another stage, if desired. The slurry is then pumped to near-critical or supercritical reactor 103, where the slurry is either contacted with supercritical water or brought to supercritical conditions by another manner (e.g., heating coils, etc). The slurry is then held at reaction conditions for a given residence time, in which the polysaccharides present in the biomass hydrolyze to shorter chain polymers, as well as oligomers and monomers. The reaction mixture is then fed to cooling step 104, which can be flash cooling, a cool water quench, a heat exchanger, etc. The cooled slurry can then be subjected to one or more separation steps 105 and 106, in which the unreacted or incompletely reacted solid cellulosic material is separated from lignin solids. The separation step can employ one or more of, e.g., a squeeze press, hydrocyclone, centrifuge, or any other known separation technique or apparatus. In some embodiments, water or another suitable fluid can be added to the separated solids to enable transportation (e.g., pumping) and further separation. The cellulosic solids are then combined with fresh feedstock 101 in feed tank 102, the mixture re-slurried with water if necessary, and the slurry, which now contains recycled cellulosic solids as well as fresh feedstock, is fed to near-critical or supercritical hydrolysis reactor 103 to repeat the process. If water is added in a previous step (e.g., between 105 and 106) to assist in transportation, further separation, or both, then a sufficient amount of water may already be present and little to no additional water needs to be added to the feed tank). In some embodiments, the recycled solids are not combined with fresh feedstock, but may be recycled to the same or a different supercritical hydrolysis reactor on its own (i.e., without the addition of fresh feedstock).

The cellulosic solids that are recycled to the same or different process can be combined with fresh biomass in any suitable amount. For example, the amount of recycled cellulosic solids, relative to the raw biomass, all on a dry weight basis, can be 1%, 2%, 4%, 6%, 8%, 10%, 12%, 14%, 16%, 18%, 20%, 22%, 24%, 26%, 28%, 30%, 32%, 34%, 35% 36%, 38%, 40%, 42%, 44%, 46%, 48%, 50%, 52%, 54%, 56%, 58%, 60%, 62%, 64%, 66%, 68%, 70%, 72%, 74%, 76%, 78%, 80%, 82%, 84%, 86%, 88%, or 90%. Each of the foregoing numbers can be preceded by the word "about," "at least about," or "less than about," and any of the foregoing numbers can be used singly to describe an open-ended range or in combination to describe a close-ended range.

In certain embodiments, and as readily understood by one of ordinary skill in the art, the methods described herein may be performed in any reactor known in the art that is capable of withstanding the method's conditions. For example, and without limitation, the reactor may comprise one vessel. In some embodiments, the reactor may comprise more than one vessel. When multiple vessels are employed as the reactor, the vessels may be connected in a series or in parallel. In some embodiments, the vessels may be connected to allow the reactant to flow against the flow of the fluid it contacts (i.e., countercurrent flow). In other embodiments, the vessels may be connected to allow the mixture to flow in parallel with the flow of the fluid it contacts (i.e., co-current flow). The reactor comprises any possible configurations known in the art and it also may allow in situ separation of solids and liquid. In some embodiments, the separation comprises gravity separation, filter press, centrifugal separation, or any combination thereof.

In certain embodiments, the invention is directed to a method comprising: providing a reactant comprising a material selected from the group consisting of lignocellulosic biomass, cellulosic biomass, processed cellulosic biomass, municipal waste, and combinations thereof; contacting the reactant with a fluid comprising water, wherein the water is sub-critical, near-critical, or supercritical water, to form a first reactant mixture, wherein the first reactant mixture is at a fifth temperature and at a fifth pressure, and maintaining the first reactant mixture at the fifth temperature and the fifth pressure for a fifth period of time; quenching the first reactant mixture to form a first product mixture comprising: i) a first liquid fraction; and ii) a first solid fraction; wherein the first solid fraction comprises a composition comprising a cellulose product; and processing the first product mixture; wherein the processing is at least one of: a) recovering at least a portion of the cellulose product from the first product mixture to form a recovered cellulose product, wherein a yield of the recovered cellulose product is from about 5% to about 100%, based on the amount of cellulose in the reactant; and b) hydrolyzing at least a portion of the first product mixture. In some aspects, the reactant is in the form of a slurry.

In certain embodiments, the processing described herein is recovering at least a portion of the cellulose product to form a recovered cellulose product. In one embodiment, the processing further comprises using at least a portion of the recovered cellulose product as at least a portion of the reactant. In another embodiment, the processing is hydrolyzing at least a portion of the first product mixture, and the hydrolyzing is selected from the group consisting of acid hydrolysis, enzyme hydrolysis, thermal hydrolysis, and any combination thereof, thereby forming a second product mixture comprising at least one hydrolysis product.

In one embodiment the yield (wt. %, dry basis) of the recovered cellulose product, based on the amount of cellulose in the reactant, can be 5, 7, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96, 98, or 99. Each of the foregoing numbers can be preceded by the word "about," "at least about," or "less than about," and any of the foregoing numbers can be used singly to describe an open-ended range or in combination to describe a close-ended range. The yield can be any value bounded by the foregoing endpoints, or can be an open-ended range. For example, the yield can be at least about 10%, about 20% to about 66%, or less than about 82%.

In some embodiments, at least one of conditions (1)-(4): (1) the cellulose product comprises a type-I cellulose and type-II cellulose; (2) the cellulose product comprises type-II cellulose and does not comprise type-I cellulose, (3) the cellulose product has a weight-average molecular weight of about 3,000 g/mol to about 25,000 g/mol as determined on a sample of the cellulose product that has been prepared for gel-permeation chromatography analysis according to a first condition; and (4) cellulose in the cellulose product has a carbonyl content of at least about 60 µmol/g, as determined on a sample of the cellulose product that has been prepared for gel-permeation chromatography analysis according to a second condition. In one embodiment, the cellulose product comprises a type-I cellulose (e.g., unconverted type-I cellulose). In another embodiment, the cellulose product comprises a type-II cellulose. In yet another embodiment, the cellulose product comprises a type-I cellulose (e.g., unconverted type-I cellulose) and a type-II cellulose.

The fifth temperature can be any of the temperatures described hereinabove for the converting. The fifth pressure can be any of the pressures described hereinabove for the converting. The fifth time period can be any of the residence times described herein for the converting. In one embodiment, for example and without limitation, the fifth temperature can be about 250° C. to about 450° C. In other embodiments, for example, and without limitation, the fifth pressure can be about 110 bar to about 350 bar. In yet further embodiments, for example, and without limitation, the fifth time period is at least about 0.01 to about 10 seconds.

In some embodiments, the quenching comprises cooling to a temperature (° C.) of 30, 40, 50, 60, 70, 80, 90, 100, 110, 120, 130, 140, 150, 160, 170, 180, 190, 200, 210, 220, 230, 240, 250, 260, 270, 280, 290, or 300. Each of the foregoing numbers can be preceded by the word "about," "at least about," or "less than about," and any of the foregoing numbers can be used singly to describe an open-ended range or in combination to describe a close-ended range. For example, the temperature can be at least about 90° C., about 30° C. to about 180° C., or less than about 250° C. In some embodiments, the quenching comprises flash cooling.

In another embodiment, the quenching comprises changing the fifth pressure to a pressure (bar) of 1, 5, 10, 15, 20, 25, 30, 35, 40, 45, 50, 55, 60, 65, 70, 75, 80, 85, 90, 95, or 100. Each of the foregoing numbers can be preceded by the word "about," "at least about," or "less than about," and any of the foregoing numbers can be used singly to describe an open-ended range or in combination to describe a close-ended range. For example, the fifth pressure can be changed to a pressure of at least about 10 bar, about 15 bar to about 60 bar, or less than about 40 bar.

In some embodiments, the composition comprises lignin. In some embodiments, the composition comprises at least one cello-saccharide selected from a group consisting of one or more of cellohexaose, cellopentaose, celloteraose, cellotriose, cellobiose, glucose, and any combination thereof.

In some embodiments, the first liquid fraction formed by the methods described herein comprises a soluble glucose monomer, soluble glucose oligomer, soluble xylose, or any combination thereof. In some embodiments, the "solubility" is relative to water or aqueous solvents.

In one embodiment, the composition formed by the methods described herein is separated from the first liquid fraction, the first solid fraction, or a combination thereof to form a separated composition by any suitable technique, e.g., filter press, centrifugation, gravity separation, hydrocyclone, and so on. In certain embodiments, the method further comprises collecting the separated composition to form a collected composition. In some embodiments, the method further comprises washing the collected composition with a solvent to form a liquid wash fraction and a washed solid fraction. In certain embodiments, the solvent is selected from the group consisting of water, a C1-C5 alcohol, dioxane, aqueous dioxane, aqueous alkaline solution, aqueous alkaline dioxane, and any combination thereof. In one embodiment, the aqueous dioxane solution can comprise any ratio of dioxane to water. For example, the aqueous dioxane solution comprises about 4% of water in dioxane by volume, based on the total volume of the solution. In one embodiment, the aqueous alkaline solution comprises a solution of sodium hydroxide (NaOH) in water, a solution of potassium hydroxide (KOH) in water, a solution of lithium hydroxide (LiOH) in water, or any combination thereof. The amount of alkaline in the aqueous alkaline solution is not particularly limited, but typically may be about 1% by weight. In some embodiments, an aqueous alkaline dioxane solution comprises about 4% of water in dioxane by volume, based on the total volume of the solution, and about 1% hydroxide (e.g., NaOH, LiOH, and/or KOH) by weight, based on the total weight of the solution. In some embodiments, the aqueous alkaline solution is any concentration sufficient to wash the collected composition without significantly altering its chemical and physical properties.

In certain embodiments, the method described herein further comprises separating the lignin from the first solid fraction at a temperature, a pressure, and for a period of time sufficient to form a purified lignin. In one embodiment, the temperature (° C.) can be 120, 130, 140, 150, 160, 170, 180, 190, 200, 210, 220, 230, 240, 250, 260, 270, 280, 290, or 300. Each of the foregoing numbers can be preceded by the word "about," "at least about," or "less than about," and any of the foregoing numbers can be used singly to describe an open-ended range or in combination to describe a close-ended range. In another embodiment, the temperature at which the lignin is separated can be higher than a glass transition temperature of lignin. In yet another embodiment, the glass transition temperature of lignin can be at least about 65° C.

In some embodiments, the period of time (sec) sufficient to form a purified lignin can be 1, 5, 10, 20, 30, 40, 50, or 60. In some embodiments, the period of time (min) sufficient to form a purified lignin can be 1, 10, 20, 30, 40, 50, 60, 70, 72, 80, 84, 90, 96, 100, 108, 110, or 120. Each of the foregoing numbers (in sec or min) can be preceded by the word "about," "at least about," or "less than about," and any of the foregoing numbers can be used singly to describe an open-ended range or in combination to describe a close-ended range. For example, the period of time can be at least about 50 sec, about 10 min to about 96 min, or less than about 60 min.

In one embodiment, the lignin may be in a molten state. In another embodiment, the lignin may be in a softened state. In another embodiment, the method further comprises separating the purified lignin from the cellulose product. In one embodiment, the purified lignin has a higher surface tension than the cellulose product. In one embodiment, the cellulose product migrates to a surface of the purified lignin. In yet another embodiment, the purified lignin is in a form of a continuous fluid. In still another embodiment, the purified lignin is in a form of a plug. In one aspect, the purified lignin is at least about 90% pure, where the maximum purity is not particularly limited. In another aspect, the purified lignin can be about 100% pure or less, where the minimum purity is not particularly limited. For example, the purified lignin can be at least about 90% pure, e.g., at least about 91% pure, at least about 92% pure, at least about 93% pure, at least about 94% pure, at least about 95% pure, at least about 96% pure, at least about 97% pure, at least about 98% pure, at least about 99% pure, or about 100% pure. Alternatively, or in addition, the purified lignin can be about 100% pure or less, e.g., less than about 99% pure, less than about 98% pure, less than about 97% pure, less than about 96% pure, less than about 95% pure, less than about 94% pure, less than about 93% pure, less than about 92% pure, or less than about 91% pure. The purity of lignin can be bounded by any two of the foregoing endpoints, or can be an open-ended range. For example, the purity of lignin can be at least about 97% pure, about 92% to about 98% pure, or less than about 93% pure.

In certain embodiments, the reactant can be prepared by a process comprising: contacting the feedstock with water, wherein the water is supercritical water, near-critical water, or sub-critical water at a temperature, at a pressure, and for a period of time. The temperature (° C.) can be 130, 140, 150, 160, 170, 180, 190, 200, 220, 240, 260, 280, or 300. The pressure (bar) can be 2, 10, 20, 30, 40, 50, 60, 70, 80, 90, 100, 120, 140, 160, 180, 200, 220, 240, 260, 280, or 300. The time (sec) can be 0.1, 0.5, 1, 2, 5, 10, 20, 30, 40, 50, or 60. The time (min) also can be 1, 1.5, 2, 2.5, 3, 3.5, 4, 4.5, 5, 10, 20, 30, 40, 50, 60, 70, 80, 90, 100, 110, 120, 130, 140, or 150. Each of the foregoing numbers (for temperature, pressure, or time) can be preceded by the word "about," "at least about," or "less than about," and any of the foregoing numbers can be used singly to describe an open-ended range or in combination to describe a close-ended range.

In some embodiments, the liquid wash fraction comprises at least one material selected from the group consisting of a soluble oligosaccharide, a soluble monosaccharide, soluble lignin, a soluble degradation product, a soluble reaction byproduct, and any combination thereof. In one embodiment, the degradation product is hydroxymethylfurfural, glycolaldehyde, glyceraldehyde, formic acid, levulinic acid, lactic acid, pyruvaldehyde, dihydroxyacetone, furfural, formaldehyde, glucuronic acid, furan, or any combination thereof. In a yet further embodiment, a soluble reaction byproduct is acetic acid.

In one embodiment, the washed solid fraction comprises a material selected from the group consisting of an insoluble cellulose material, an insoluble cello-oligosaccharide, an insoluble lignin, and any combination thereof.

In one embodiment, at least a portion of the recovered cellulose product is hydrolyzed by acid hydrolysis, enzyme hydrolysis, heat hydrolysis, or any combination thereof. In another embodiment, the hydrolyzing is acid hydrolysis. In some embodiments, the acid hydrolysis is performed at a pH of 0, 0.5, 1, 1.5, 2, 2.5, 3, 3.5, or 4. Each of the foregoing numbers can be preceded by the word "about," "at least about," or "less than about," and any of the foregoing numbers can be used singly to describe an open-ended range or in combination to describe a close-ended range.

In one embodiment, substantially no pH increasing additive is added to the product stream. In another embodiment, the product stream can have any conductivity as disclosed elsewhere herein.

In certain embodiments, the hydrolyzing is thermal hydrolysis, and the hydrolyzing comprises bringing the first product mixture to a sixth temperature and a sixth pressure; and maintaining the first product mixture at the sixth temperature and the sixth pressure for a sixth time period, thereby forming the second product mixture comprising the at least one hydrolysis product. The sixth temperature, sixth pressure, and six time period can be the same as the conditions disclosed hereinabove for the hydrolyzing. In some embodiments, the at least one hydrolysis product is a glucose oligomer, a glucose monomer, or a combination thereof.

In some embodiments, the cellulose product, or a portion thereof (e.g., the cellulose portion), can be incorporated into an adhesive. In some embodiments, the adhesive includes a phenolic resin, a phenol-formaldehyde resin, a urea-formaldehyde resin, or combinations thereof. Phenol-formaldehyde (PF) resins are commonly used adhesives in engineered wood products, including plywood and oriented strand board (OSB), because of their weather and water resistance, making them suitable for exterior, as well as interior, applications.

In some embodiments, the cellulose product or a portion thereof can be incorporated into an adhesive in combination with lignin. In some embodiments, the cellulose product (or portion thereof) and lignin are incorporated separately into an adhesive. In some embodiments, the cellulose product and lignin are present as a mixture and are added to an adhesive as the mixture. In some embodiments, the cellulose product is present in a residue along with lignin resulting from biomass processing (e.g., using hot compressed water, supercritical water, acid hydrolysis, enzymatic hydrolysis, or any combination thereof). In some embodiments, the cellulose product is first separated from this residue (e.g., separated from lignin) prior to incorporating the cellulose product (or a portion thereof) into an adhesive. In some embodiments, the cellulose product is not separated from the residue containing lignin prior to incorporation of the residue into an adhesive. In some embodiments, both cellulose product (or a portion thereof) and residue can be added to an adhesive.

The cellulose product (or a portion thereof), the residue containing cellulose, or a combination thereof can be added to an adhesive in two different ways: (1) before "cooking" an adhesive to form a resin, or (2) after "cooking" (i.e., added after the resin has been formed by cooking). Combinations of (1) and (2) are also possible.

Condensation products of the reaction of a phenol and formaldehyde can be either potentially thermosetting (as known as "resols") or thermoplastic (also known as "novolaks"). A resol is formed when formaldehyde is used in molar excess under (normally) alkaline conditions, while a novolak is formed when phenol is used in molar excess under (normally) acid conditions. By reacting with sufficient additional formaldehyde under alkaline conditions, it is possible to convert a novolak to a resol. A two-stage resol prepared in this way differ in certain physical properties, such as intrinsic viscosity, from a resol made by direct reaction of phenol and formaldehyde under alkaline conditions. PF resins of the resol type are produced by condensation of monomeric phenol and formaldehyde, typically at 80-95° C. in the presence of NaOH to produce polymeric PF resin, which then may be used as adhesive for production of various engineered wood products. When preparing engineered wood products, adhesive and wood can be pressed together under heating ("hot press") in order to create the engineered wood product.

The amount (wt. %, dry basis) of cellulose product (or a portion thereof) in an adhesive can be 1, 2, 4, 6, 8, 10, 12, 14, 16, 18, 20, 22, 24, 26, 28, 30, 32, 34, 36, 38, 40, 42, 44, 46, 48, or 50. Each of the foregoing numbers can be preceded by the word "about," "at least about," or "less than about," and any of the foregoing numbers can be used singly to describe an open-ended range or in combination to describe a close-ended range.

In embodiments where the cellulose product is incorporated into an adhesive without first being separated from the residue containing lignin (resulting from processing/hydrolysis of lignocelluloseic biomass), the amount (wt. %, dry basis) of cellulose product in the residue can be 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, or 80. Each of the foregoing numbers can be preceded by the word "about," "at least about," or "less than about," and any of the foregoing numbers can be used singly to describe an open-ended range or in combination to describe a close-ended range. The remaining portion of the residue typically substantially comprises lignin. Thus, the amount of lignin in the residue containing both lignin and cellulose product can be calculated by subtracting any of the foregoing percentages from 100%. For example, if the residue contains about 30 wt. % cellulose product, then the lignin will be present in an amount of about 70 wt. %.

In embodiments where the cellulose product is incorporated into an adhesive without first being separated from the residue containing lignin (resulting from processing/hydrolysis of lignocellulosic biomass), the amount (wt. %, dry basis) of residue in the adhesive can be 1, 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, or 80. Each of the foregoing numbers can be preceded by the word "about," "at least about," or "less than about," and any of the foregoing numbers can be used singly to describe an open-ended range or in combination to describe a close-ended range.

In some embodiments, additional cellulose product (or a portion thereof) can be combined with biomass hydrolysis residue (already containing both cellulose product and lignin), as a way to increase the total amount of cellulose product present in the adhesive. The additional (wt. %, dry basis) cellulose product can be 1, 2, 4, 6, 8, 10, 12, 14, 16, 18, 20, 22, 24, 26, 28, 30, 32, 34, 36, 38, 40, 42, 44, 46, 48, 50, 55, 60, 65, 70, 75, 80, 85, 90, 95, 100, 110, 120, 130, 140, 150, 160, 170, 180, 190, or 200 based on the total weight of the residue added to the adhesive on a dry basis (the foregoing numbers do not include that amount of cellulose product already present in the residue itself. Each of the foregoing numbers can be preceded by the word "about," "at least about," or "less than about," and any of the foregoing numbers can be used singly to describe an open-ended range or in combination to describe a close-ended range.

Some embodiments disclosed herein are set forth in the following clauses, and any combination of these clauses (or portions thereof) may be made to define an embodiment.

Clause 1: A composition, comprising: a cellulose product in an amount about 45% by weight to about 100% by weight, based on the total weight of the composition on a dry basis, wherein the cellulose product comprises a type-II cellulose, wherein the cellulose product comprises cellulose having a weight-average molecular weight of about 3,000 g/mol to about 25,000 g/mol as determined on a sample of the cellulose product that has been prepared for gel-permeation chromatography analysis according to a first condition.

Clause 2: The composition of clause 1, wherein about 100% by weight, based on the total weight of the cellulose product on a dry basis, of cellulose in the cellulose product has a weight-average molecular weight of about 3,000 g/mol to about 25,000 g/mol as determined on a sample of the cellulose product that has been prepared for gel-permeation chromatography analysis according to a first condition.

Clause 3: The composition of clause 2, wherein at least about 80% by weight, based on the total weight of the cellulose product on a dry basis, of cellulose in the cellulose product has a weight-average molecular weight of about 5,000 g/mol to about 18,000 g/mol as determined on a sample of the cellulose product that has been prepared for gel-permeation chromatography analysis according to a first condition.

Clause 4: The composition of clause 2, wherein at least about 92% by weight, based on the total weight of the cellulose product on a dry basis, of cellulose in the cellulose product has a weight-average molecular weight of about 7,000 g/mol to about 15,000 g/mol as determined on a sample of the cellulose product that has been prepared for gel-permeation chromatography analysis according to a first condition.

Clause 5: The composition of clause 1, wherein at least about 80% by weight, based on the total weight of the cellulose product on a dry basis, of cellulose in the cellulose product has a weight-average molecular weight of about 3,000 g/mol to about 12,000 g/mol as determined on a sample of the cellulose product that has been prepared for gel-permeation chromatography analysis according to a first condition.

Clause 6: The composition of any one of clauses 1-5, wherein at least a portion of the cellulose product exhibits a crystallinity of at least about 70%.

Clause 7: The composition of any one of clauses 1-6, wherein at least a portion of the cellulose product is in a form of microcrystalline cellulose, nanocellulose, or a combination thereof.

Clause 8: The composition of any one of clauses 1-7, wherein the cellulose product is substantially in the form of microcrystalline cellulose.

Clause 9: The composition of any one of clauses 1-8, wherein the cellulose product has a particle size of about 10 nm to about 500 nm.

Clause 10: The composition of any one of clauses 1-9, wherein the cellulose product is in a form of at least one of nanosize spheres and self-assembled short cellulose rods.

Clause 11: The composition of any one of clauses 1-10, wherein the cellulose product has a particle size distribution with a D10 of about 0.4 µm to about 35 µm.

Clause 12: The composition of any one of clauses 1-11, wherein the cellulose product has a particle size distribution with a D50 of about 5 µm to about 200 µm.

Clause 13: The composition of any one of clauses 1-12, wherein the cellulose product has a particle size distribution with a D90 of about 40 µm to about 600 µm.

Clause 14: The composition of any one of clauses 1-13, wherein the cellulose product has a median pore diameter of about 10 µm to about 100 µm, when the cellulose product is compressed to form a compact.

Clause 15: The composition of any one of clauses 1-14, wherein the cellulose product has a moisture content of less than about 5% by weight, based on the weight of the dry cellulose product.

Clause 16: The composition of any one of clauses 1-15, wherein the cellulose product has a loose bulk density of about 0.15 g/ml to about 0.5 g/ml.

Clause 17: The composition of any one of clauses 1-16, wherein the cellulose product has a loss on drying less than about 10% by weight, based on the weight of the dry cellulose product.

Clause 18: The composition of any one of clauses 1-17, wherein the cellulose product comprises less than about 0.3% by weight of water-soluble substances, based on the total weight of the cellulose product on a dry basis.

Clause 19: The composition of any one of clauses 1-18, wherein the cellulose product comprises heavy metals in an amount of less than about 10 ppm, based on the total weight of the cellulose product on a dry basis.

Clause 20: The composition of any one of clauses 1-19, wherein the cellulose product exhibits conductivity less than about 80 µS/cm.

Clause 21: The composition of any one of clauses 1-20, further comprising an alcohol-soluble fraction.

Clause 22: The composition of clause 21, wherein the alcohol-soluble fraction comprises lignin in an amount of about 0% by weight to about 30% by weight, based on the total weight of the composition on a dry basis.

Clause 23: The composition of clause 22, wherein the lignin has a weight-average molecular weight of about 1,000 g/mol to about 2,500 g/mol.

Clause 24: The composition of any one of clauses 1-23, further comprising a water-soluble fraction.

Clause 25: The composition of clause 24, wherein the water-soluble fraction comprises at least one cello-oligosaccharide.

The Clause 26: composition of clause 25, wherein the at least one cello-oligosaccharide has a weight-average molecular weight of about 200 g/mol to about 1,500 g/mol.

Clause 27: The composition of clause 25 or clause 26, wherein the at least one cello-oligosaccharide comprises at least one compound selected from the group consisting of cellohexaose, cellopentaose, celloteraose, cellotriose, cellobiose, glucose, and any combination thereof.

Clause 28: The composition of any one of clauses 1-27, further comprising a degradation product.

Clause 29: The composition of any one of clauses 1-28, further comprising a C5 saccharide in an amount about 0% by weight to about 5% by weight, based on the total weight of the composition on a dry basis, wherein the C5 saccharide is selected from the group consisting of xylose, xylan, and a combination thereof.

Clause 30: The composition of any one of clauses 1-29, further comprising insoluble species in an amount about 0% by weight to about 8% by weight, based on the total weight of the composition on a dry basis.

Clause 31: The composition of any one of clauses 1-30, further comprising a dispersing agent.

Clause 32: The composition of clause 31, wherein the composition is an admixture.

Clause 33: The composition of clause 31, wherein the dispersing agent is selected from the group consisting of carboxymethylcellulose, paraben derivatives, and combinations thereof.

Clause 34: The composition of clause 33, wherein a weight ratio of the cellulose product and the carboxymethylcellulose is about 95:5 to about 70:30.

Clause 35: The composition of claim 1, further comprising at least one pharmaceutically active ingredient.

Clause 36: The composition of clause 35, wherein the cellulose product serves as a carrier material, a spheronizing agent, a topical drug delivery material, an excipient, or any combination thereof.

Clause 37: The composition of any one of clauses 1-36, wherein the first condition consists of or consists essentially of the following sequential steps: (i) swelling the cellulose product twice in DI water for 1 hour each while stirring at room temperature (filter and re-suspend solids in fresh DI water after each swelling), (ii) activating the resulting solids twice in methanol for 45 minutes each at room temperature while stirring (filter and re-suspend solids in fresh methanol after each activating), (iii) activating the resulting solids in N,N-Dimethylacetamide (DMAc) (without LiCl) overnight at room temperature with stirring (followed by filtration of solids), (iv) stirring the resulting solids in 8% by weight LiCl in DMAc for 24 hours at room temperature, followed by (v) subjecting the same LiCl/DMAc mixture (without any filtration) at 2-8° C. for up to 3 days without stirring Clause 38: The composition of any one of clauses 1-37, wherein the cellulose product has an $M_w$ that is less than about 0.5 times the value of the MCC $M_w$.

Clause 39: An adhesive composition comprising the composition of any one of clauses 1-38.

Clause 40: The adhesive composition of clause 39, wherein the adhesive composition comprises at least one of a phenol-formaldehyde resin and a urea-formaldehyde resin.

Clause 41: The adhesive composition of clause 39 or clause 40, further comprising lignin.

Clause 42: The adhesive composition of clause 41, wherein the cellulose product and lignin were incorporated into the adhesive composition as a residue derived from biomass hydrolysis.

Clause 43: The adhesive composition of clause 42, wherein the biomass hydrolysis is selected from the group consisting of supercritical fluid hydrolysis, sub-critical fluid hydrolysis, near-critical fluid hydrolysis, acid hydrolysis, enzymatic hydrolysis, and combinations thereof.

Clause 44: The adhesive composition of clause 42 or clause 43, wherein the amount of residue incorporated into the adhesive is at least about 1 wt. %, based on the total weight of the adhesive on a dry basis.

Clause 45: The adhesive composition of clause 44, wherein the residue contains at least about 1 wt. % of the cellulose product, based on the total weight of the residue on a dry basis.

Clause 46: The adhesive composition of any one of clauses 39-45, wherein the composition consists essentially of the cellulose product.

Clause 47: The adhesive composition of any one of clauses 39-46, wherein the adhesive composition contains at least about 1 wt. % of the cellulose product.

Clause 48: A method comprising: providing a feedstock comprising a type-I cellulose; converting at least a portion of the type-I cellulose to a type-II cellulose; and hydrolyzing at least a portion of the type-II cellulose.

Clause 49: The method of clause 48, wherein the feedstock is selected from the group consisting of lignocellulosic biomass, cellulosic biomass, processed cellulosic biomass, municipal solid waste, and any combination thereof.

Clause 50: The method of clause 48 or clause 49, wherein the converting comprises contacting the feedstock with a fluid comprising supercritical water.

Clause 51: The method of any one of clauses 48-50, wherein the converting is carried out at a temperature of about 150° C. to about 450° C.

Clause 52: The method of any one of clauses 48-51, wherein the converting produces a composition comprising a cellulose product, wherein the cellulose product comprises an unconverted type-I cellulose and the type-II cellulose.

Clause 53: The method of clause 52, wherein at least one of conditions (1)-(4) is satisfied: (1) the cellulose product comprises a type-I cellulose and type-II cellulose; (2) the cellulose product comprises type-II cellulose and does not comprise type-I cellulose, (3) the cellulose product has a weight-average molecular weight of about 3,000 g/mol to about 25,000 g/mol as determined on a sample of the cellulose product that has been prepared for gel-permeation chromatography analysis according to a first condition; and (4) cellulose in the cellulose product has a carbonyl content of at least about 60 µmol/g, as determined on a sample of the cellulose product that has been prepared for gel-permeation chromatography analysis according to a second condition.

Clause 54: The method of clause 52 or clause 53, wherein the hydrolyzing is carried out on the composition.

Clause 55: The method of any one of clauses 52-54, wherein the composition further comprises lignin.

Clause 56: The method of clause 55, further comprising separating the lignin from the cellulose product using gravity separation, centrifugal separation, centripetal separation, filtration, or a combination thereof.

Clause 57: The method of clause 55 or clause 56, further comprising separating the lignin from the cellulose product using a hydrocyclone.

Clause 58: The method of clause 57, wherein at least a portion of the lignin is removed in an underflow of the hydrocyclone.

Clause 59: The method of clause 57 or 58, wherein at least a portion of the cellulose product is removed in an overflow of the hydrocyclone.

Clause 60: The method of any one of clauses 48-59, wherein the hydrolyzing is carried out at a lower temperature than the converting.

Clause 61: The method of any one of clauses 48-60, wherein the hydrolyzing comprises employing a fluid comprising hot compressed water.

Clause 62: The method of any one of clauses 48-61, wherein the hydrolyzing is carried out using thermal energy originating from the converting.

Clause 63: The method of any one of clauses 48-62, wherein the converting is conducted at a temperature above 100° C., and the type-II cellulose produced in the converting is maintained at a temperature above 100° C. prior to the hydrolyzing, and optionally during the hydrolyzing.

Clause 64: The method of any one of clauses 48-63, wherein the converting produces a stream at a first temperature, and the method further comprises: lowering the first temperature of the stream to a second temperature; maintaining the stream at the second temperature for a period of time, and changing the stream to a third temperature prior to the hydrolyzing; wherein the hydrolyzing is conducted at a fourth temperature that is the same as or different from the third temperature.

Clause 65: The method of any one of clauses 48-64, wherein the hydrolyzing comprises acid hydrolysis.

Clause 66: The method of clause 52, further comprising hydrolyzing the type-II cellulose, wherein the type-II cellulose is selectively hydrolyzed over the unconverted type-I cellulose.

Clause 67: The method of clause 52, further comprising recovering the unconverted type-I cellulose.

Clause 68: The method of claim 67, further comprising incorporating the recovered unconverted type-I cellulose into a pharmaceutical composition.

Clause 69: The method of any one of clauses 52-68, wherein the cellulose product is used as a rheology modifier.

Clause 70: The method of any one of clauses 52-69, further comprising employing at least a portion of the cellulose product as at least a portion of the feedstock, and repeating the method at least one time.

Clause 71: The method of any one of clauses 48-70, wherein at least a portion of the biomass is fractionated biomass.

Clause 72: The method of any one of clauses 48-71, wherein at least a portion of the cellulose product is incorporated into an adhesive selected from the group consisting of a phenolic resin, a phenol-formaldehyde resin, or a combination thereof.

Clause 73: A method comprising: providing a reactant comprising a material selected from the group consisting of lignocellulosic biomass, cellulosic biomass, processed cellulosic biomass, municipal waste, and combinations thereof; contacting the reactant with a fluid comprising water, wherein the water is sub-critical, near-critical, or supercritical water, to form a first reactant mixture, wherein the first reactant mixture is at a fifth temperature and at a fifth pressure, and maintaining the first reactant mixture at the fifth temperature, and the fifth pressure for a fifth period of time; quenching the first reactant mixture to form a first product mixture comprising: i) a first liquid fraction; and ii) a first solid fraction; wherein the first solid fraction comprises a composition comprising a cellulose product; and processing the first product mixture; wherein the processing is at least one of: a) recovering at least a portion of the cellulose product from the first product mixture to form a recovered cellulose product, wherein a yield of the recovered cellulose product is from about 5% to about 100%, based on the amount of cellulose in the reactant; and b) hydrolyzing at least a portion of the first product mixture.

Clause 74: The method of clause 73, wherein at least one of conditions (1)-(4) is satisfied: (1) the cellulose product comprises a type-I cellulose and type-II cellulose; (2) the cellulose product comprises type-II cellulose and does not comprise type-I cellulose, (3) the cellulose product has a weight-average molecular weight of about 3,000 g/mol to about 25,000 g/mol as determined on a sample of the cellulose product that has been prepared for gel-permeation chromatography analysis according to a first condition; and (4) cellulose in the cellulose product has a carbonyl content of at least about 60 µmol/g, as determined on a sample of the cellulose product that has been prepared for gel-permeation chromatography analysis according to a second condition.

Clause 75: The method of clause 73 or clause 74, wherein the cellulose product comprises a type-I cellulose.

Clause 76: The method of any one of clauses 73-75, wherein the cellulose product comprises a type-II cellulose.

Clause 77: The method of any one of clauses 73-76, wherein the cellulose product comprises a type-I cellulose and a type-II cellulose.

Clause 78: The method of any one of clauses 73-77, wherein the fifth temperature is about 250° C. to about 450° C.

Clause 79: The method of any one of clauses 73-78, wherein the fifth pressure is about 110 bar to about 350 bar.

Clause 80: The method of any one of clauses 73-79, wherein the fifth time period is about 0.01 sec to about 10 sec.

Clause 81: The method of any one of clauses 73-80, wherein the quenching comprises flash cooling.

Clause 82: The method of any one of clauses 73-81, wherein the quenching comprises cooling to a temperature of about 30° C. to about 300° C.

Clause 83: The method of any one of clauses 73-82, wherein the quenching comprises changing the fifth pressure to a pressure of about 1 to about 90 bar.

Clause 84: The method of any one of clauses 73-83, wherein the composition comprises lignin.

Clause 85: The method of any one of clauses 73-84, wherein the composition comprises at least one cello-saccharide selected from the group consisting of cellohexaose, cellopentaose, celloteraose, cellotriose, cellobiose, glucose, and combinations thereof.

Clause 86: The method of any one of clauses 73-85, wherein the first liquid fraction comprises a soluble glucose monomer, a soluble glucose oligomer, a soluble xylose monomer, a soluble xylose oligomer, or any combination thereof.

Clause 87: The method of any one of clauses 73-86, further comprising separating the composition from the first liquid fraction, the first solid fraction, or a combination thereof to form a separated composition.

Clause 88: The method of clause 87, wherein the separating is gravity separation, centrifugal separation, centripetal separation, filtration, or a combination thereof.

Clause 89: The method of clause 87 or clause 88, wherein the separating comprises use of a hydrocyclone.

Clause 90: The method of clause 89, wherein the first solid fraction further comprises lignin, and the method further comprises removing at least a portion of the lignin in an underflow of the hydrocyclone.

Clause 91: The method of clause 89 or clause 90, further comprising removing of at least a portion of the cellulose product in an overflow of the hydrocyclone.

Clause 92: The method of any one of clauses 84-91, further comprising: separating the lignin from the first solid fraction at a temperature, a pressure, and for a period of time sufficient to form a purified lignin.

Clause 93: The method of clause 92, wherein the temperature is about 120° C. to about 300° C.

Clause 94: The method of clause 92 or clause 93, wherein the temperature is higher than a glass transition temperature of lignin.

Clause 95: The method of clause 94, wherein the glass transition temperature of lignin is at least about 65° C.

Clause 96: The method of any one of clauses 92-95, wherein the period of time is about 1 second to about 2 hours.

Clause 97: The method of any one of clauses 92-96, wherein lignin is in a molten state.

Clause 98: The method of any one of clauses 92-97, further comprising separating the purified lignin from the cellulose product.

Clause 99: The method of clause 98, wherein the purified lignin has a higher surface tension than the cellulose product.

Clause 100: The method of clause 98 or clause 99, wherein the cellulose product migrates to a surface of the purified lignin.

Clause 101: The method of any one of clauses 92-100, wherein the purified lignin is in a form of a continuous fluid.

Clause 102: The method of any one of clauses 92-101, wherein the purified lignin is in a form of a plug.

Clause 103: The method of any one of clauses 92-102, wherein the purified lignin is at least about 97% pure.

Clause 104: The method of any one of clauses 92-103, wherein the purified lignin is at least about 99% pure.

Clause 105: A product formed by the method of any one of clauses 73-104.

Clause 106: The method of any one of clauses 73-104, wherein the reactant is prepared by a process comprising: contacting the feedstock with water, wherein the water is supercritical water, near-critical water, or sub-critical water at a temperature, at a pressure, and for a period of time.

Clause 107: The method of clause 106, wherein the temperature is about 130° C. to about 300° C.

Clause 108: The method of clause 106 or clause 107, wherein the pressure is about 2 bar to about 300 bar.

Clause 109: The method of any one of clauses 106-108, wherein the period of time is about 60 sec to about 150 min.

Clause 110: The method of any one of clauses 87-104, further comprising collecting the separated composition to form a collected composition.

Clause 111: The method of clause 110, further comprising washing the collected composition with a solvent to form a liquid wash fraction and a washed solid fraction.

Clause 112: The method of clause 111, wherein the solvent is selected from the group consisting water, a C1-C5 alcohol, dioxane, aqueous dioxane, aqueous alkaline solution, or any combination thereof.

Clause 113: The method of clause 111 or clause 112, wherein the liquid wash fraction comprises at least one of a soluble oligosaccharide, a soluble monosaccharide, a soluble lignin, a soluble degradation product, a soluble reaction byproduct, or any combination thereof.

Clause 114: The method of clause 113, wherein the soluble degradation product is hydroxymethylfurfural, glycolaldehyde, glyceraldehyde, formic acid, levulinic acid, lactic acid, pyruvaldehyde, dihydroxyacetone, furfural, formaldehyde, glucuronic acid, furan, or any combination thereof.

Clause 115: The method of clause 113 or clause 114, wherein the soluble reaction byproduct is acetic acid.

Clause 116: The method of any one of clauses 111-115, wherein the washed solid fraction comprises a material selected from the group consisting of an insoluble cellulose material, an insoluble cello-oligosaccharide, an insoluble lignin, and combinations thereof.

Clause 117: The method of any one of clauses 73-104 and 106-116, wherein the processing is recovering at least a portion of the cellulose product to form a recovered cellulose product.

Clause 118: The method of clause 117, further comprising using at least a portion of the recovered cellulose product as at least a portion of the reactant.

Clause 119: The method of any one of clauses 73-104 and 106-118, wherein the processing is hydrolyzing at least a portion of the first product mixture, and the hydrolyzing is selected from the group consisting of acid hydrolysis, enzyme hydrolysis, thermal hydrolysis, and any combination thereof, thereby forming a second product mixture comprising at least one hydrolysis product.

Clause 120: The method of any one of clauses 117-119, wherein at least a portion of the recovered cellulose product is hydrolyzed by acid hydrolysis, enzyme hydrolysis, heat hydrolysis, or a combination thereof.

Clause 121: The method of clause 119 or clause 120, wherein the hydrolyzing is acid hydrolysis.

Clause 122: The method of clause 121, wherein the acid hydrolysis is carried out at a pH of less than about 4.

Clause 123: The method of clause 121 or clause 122, wherein substantially no pH increasing additive is added to the product stream.

Clause 124: The method of any one of clauses 121-123, wherein the product stream has conductivity of about 0.055 µOhm/cm to about 80 µOhm/cm.

Clause 125: The method of any one of clauses 73-104 and 106-124, wherein at least a portion of the first product mixture is used to form at least a portion of the reactant.

Clause 126: The method of any one of clauses 119-125, wherein the hydrolyzing is thermal hydrolysis, and the hydrolyzing comprises: bringing the first product mixture to a sixth temperature and a sixth pressure; and maintaining the first product mixture at the sixth temperature and the sixth pressure for a sixth time period, thereby forming the second product mixture comprising the at least one hydrolysis product.

Clause 127: The method of clause 126, wherein the at least one hydrolysis product is a glucose oligomer, a glucose monomer, or a combination thereof.

Clause 128: The method of clause 126 or clause 127, wherein the sixth time period is about 0.01 sec to about 10 sec.

Clause 129: The method of any one of clauses 126-128, wherein the sixth temperature is about 150° C. to about 450° C.

Clause 130: The method of any one of clauses 126-129, wherein the sixth pressure is about 1 bar to about 350 bar.

Clause 131: The method of clause 52, wherein the cellulose product has an $M_w$ that is less than about 0.5 times the value of the MCC $M_w$.

Clause 132. The composition of any one of clauses 1-46 and 52-131, wherein cellulose in the cellulose product has a carbonyl content of at least about 60 µmol/g, as determined on a sample of the cellulose product that has been prepared for gel-permeation chromatography analysis according to a second condition.

The present invention is further defined in the following Examples, in which all parts and percentages are by weight, unless otherwise stated. It should be understood that these examples, while indicating preferred embodiments of the invention, are given by way of illustration only and are not to be construed as limiting in any manner. From the above discussion and these examples, one skilled in the art can ascertain the essential characteristics of this invention, and without departing from the spirit and scope thereof, can make various changes and modifications of the invention to adapt it to various usages and conditions.

EXAMPLES

Example 1

In this example, a cellulose-rich "white layer" was formed from biomass using a two-step process. First, an aqueous slurry of comminuted biomass was subjected to a temperature of about 200-250° C. for a period of about 1-8 minutes under a pressure sufficient to keep all of the fluid in liquid form (generally less than about 50 bar). The resulting mixture was filtered, the solids re-slurried with water, and the slurry subjected to a temperature of about 350-400° C. for a period of less than about 10 sec under a pressure sufficient to keep the fluid in liquid or supercritical form (generally less than about 250 bar). The resulting mixture was centrifuged at about 4000 rpm for 10 min, and three different fractions were obtained: (i) a liquid phase containing gluco-oligosaccharides (GOS-0), and a solid fraction containing (ii) a "white layer" (WL-0) and (iii) a "dark layer" (DL-0). The WL-0 was re-dispersed in water and centrifuged again at the same conditions, thereby forming another three layers: GOS-1, WL-1, and DL-1. FIG. 1 depicts the photograph of the supercritical hydrolysis slurry after the second centrifugation. All three fractions have been separated and analyzed.

White Layer solids (WL-0 and WL-1) obtained by the sequential centrifugation were freeze-dried, and then prepared for cellulose GPC analysis. The WL-0 and WL-1 samples were exposed to the steps of cellulose dissolution (herein termed the "first condition") detailed in "Cellulose in lithium chloride/N,N-dimethylacetamide, optimization of a dissolution method using paper substrates and stability of the solutions" by A.-L. Dupont, *Polymer* 44 (2003), pp. 4117-4126, which is incorporated by reference herein in its entirety. A dn/dc value of 0.136 mL/g was used in the GPC measurements of the WL-0 and WL-1 samples reported herein.

Both WL-0 and WL-1 underwent five separate sequential steps (i.e., the "first condition") to analyze the composition of the solids. These steps were aimed to "hydrate" and "activate" long chain cellulose chains to be able to dissolve the cellulose in Lithium Chloride/N,N-dimethylacetamide (LiCl/DMAc) solution. The sequential dissolution steps involved: (i) swelling the cellulose product twice in DI water for 1 hour each while stirring at room temperature (filter and re-suspend solids in fresh DI water after each swelling), (ii) activating the resulting solids twice in methanol for 45 minutes each at room temperature while stirring (filter and re-suspend solids in fresh methanol after each activating), (iii) activating the resulting solids in N,N-Dimethylacetamide (DMAc) (without LiCl) overnight at room temperature with stirring (followed by filtration of solids), (iv) stirring the resulting solids in 8% by weight LiCl in DMAc for 24 hours at room temperature, followed by (v) subjecting the same LiCl/DMAc mixture (without any filtration) at 2-8° C. for up to 3 days without stirring. All of the steps of the first condition are performed at ambient pressure.

Substantially all of the cellulose present in the WL-0 and WL-1 layers was dissolved in step (iv), and the insoluble material was separated by the final filtration. After each filtration step the resulting solvent fractions were analyzed by different SEC/GPC techniques.

The weight percentages of all fractions are summarized in Table 1. The weight percentage of each fraction is based on the total weight of the starting WL-0 or WL-1 solids on a dry basis (i.e., without moisture).

TABLE 1

Composition of various fractions present in WL-0 and WL-1.

| Sample | WL-0, wt. % | WL-1, wt. % | Comments |
| --- | --- | --- | --- |
| Total | 100 | 100 | |
| $H_2O$-1 | 10.26 | 12.34 | Sugar Oligomers (COS) analyzed by |
| $H_2O$-2 | 1.31 | 1.02 | Agilent/Waters hydrogel SEC |
| MeOH-1 | 27.20 | 19.11 | Solubilized lignin fraction, MeOH |
| MeOH-2 | 1.32 | 1.33 | evaporated, analyzed by Agilent/PSS MCX SEC |
| DMAc | 3.95 | 3.00 | An organic fraction, sugars/lignin |
| LiCl/DMAc | 50.20 | 61.89 | Cellulose polymers analyzed by Viscotek LiCl-DMAc GPC |
| Insoluble solids | 5.76 | 1.31 | |

Example 2

This example relates to the analysis of the water-soluble fraction $H_2O$-1 from Example 1. The water-soluble fraction, containing cello-oligomers, was analyzed with an Agilent 1260 µHPLC equipped with Waters Ultrahydrogel 120, 500 and 1000 columns. All samples were prepared at the concentration of about 1 mg/ml. Pure degassed and 0.45µ filtered DI water was used as an eluent at a flow rate of 0.5 ml/min. MEGAZYME cello-oligomers were used as calibration standards for cellotriose, cellotetraose, cellopentaose, and cellohexaose. Glucose and cellobiose standards were purchased from Sigma-Aldrich. Samples were run at a temperature of 30° C. with the RI detector kept at 55° C. The SEC and GPC results were analyzed using the Cirrus extension program for ChemStation software to calculate MMD of all components.

Tables 2 and 3 demonstrate the composition of cello-oligosaccharides present in WL-0 and WL-1 water-soluble fractions. Table 4 shows the calibration data used to determine the composition of the white layers. The term "other products" refers to all other low molecular weight products present in the solution having relatively longer elution time. The "error" in Table 4 is measured as follows: each standard in the table was analyzed, the data subjected to linear regression to provide a linear equation, and the % error is the deviation of each standard from the linear equation. Glucose and glucose oligomers up to cellohexaose are summarized in the last row of Tables 2-3, and they represent about 85% of the total sample based on a peak integration basis, with a weight average molecular weight of about 650-700 g/mol.

TABLE 2

Composition of the water-soluble fraction $H_2O$-1 of WL-0 (10.26 wt. % of the total sample).

| Component | Max. RT, min | Mp | Mn | Mw | Mz | PDI | % Area |
|---|---|---|---|---|---|---|---|
| Cellohexaose and pentaose | 51.80 | 1078 | 1063 | 1124 | 1219 | 1.06 | 34.68 |
| Cellatetraose | 53.40 | 657 | 657 | 631 | 649 | 0.96 | 10.74 |
| Cellotriose | 54.41 | 479 | 476 | 467 | 478 | 0.98 | 12.37 |
| Cellobiose | 55.76 | 315 | 313 | 312 | 318 | 1.00 | 12.91 |
| Glucose | 57.56 | 179 | 160 | 167 | 175 | 1.04 | 14.71 |
| "Other products" | 60.88 | 64 | 42 | 50 | 57 | 1.19 | 7.29 |
| Peaks 2-6 (sugar-oligo) | | 1059 | 405 | 676 | 951 | 1.67 | 85.13 |

TABLE 3

Composition of the water-soluble fraction $H_2O$-1 of WL-1 (12.34 wt. % of the total sample)

| Component | Max. RT (min) | Mp | Mn | Mw | Mz | PDI | % Area |
|---|---|---|---|---|---|---|---|
| Cellohexaose and pentaose | 51.87 | 1056 | 1063 | 1117 | 1202 | 1.05 | 32.47 |
| Cellatetraose | 53.40 | 655 | 660 | 636 | 654 | 0.96 | 10.99 |
| Cellotriose | 54.42 | 478 | 476 | 467 | 478 | 0.98 | 12.19 |
| Cellobiose | 55.76 | 314 | 311 | 310 | 316 | 1.00 | 13.18 |
| Glucose | 57.58 | 178 | 153 | 160 | 169 | 1.05 | 15.62 |
| "Other products" | 60.85 | 64 | 39 | 49 | 56 | 1.26 | 8.51 |
| Peaks 2-6 (sugar-oligo) | | 1066 | 390 | 661 | 936 | 1.69 | 85.46 |

TABLE 4

Calibration statistics for COS oligomers determined by size exclusion chromatography (SEC).

| Standard | Number of peak | RT Actual (min) | MW (g/mol) | Log MW | Error (%) |
|---|---|---|---|---|---|
| Cellohexaose | 1 | 52.00 | 991 | 2.996 | -2.39 |
| Cellopentaose | 2 | 52.60 | 829 | 2.919 | -1.56 |
| Cellotetraose | 3 | 53.41 | 666 | 2.824 | 1.72 |
| Cellotriose | 4 | 54.30 | 504 | 2.702 | 1.55 |
| Cellobiose | 5 | 55.65 | 342 | 2.534 | 4.63 |
| Glucose | 6 | 57.43 | 180 | 2.255 | -4.22 |

Example 3

This example relates to the analysis of the methanol soluble fraction MeOH-1 from Example 1. The methanol soluble fraction contained lignin and was analyzed with an Agilent 1260 μHPLC equipped with PSS MCX 100000 and 1000 Å columns (the columns are available from Polymer Standards Service (PSS)). All samples were prepared at about 1 mg/ml concentration. Pure degassed and 0.45μ filtered 0.1 M NaOH was used as the eluent at a flow rate of 0.5 ml/min. PSS sulfonated polystyrenes available from PSS were used as calibration standards. Samples were run at the temperature of 30° C. with the RI detector kept at 30° C. and the UV detector set to 280 nm. The SEC and GPC results were analyzed using the Cirrus extension program for ChemStation software to calculate MMD of all components.

Figure 2:
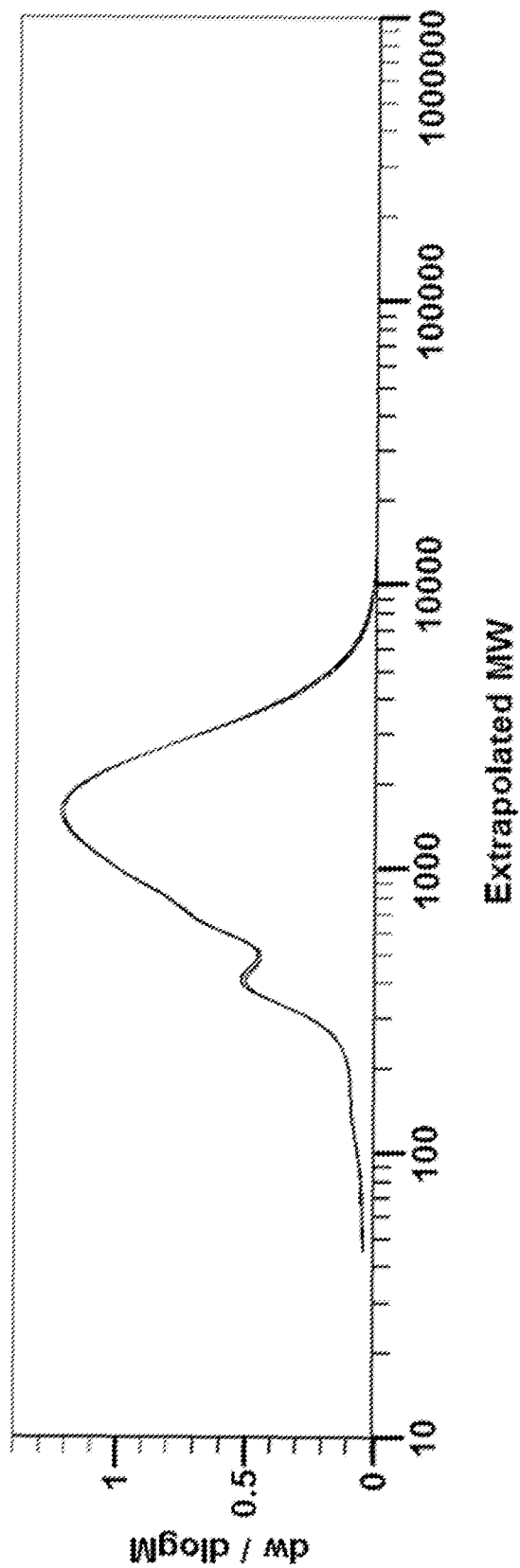
FIG. 2 shows a molar mass distribution of lignin in WL samples.

Specifically, the methanol soluble polyphenolics were analyzed with PSS MCX columns and the resulting MMDs are found in Table 5. The analysis was performed using calibration standards with retention time (RT) between 28.0-40.0 min. The calibration graph was built with the coefficient of determination of 0.9886, and the linear correlation coefficient of −0.9943. Interestingly, while a weight average molecular weight of lignin present in WL-0 and WL-1 is substantially same at about 1600-1700 g/mol, the weight % of lignin in each WL sample differed: about 20 wt. % in WL-1 and about 30 wt. % in WL-0. FIG. 2 depicts the molar mass distribution plots of lignin in WL-0 and WL-1 samples (which essentially overlap).

TABLE 5

Molar Mass Distribution of lignin in WL samples.

| WL-lignin Sample | MMD (g/mol) | | | | |
|---|---|---|---|---|---|
| | Mp | Mn | Mw | Mz | PDI |
| WL-0 | 1595 | 713 | 1627 | 8321 | 2.28 |
| WL-1 | 1588 | 709 | 1666 | 9031 | 2.35 |

Example 4

This example relates to analysis of the cellulose present in WL samples (DMAc/LiCl sample), from step (iv) in Example 1. The solution at 8% by weight LiCl in DMAc was diluted to a concentration of 0.8 wt. % LiCl in DMAc and analyzed on a Viscotek GPCMax equipped with LT6000L columns and the TDA 305 detector array, with LALLS, RALLS, RI and Intrinsic Viscosity detectors. The eluent was the same as the sample solvent and the elution speed was kept at 1.0 ml/min. Standards were 65k and 95 k Da PMMA standards from Malvern. The software for MMD calculations was the OmniSEC program and all samples were prepared in the ~2-5 mg/ml concentration range. The calculated WL cellulose molar mass distribution and DP results are detailed in Table 6. A dn/dc value of 0.136 mL/g was used in the GPC measurements of the WL-0 and WL-1 samples. The system was calibrated using different standards. The data presented in Table 7 illustrates the accuracy of the triple detection method by measuring the molar mass distribution of a known standard after calibration with another standard. Specifically, the instrument was calibrated with PMMA 65k available from Malvern Instruments, and the accuracy of the calibration checked with PMMA 95k also available from Malvern Instruments. The column "PMMA 95k official standard" in Table 7 reports the "official" molecular weight of the sample as provided by Malvern Instruments, whereas the column "PMMA 95k experimental" reports the molecular weight as measured on the calibrated instrument.

TABLE 6

The Molecular Mass Distribution of the cellulose in WL samples.

| Sample | $\overline{Mw}$ (g/mol) | $\overline{Mn}$ (g/mol) | $\overline{Mp}$ (g/mol) | $\overline{Mz}$ (g/mol) | PDI | *DP |
|---|---|---|---|---|---|---|
| WL-0 | 15,516 | 9,831 | 7,073 | 34,412 | 1.578 | 96 |
| WL-1 | 12,979 | 8,771 | 6,455 | 23,294 | 1.480 | 80 |

*DP is calculated using Mw and is based on the anhydroglucose monomer (with MW = 162 g/mol; glucose-water)

TABLE 7

Molecular Mass Distribution for standard samples.

| Property | PMMA 95k official standard | PMMA 95k experimental |
|---|---|---|
| $\overline{Mw}$ (g/mol) | 95,081 | 99,350 |
| $\overline{Mn}$ (g/mol) | 46,546 | 49,858 |
| PDI | 2.04 | 1.99 |

Figure 3:
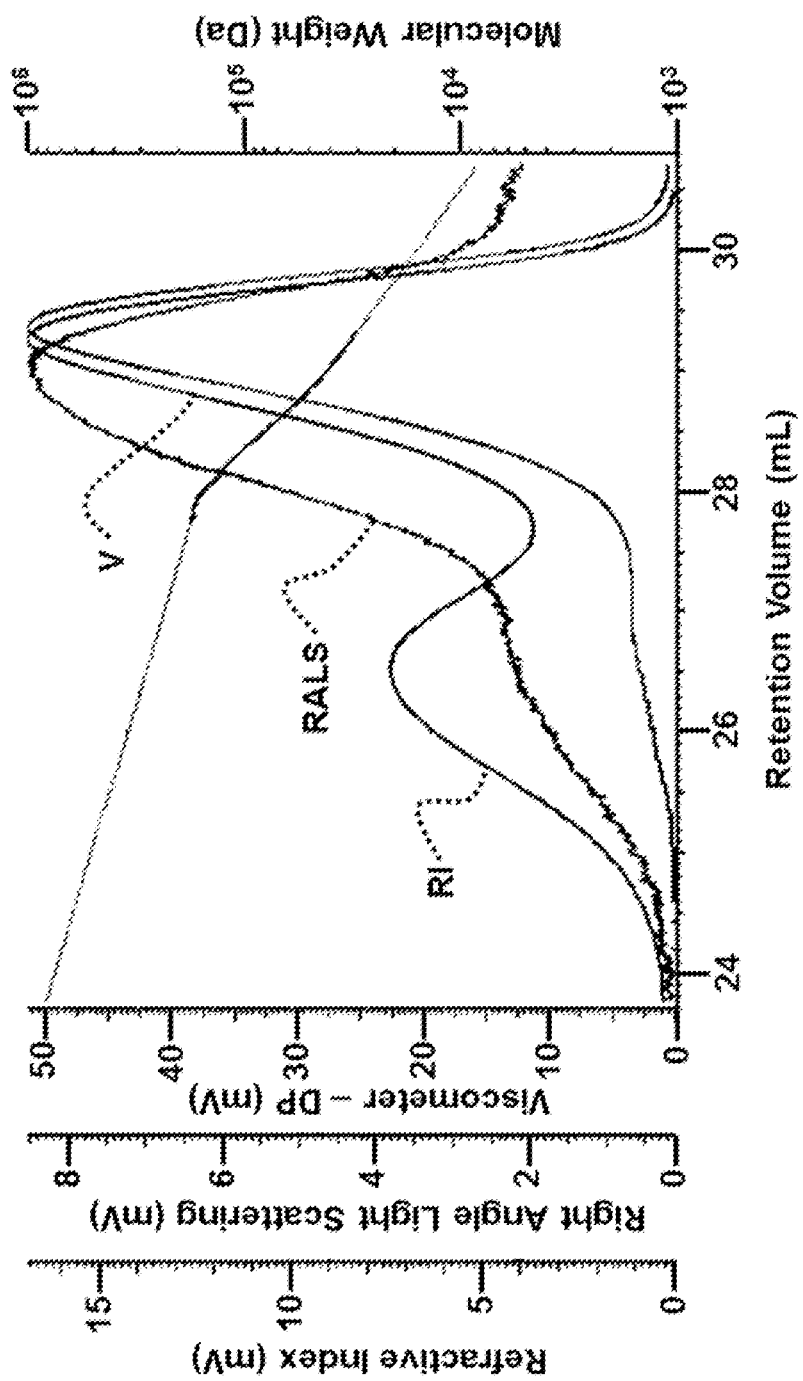
FIG. 3 shows a molar mass distribution of the WL-0 sample, as determined by triple detection (see examples).
Figure 4:
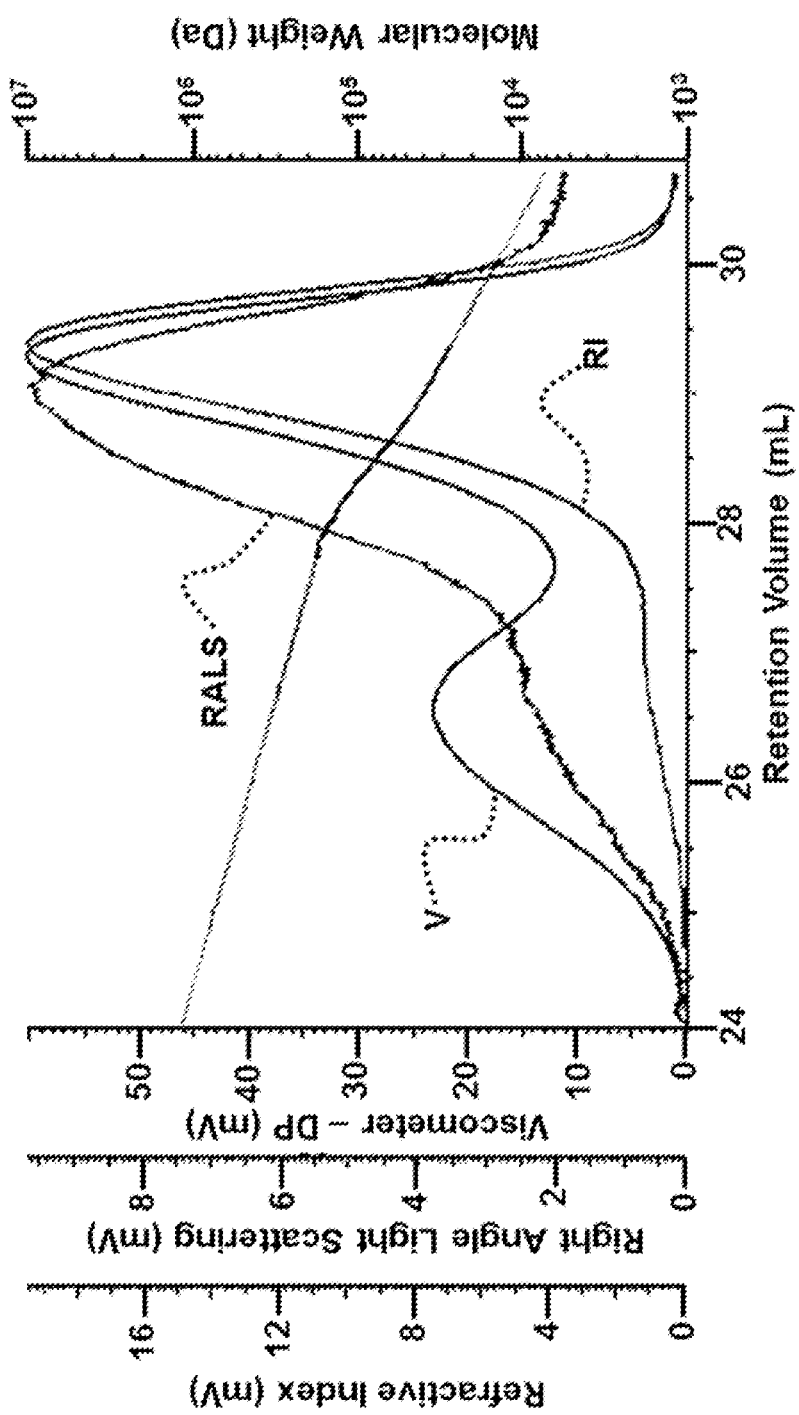
FIG. 4 shows a molar mass distribution of the WL-1 sample, as determined by triple detection (see examples).
Figure 5:
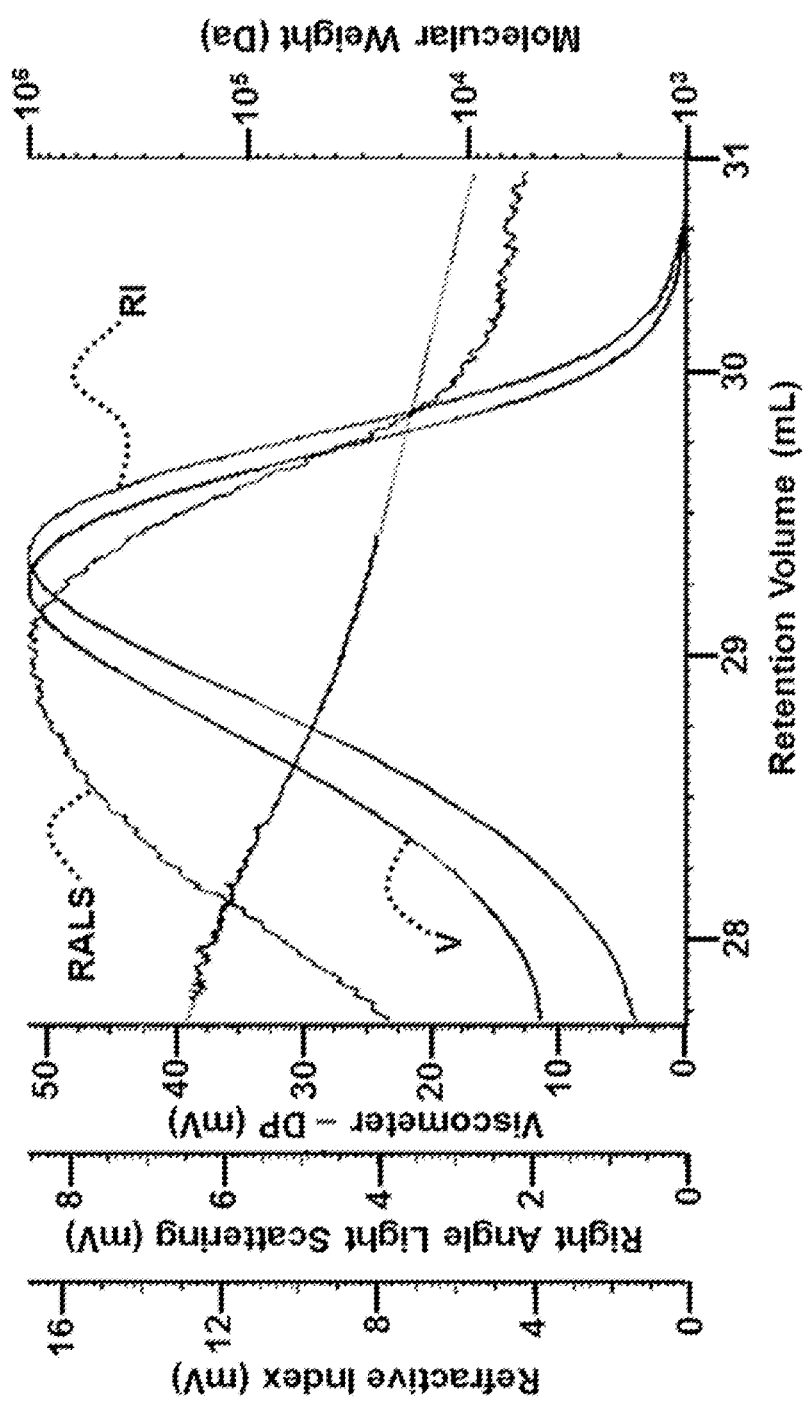
FIG. 5 shows a molar mass distribution of the WL-0 sample, as determined by triple detection, when only the large peak is considered (see examples).
Figure 6:
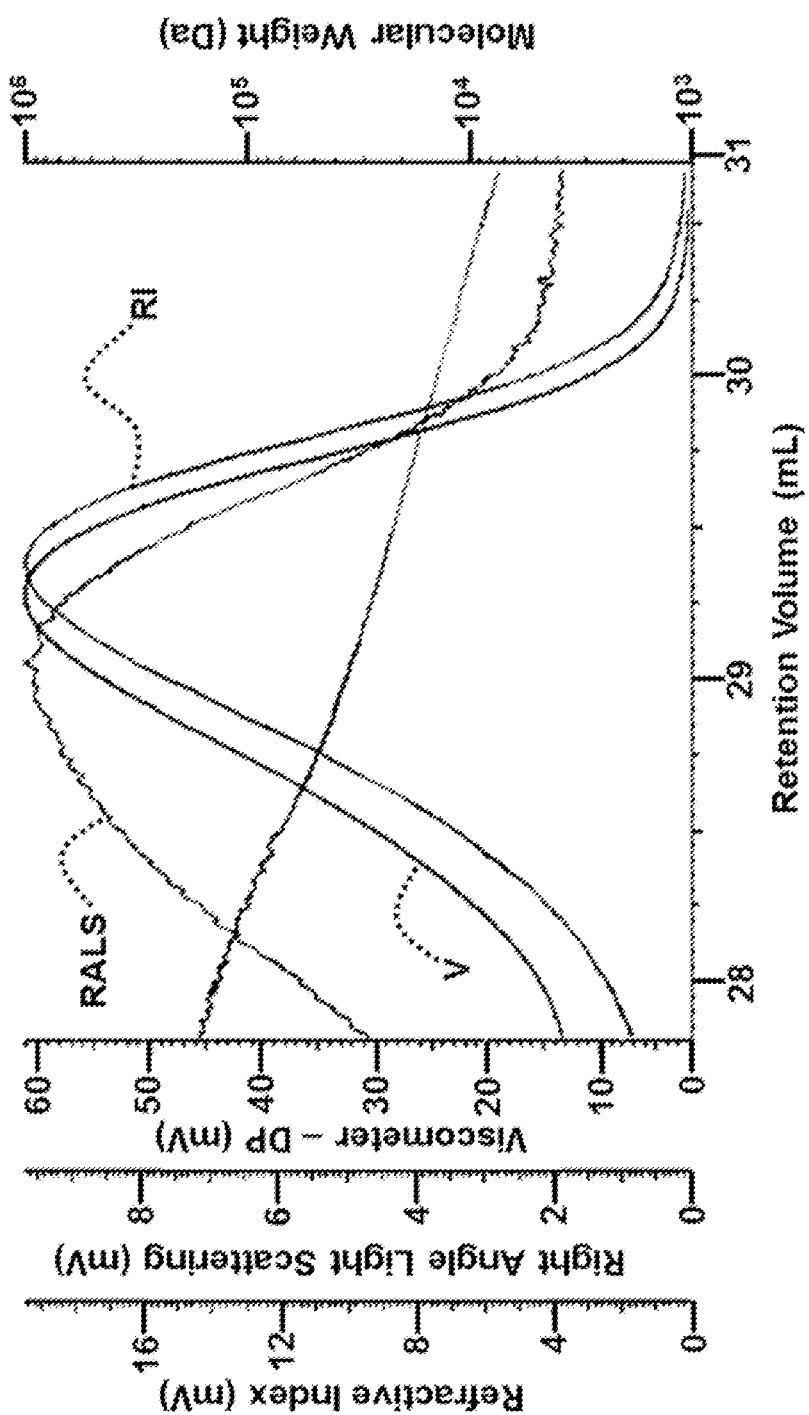
FIG. 6 shows a molar mass distribution of the WL-1 sample, as determined by triple detection, when only the large peak is considered (see examples).

As illustrated in FIGS. 3-4, the viscosity measurements of the eluent containing the celluloses result in an appearance of the "doublet" peak, wherein the "tail" is measured by the RI detector. It was found that the tail only represents a minor amount of the total sample based on RI integration (RI signal is proportional to the concentration). Accordingly, a more accurate value is considered when only the "large" cellulose peak is integrated. The results of this integration are shown Table 8 and FIGS. 5-6. It was found that the "large" cellulose peak represents about 93.19% and 92.61% for WL-0 and WL-1, respectively, of the total RI signal integral area that includes the "tail."

TABLE 8

The molar mass distributions of cellulose in WL samples calculated on a basis of the "large" peak obtained in GPC measurements.

| Sample | $\overline{Mw}$ (g/mol) | $\overline{Mn}$ (g/mol) | $\overline{Mp}$ (g/mol) | $\overline{Mz}$ (g/mol) | PDI | *DP |
|---|---|---|---|---|---|---|
| WL-0 | 11,294 | 8,391 | 6,504 | 22,797 | 1.346 | 70 |
| WL-1 | 10,197 | 7,563 | 5,921 | 18,615 | 1.348 | 63 |

*DP is calculated using Mw and is based on the anhydroglucose monomer (with MW = 162 g/mol; glucose-water)

Example 5

This example demonstrates the measurement of relative amounts of type-I cellulose, type-II cellulose, and amorphous cellulose in the cellulose product by solid state $^{13}$C CP-MAS NMR spectroscopy. This example employs HHR, SHR-50, and SHR-80 samples.

To prepare HHR, comminuted (ground) biomass comprising hardwood having an average particle size of less than about 500 μm was mixed with water to form a slurry. The slurry was reacted at a temperature of about 170-245° C. and a pressure of about 35-62 bar for a period of about 1-120 minutes (termed "the HH process"). The reaction mixture was cooled to less than 100° C. and depressurized to less than 10 bar. The cooled and depressurized reaction mixture was then filtered using a filter press. The solids correspond to the HHR sample.

To prepare the SHR-50 and SHR-80 samples, the HHR solids were collected and re-slurried with water. The slurry was contacted with near-critical or supercritical water having a temperature of about 360° C. to about 600° C. and a pressure of about 200 bar to about 600 bar, and the resulting mixture maintained at reaction conditions for a residence time of about 0.1 sec to about 8 sec. The SHR-50 sample has about 50 wt. % lignin and 50 wt. % cellulose on a dry basis. The SHR-80 sample has about 80 wt. % lignin and 20 wt. % cellulose on a dry basis. In general, SHR solids having different lignin contents can be prepared by varying the reaction conditions: generally higher temperature and/or longer residence time lead to higher lignin content (since more cellulose is hydrolyzed and removed in the liquid GOS stream), and generally lower temperature and/or shorter residence times lead to lower lignin content (since more cellulose remains unhydrolyzed and remains with the solids).

Solid State $^{13}$C CP-MAS NMR spectroscopy is a well-established method to determine the supramolecular structure and crystallinity of cellulose, as discussed, for example, by Zuckerstatter, G., et al., in *"The Elucidation of Cellulose Supramolecular Structure by $^{13}$C CP-MAS NMR"*, Lenzinger Berichte, 87, (2009), 38-46, incorporated herein by reference in its entirety. Generally, the obtained spectrum of cellulose exhibits easily separable resonances from crystalline and less-ordered domains for the C4 and C6 atoms in the anhydroglucose unit (AGU). The cellulose C4 signal is particularly well resolved and stretches over a wide chemical shift range from about 79 ppm to 91 ppm. Prior work in the art has established that the signals at about 89 ppm and 84 ppm can be attributed to crystalline and non-crystalline (amorphous) components, respectively, the relative components of which may be determined either by integration of peak areas using fixed integration limits, or by signal deconvolution. Herein, the spectra are analyzed by the method of deconvolution as described in the reference cited above. In differentiating between, and quantifying relative amounts of, type-I cellulose, type-II cellulose, and amorphous cellulose, it has been found advantageous to analyze the C6 line shapes, the resonances for which are well-separated.

The following residues, prepared as described above (Example 1), were further studied by $^{13}$C CP-MAS NMR spectroscopy to ascertain structural information, crystallinity and cellulose type for the cellulose component of the residues: HHR, SHR-50, SHR-80. For each residue, samples were prepared for NMR study as follows: the samples were exhaustively washed with water to remove residual water soluble matter and exhaustively extracted with 80% (volume/volume) aqueous dioxane at room temperature to eliminate the maximum amount of lignin from them. Usually, about 85-90% of lignin originally present in the sample was removed by this procedure.

Solid state NMR spectra were obtained these washed and extracted preparations. The $^{13}$C CP-MAS NMR spectrometer preparation and operating conditions are described in the cited reference (page 39, second column) To eliminate residual lignin signals from the spectra, the spectrum of the corresponding pure extracted lignin was acquired and subtracted from these spectra. The signal due to —OMe groups at about 56 ppm was used for normalizing the spectra before the subtraction. The pure extracted lignin for each of the HHR, SHR-50, and SHR-80 samples was obtained by subjecting separate fresh samples to extraction at room temperature under mixing during 3 hours at liquid:solid (L:S) ratio of 10:1 (w/w) using 1 wt. % aqueous sodium hydroxide solution. The alkaline lignin solution was then separated from any undissolved solids by centrifugation, and the solubilized lignin was precipitated by adjusting the pH to 2.0, followed by filtering and washing with water, with subsequent drying. These pure lignin samples for each of the HHR, SHR-50, and SHR-80 samples were used in the spectrum subtraction.

Figure 7A:
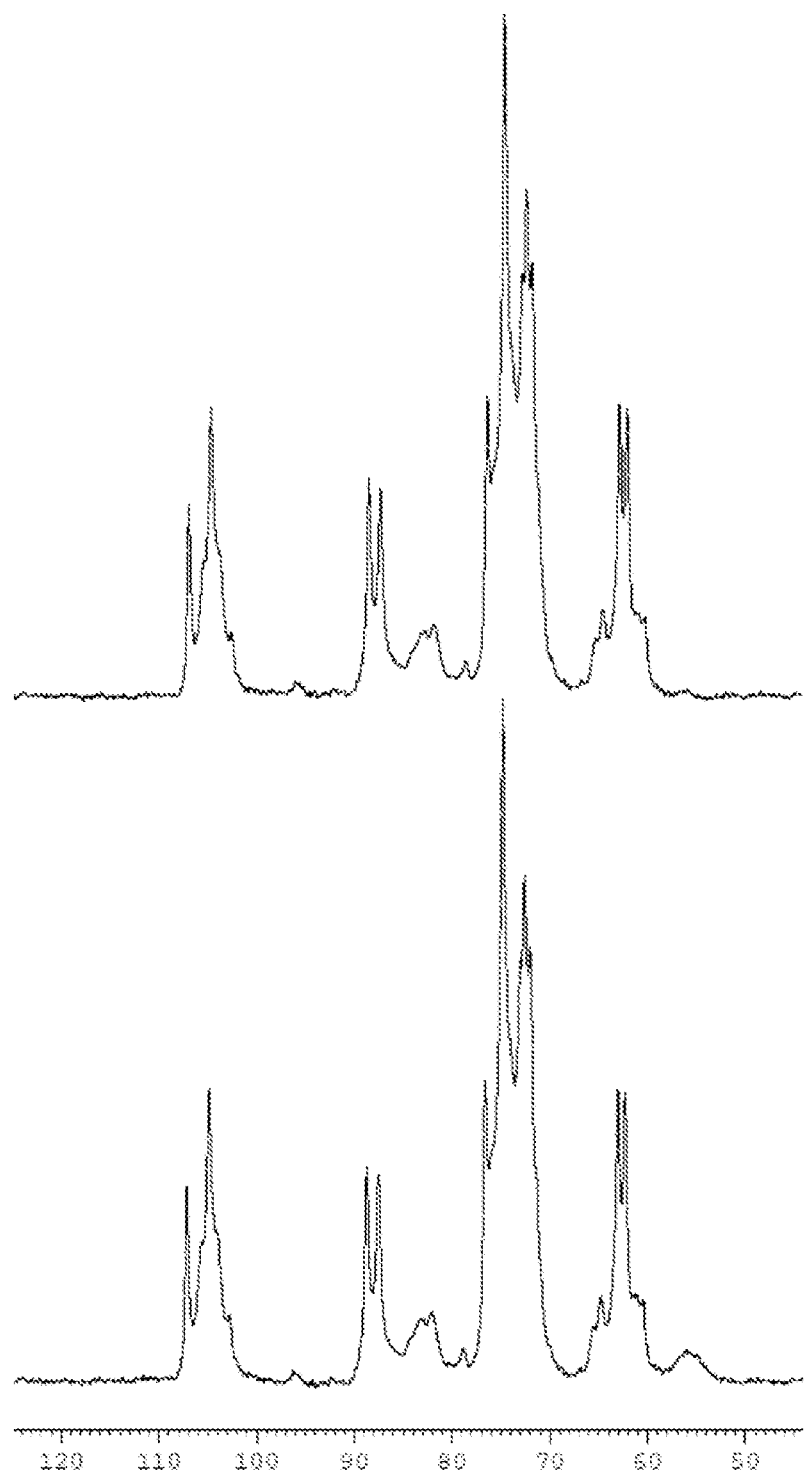
FIG. 7A shows the $^{13}C$ NMR spectrum for SHR-50 (see Example 5).
Figure 7B:
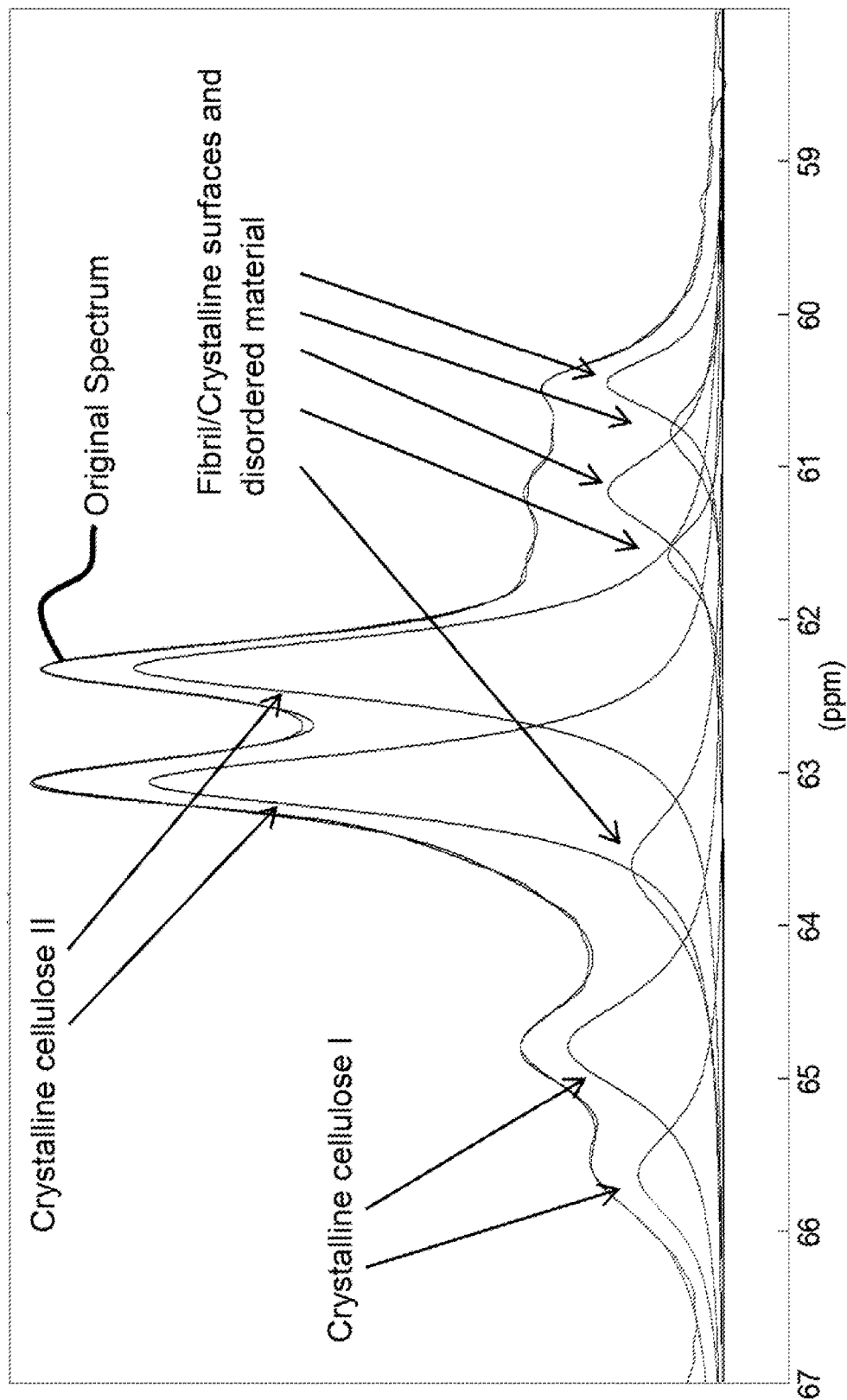
FIG. 7B shows the deconvoluted and fitted curve in the C6 region for SHR-50 (see Example 5).

Because the C4 region for HHR shows only type-I cellulose, the analysis is more readily performed on this C4 chemical shift range (from about 79 ppm to 91 ppm); in the case of SHR-50 and SHR-80, the C4 region shows significant amounts or predominantly type-II cellulose for which the C6 region (chemical shift range from about 58 ppm to 67 ppm) is more readily analyzed. FIG. 7A shows the NMR spectrum for SHR-50. The deconvoluted and fitted curve in the C6 region for SHR-50 is shown in FIG. 7B. The spectra for HHR and SHR-80 are not shown, but the deconvolution and curve fitting was done in the same manner. The $^{13}C$ CP-MAS NMR analysis of HHR, SHR-50, and SHR-80 is presented in Tables 9, 10 and 11, respectively.

TABLE 9

$^{13}C$ CP-MAS NMR analysis of sample HHR.

| | δ (ppm) | Width (ppm) | Integral (%) |
|---|---|---|---|
| $I_\alpha$ | 89.41 | 0.44 | 0.87 |
| $I_{\alpha+\beta}$ | 88.75 | 0.66 | 21.08 |
| $I_\beta$ | 87.92 | 1.17 | 27.13 |
| paracrystalline | 88.30 | 1.75 | 7.31 |
| accessible fibril surface | 84.34 | 1.15 | 10.42 |
| accessible fibril surface | 83.25 | 0.95 | 8.10 |
| inaccessible fibril surface | 83.92 | 2.35 | 14.00 |
| amorphous cellulose | 82.06 | 1.85 | 11.08 |

TABLE 10

$^{13}C$ CP-MAS NMR analysis of SHR-50

| | δ (ppm) | Width (ppm) | Integral (%) |
|---|---|---|---|
| crystalline I | 65.63 | 0.77 | 5.93 |
| crystalline I | 64.79 | 0.81 | 11.66 |
| crystalline II | 63.06 | 0.51 | 28.24 |
| crystalline II | 62.32 | 0.51 | 29.14 |
| fibril/crystallite/disordered | 63.61 | 0.90 | 7.76 |
| fibril/crystallite/disordered | 61.58 | 0.46 | 2.50 |
| fibril/crystallite/disordered | 61.16 | 0.64 | 7.01 |
| fibril/crystallite/disordered | 60.77 | 0.51 | 2.63 |
| fibril/crystallite/disordered | 60.45 | 0.46 | 5.13 |

TABLE 11

$^{13}C$ CP-MAS NMR analysis of SHR-80

| | δ (ppm) | Width (ppm) | Integral (%) |
|---|---|---|---|
| crystalline II | 63.04 | 0.46 | 40.63 |
| crystalline II | 62.29 | 0.49 | 44.39 |
| fibril/crystallite/disordered | 62.68 | 0.69 | 2.25 |
| fibril/crystallite/disordered | 61.60 | 0.18 | 0.60 |
| fibril/crystallite/disordered | 61.10 | 0.55 | 5.63 |
| fibril/crystallite/disordered | 60.44 | 0.60 | 6.51 |

Using the curve fitting results, the relative ratios of type-I cellulose, type-II cellulose, and amorphous cellulose were determined as follows. For the HHR sample, ratio of type-I cellulose to amorphous cellulose was about 1:0.77. There was no type-II cellulose in the HHR sample. For the SHR-50 sample, the ratio of type-I cellulose to type-II cellulose to amorphous cellulose was about 1:3.3:1.4. In other words, for the SHR-50 sample, the ratio of amorphous cellulose to total amount of type-I and type-II cellulose is about 1:3 (1.4/(1+3.3)). For the SHR-80 sample, the ratio of type-II cellulose to amorphous cellulose was about 1:0.2. There was no type-I cellulose in the SHR-80 sample.

Type-II cellulose is not found in naturally occurring biomass. The HHR residue (step 1 residue) resulting from mild hydrolysis conditions of the biomass feedstock that enters the process also does not contain type-II cellulose. However, the analysis of the $^{13}C$ CP-MAS NMR spectra shows that the cellulose present in the SHR-50 and SHR-80 residues resulting from the supercritical water hydrolysis of the step 1 solid residue is largely (57.4% for SHR-50) or almost entirely (85.0% for SHR-80) type-II cellulose (the remainder of the cellulose being amorphous).

Example 6

In this example, a slurry resulting from supercritical hydrolysis of biomass was centrifuged into three fractions as described in Example 1. The WL-0 layer was then further purified and subjected to electron microscopy, x-ray crystallography, and particle size analysis. Analysis of the solid fractions demonstrated that the "white solids" are cellulose enriched and the "dark solids" are lignin enriched.

Figure 8:
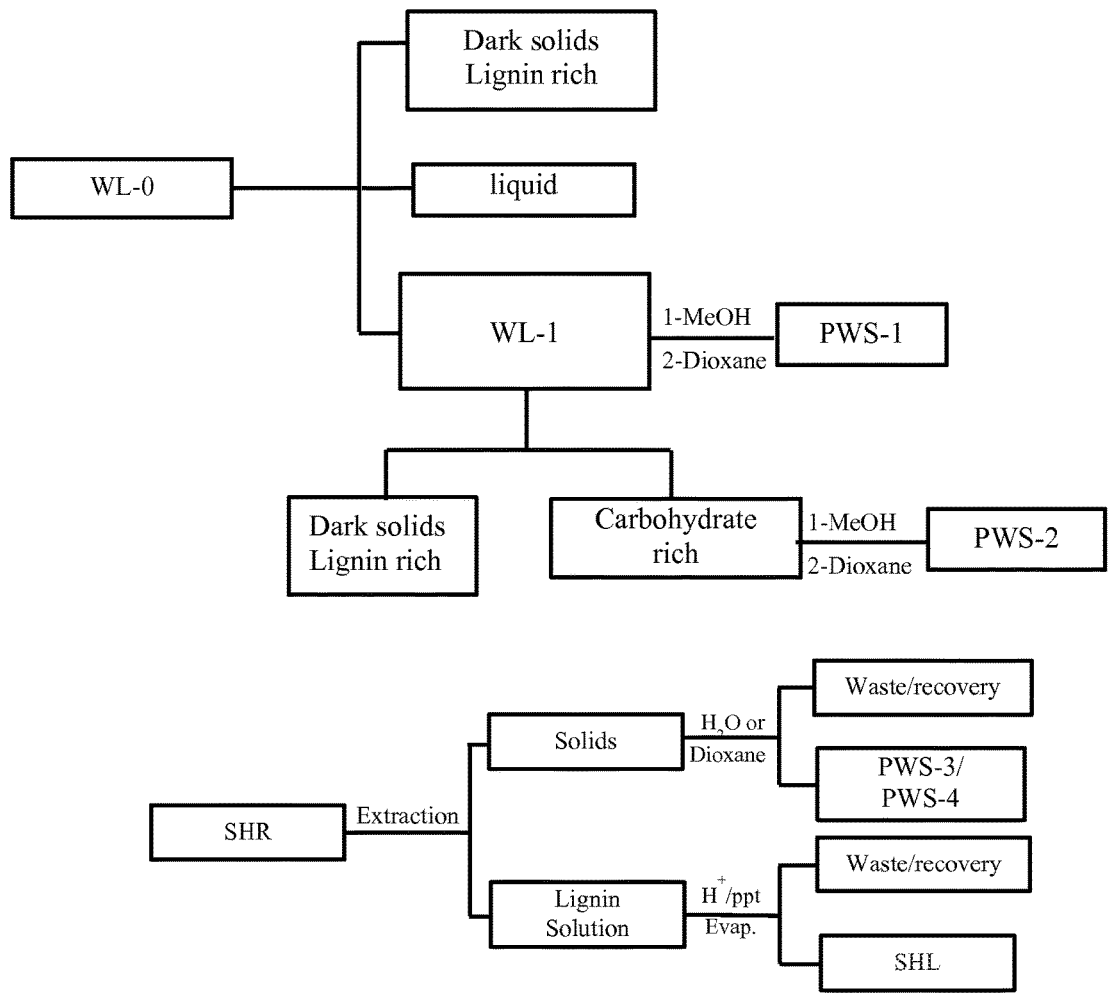
FIG. 8 shows purification routes of the supercritical hydrolysis slurry.

The white layer (WL-0) separated from the supercritical hydrolysis slurry by centrifugation was purified according to the route depicted in FIG. 8. The centrifuged white layer (WL-0) was re-slurried in water, centrifuged, and then the white carbohydrate-rich layer (WL-1) sequentially washed with methanol and then dioxane:water (90:10 by volume), yielding a sample of purified white solids 1 (PWS-1). Another sample was generated by centrifuging an additional time the WL-1 fraction, and then subsequently washing the resulting carbohydrate-rich solids layer with methanol and then dioxane:water (90:10), yielding a second sample of purified white solids 2 (PWS-2).

In another washing experiment, a sample of supercritical hydrolysis slurry residue ("SHR") (containing both the lignin-rich fraction and cellulose-rich fraction, without any centrifugation) was extracted with either (1) a solution of NaOH (1 wt. %) in water or (2) dioxane:water (90:10 by volume). The resulting solids from extraction (1) were washed with water, and the resulting solids from (2) were washed with dioxane, thereby generating two cellulose rich portions: purified white solids PWS-3 and PWS-4, respectively. A lignin fraction ("SHL") was obtained either by evaporation of the alkaline dioxane/water solution, or by acidification of the alkaline dioxane/water solution to precipitate solid lignin.

Figure 9:
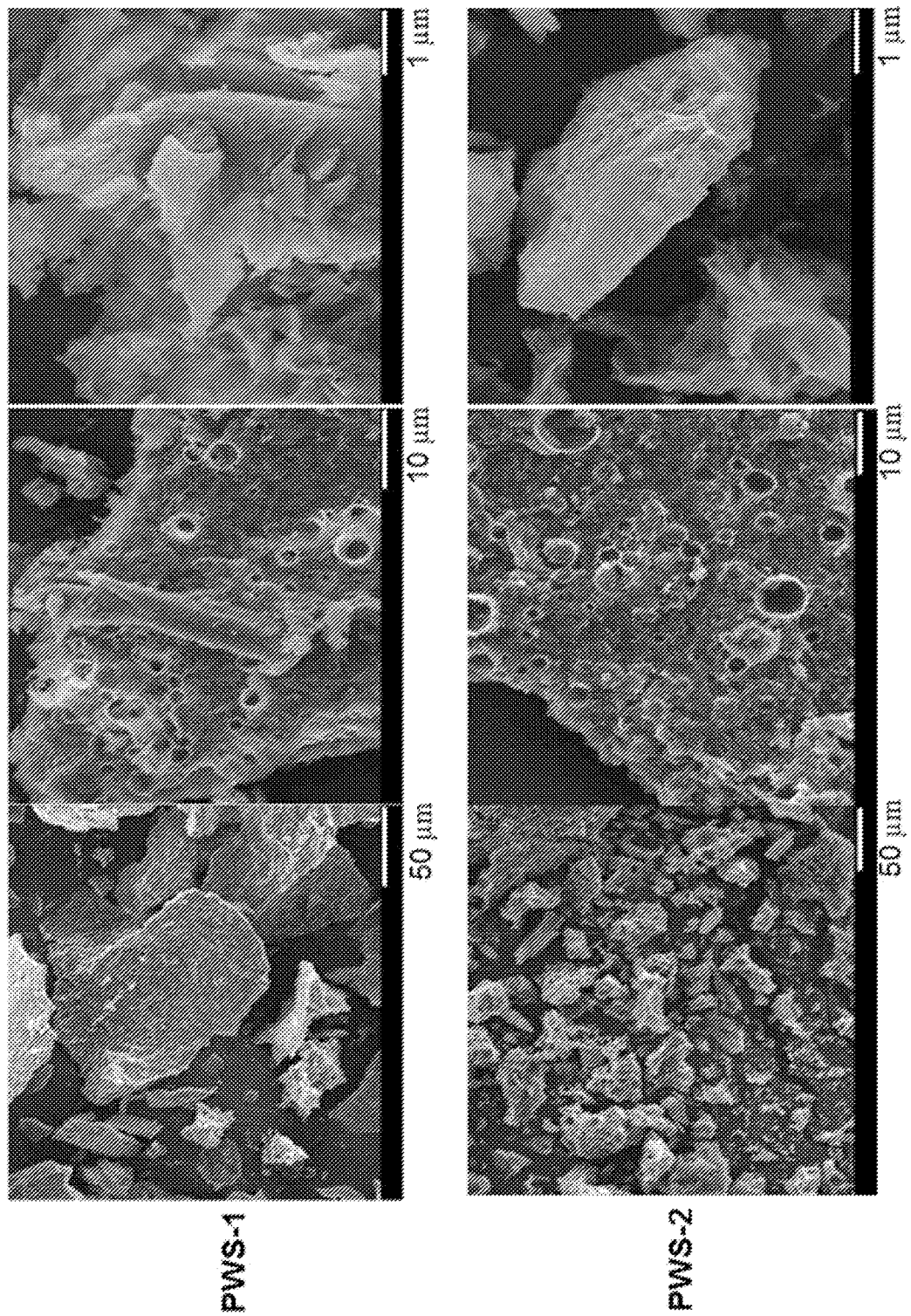
FIG. 9 shows FESEM images of the purified powdered white solids PWS-1 and PWS-2 (see examples).

The microstructure and surface morphology of the PWS-1, 2, 3 and 4 samples were analyzed by Field Emission Scanning Electron Microscopy ("FESEM") (JEOL, 6400F, Peabody, Mass., USA operating at 10 kV). The powder samples were fixed on carbon tape, coated with a layer of Au/Pt, and the resulting SEM images are depicted on FIG. 9.

Figure 10:
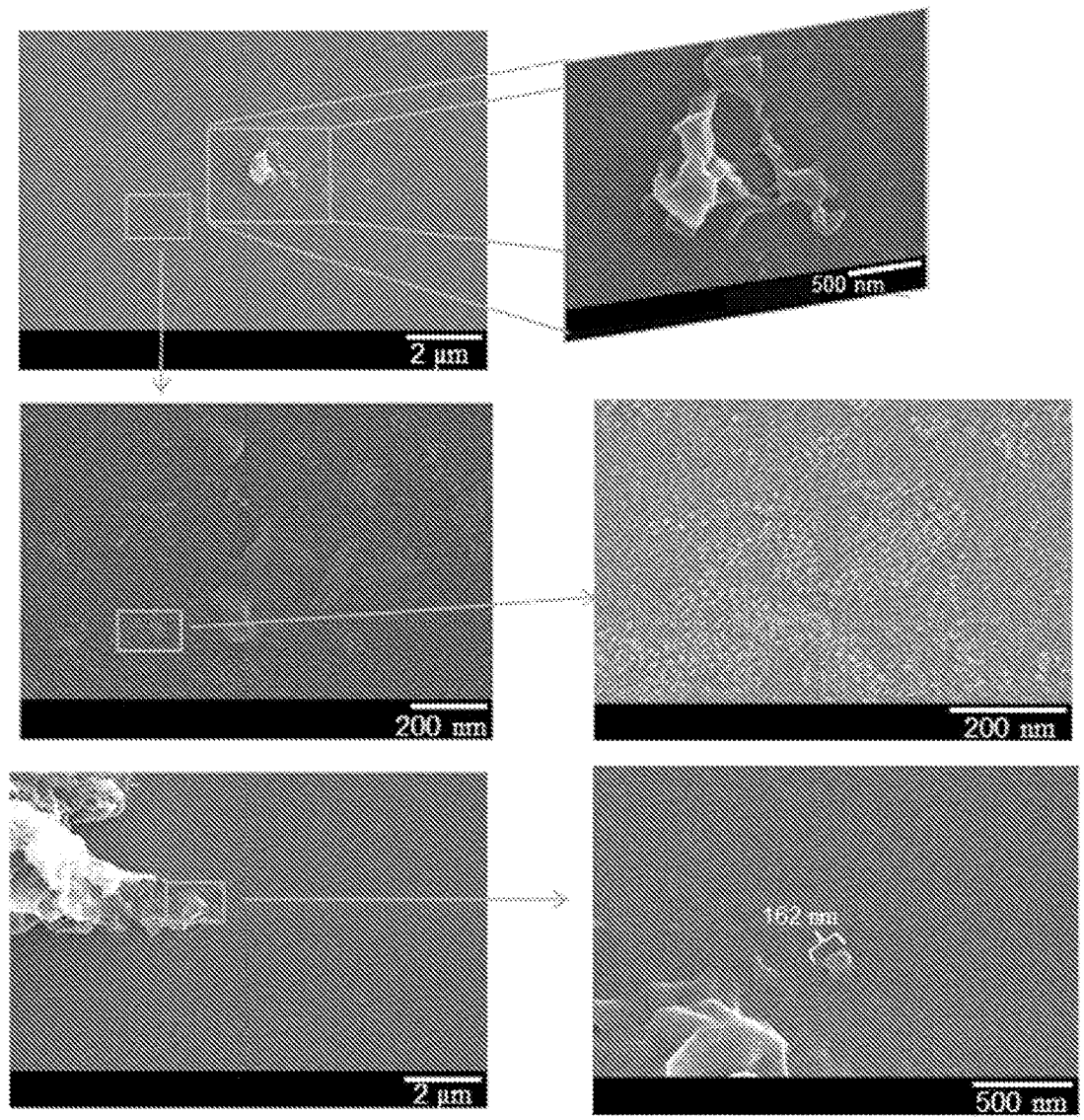
FIG. 10 shows FESEM images of the purified powdered white solids PWS-1 and PWS-2 that were re-dispersed in water (see examples).

In order to minimize aggregation in the samples due to hydrogen bonding and other non-covalent interactions, the samples were dispersed in water (0.05%), stirred for 4 hours, and sonicated for 5 min prior to deposition. A few drops of the suspensions were air dried onto clean silicon wafers, fixed on carbon tape, coated with a layer of Au/Pt, and then analyzed by FESEM. The resulting images are depicted on FIG. 10.

Figure 11:
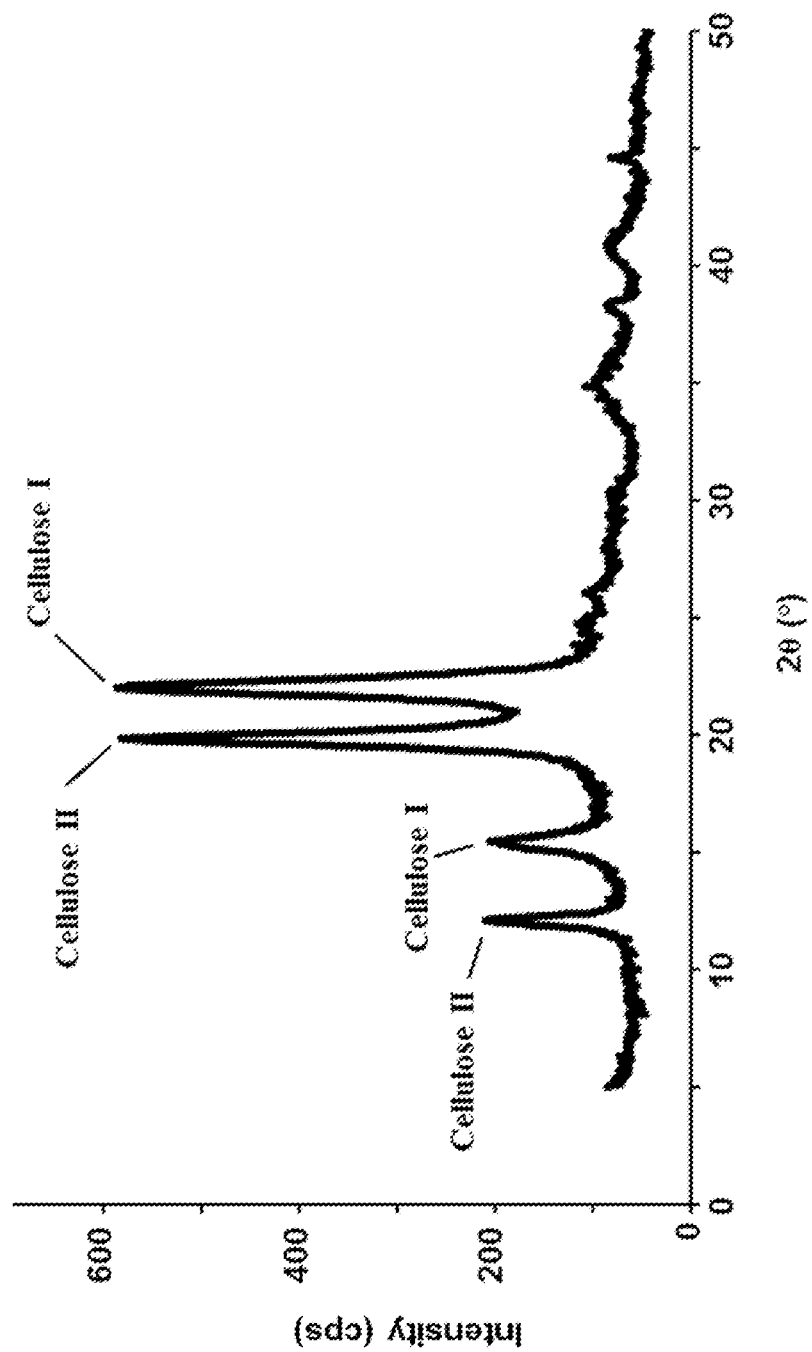
FIG. 11 shows X-ray diffraction (XRD) spectra of purified white solids (see examples).

The purified PWS-1, 2, 3 and 4 samples were further analyzed by x-ray diffraction ("XRD") using a Rigaku SmartLab X-Ray diffractometer equipped with a monochrometer using a Cu Kα radiation step size of 0.05° (2θ) and a count time of 5 sec at each step. The results are shown in FIG. 11.

It was found, based on the presence of the peak at 15.5° in the XRD of all samples analyzed, that under the employed supercritical conditions the type I cellulose is partially converted to type II cellulose. The estimated degree of crystallinity for all samples is shown in Table 12, calculated using the XRD peak height method, a technique well known in the art (see, e.g., Segal L., Creely J. J., Martin A. E. Jr, Conrad C. M.: An empirical method for estimating the degree of crystallinity of native cellulose using the x-ray diffractometer. Tex Res J 1962, 29:786-794, hereby incorporated by reference in its entirety).

TABLE 12

Estimated degree of crystallinity in %.

| PSW 1 | PSW 2 | PSW 3 | PSW 4 |
|---|---|---|---|
| 83 | 88 | 80 | 83 |

Figure 12:
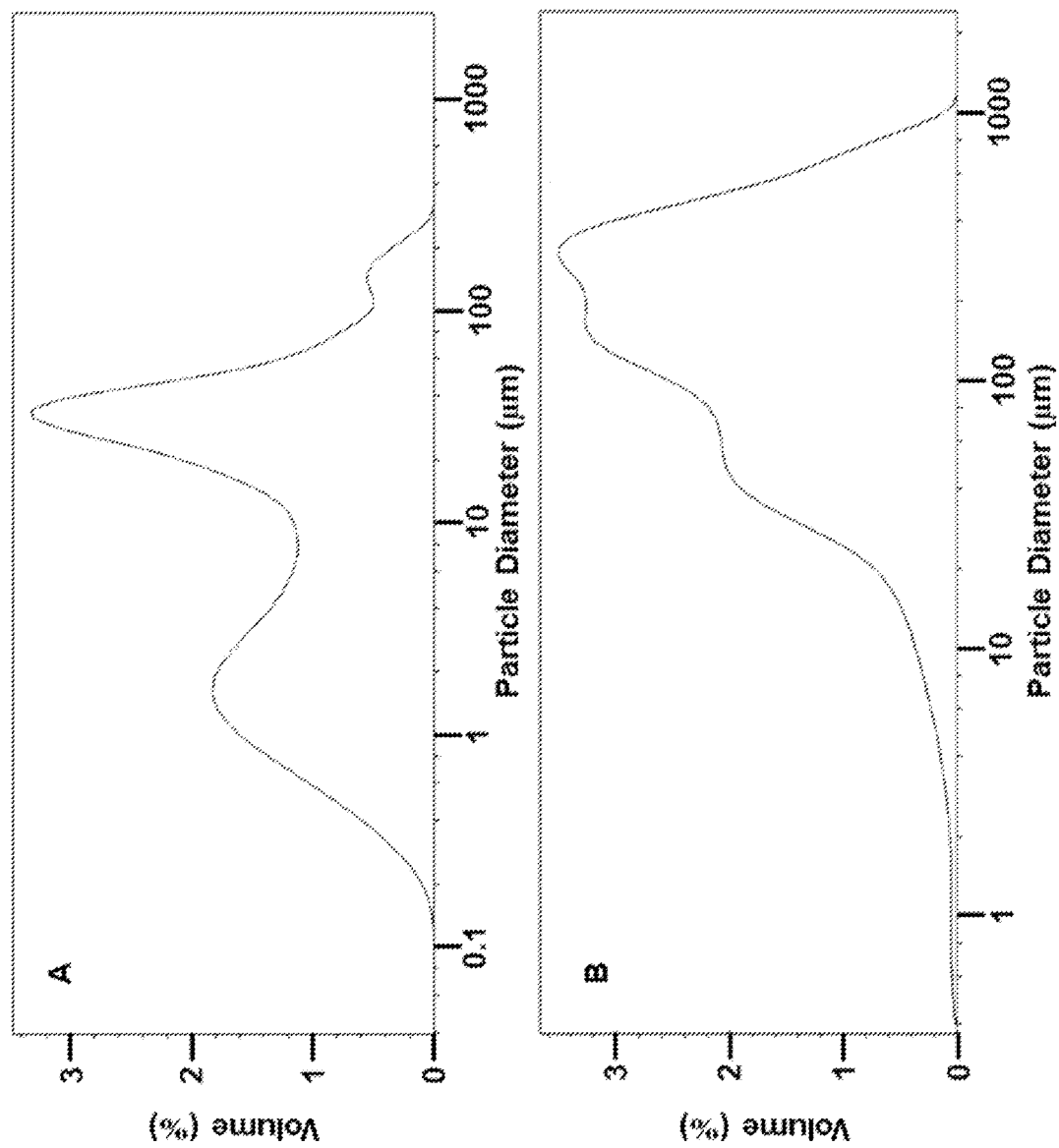
FIG. 12 shows a particle size distribution plot of supercritical hydrolysis slurry solids as received (A), and after step of drying (B) (see examples).
Figure 13:
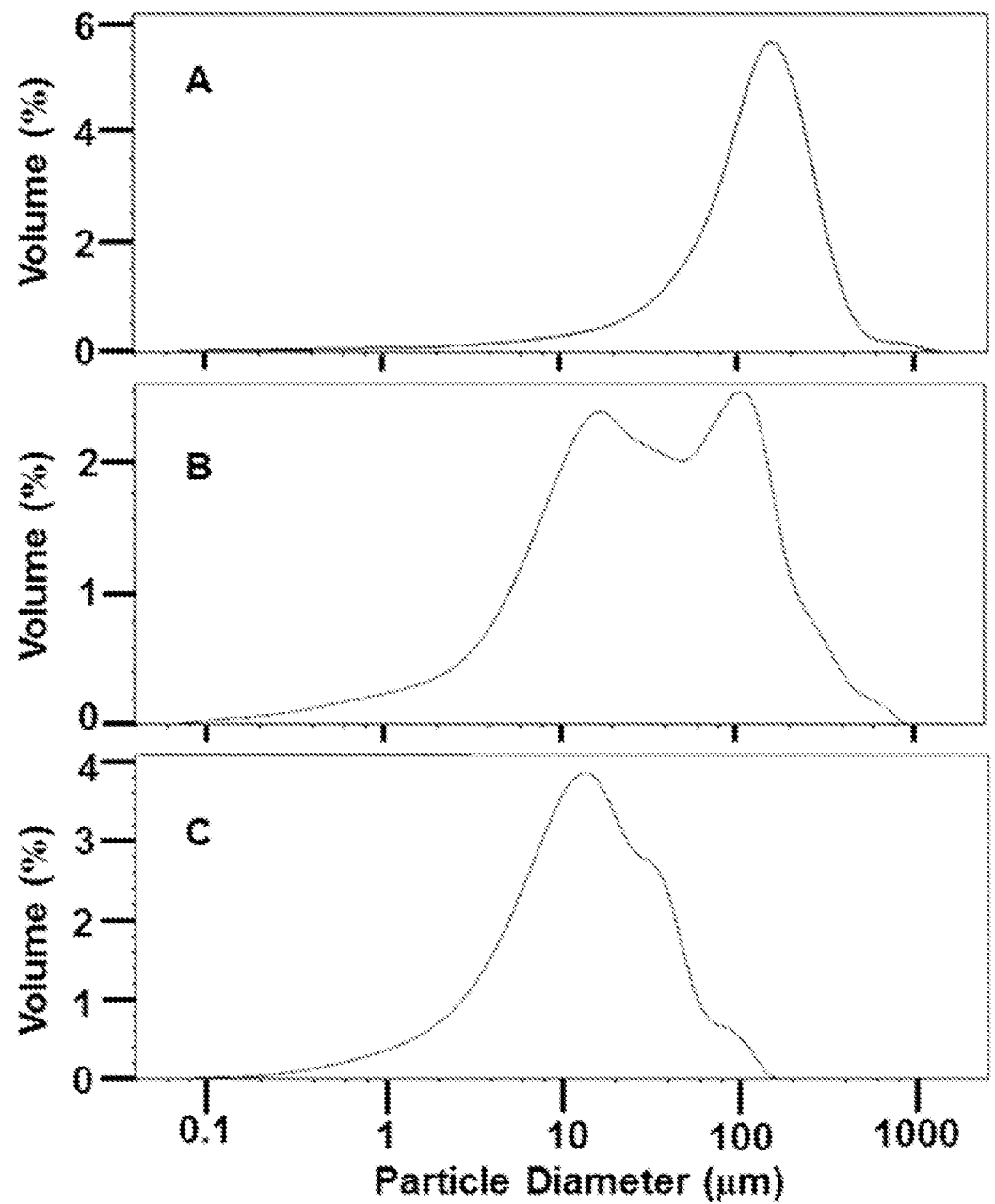
FIG. 13 shows a particle size distribution plot of PWS-2 (A), PWS-3 (B), and SHL (C) (see examples).

To measure particle size, the PWS samples (that were first dewatered and/or dried) were slurried in water at a concentration of 10 mg/ml and analyzed on a Beckman Coulter LS 13 320 Particle Size Analyzer. The results are presented in Table 13 The particle size distribution (PSD) of the sample after various treatments was compared. The PSD of the SHR solids that were not dried prior to the particle size measurements (SHR-wet) showed two distinct peaks in the spectrum with maxima at about 1.5 μm and 30 μm, while the same material after drying (SHR-Dried) showed a broad distribution with shoulders at about 50 μm and 200 μm, and maximum at about 400 μm (FIG. 12). It was demonstrated that PWS-1 and PWS-2 samples have a substantially symmetrical particle size distribution. On the other hand, it was demonstrated that the particle size distribution of PWS-3 and 4 samples showed a non-symmetrical distribution with two distinct peaks. Further, the PSD of the SHL lignin was similar to the PSD of the PWS-3 and PWS-4 samples, namely, a non-symmetrical distribution with lower median values at about 49 μm. FIG. 13 shows the PSD of A) PWS-2, B) PWS-3, and C) SHL.

TABLE 13

Particle Size distribution of white solids (PWS-1, 2, 3, 4) and SH solids (SHR) and Lignin (SHL).

| Sample | $D_{10}$, μm | $D_{50}$, μm | $D_{90}$, μm | Mean, μm | Median, μm |
|---|---|---|---|---|---|
| SHR-wet | 0.8 | 10.2 | 55.7 | 23.7 | 10.2 |
| SHR-dried | 25.8 | 146.5 | 458.5 | 201.6 | 146.5 |
| PWS-1 | 26.8 | 122 | 267 | 141 | 122 |
| PWS-2 | 20.1 | 96 | 255 | 135 | 96 |
| PWS-3 | 4.2 | 27.8 | 163 | 66.1 | 27.8 |
| PWS-4 | 5.6 | 80.3 | 276 | 116 | 80.3 |
| SHL | 2.7 | 13.2 | 48.8 | 21.8 | 13.2 |

Example 7

In this example, the viscosity of a white layer was measured. A WL-0 fraction from Example 1 was dispersed in water and centrifuged at 1250 rpm for 10 min to remove a residual dark layer (DL) that was present. An additional centrifuge pass at 3000 rpm for 10 min was conducted to ensure high a purity white layer. To remove any entrained soluble glucose oligosaccharides ("GOS"), the white layer samples were re-dispersed in water and centrifuged at 4000 rpm for 20 min, and the GOS was decanted. The remaining white layer sample was washed with deionized (DI) water and centrifuged again at 4000 rpm for additional 20 min. The final white layer sample in the form of a wet paste was diluted to 5.44 wt. % in DI water and its viscosity analyzed at T=23° C. The measured viscosity was about 2120 cps at 1 rpm, spindle 21, and 1760 cps at 2.5 rpm, spindle 21. Some thixotropic behavior was observed.

Example 8

In this example, the white layer (WL) purified according to Example 7 was analyzed by Inductive Coupled Plasma (ICP) analysis. Three separate samples weighing 0.8305 g, 0.4986 g, and 0.5990 respectively were transferred into three separate digestion tubes. Ten milliliters aliquots of 70% nitric acid (Fisher A509-P212 Lot 1112120, trace metal grade) were added to each digestion tube. Two reference samples, REF. 1 and REF. 2 were prepared by adding 10 ml aliquots of 70% nitric acid to two separate digestion tubes that did not contain white layer solids. All samples were mixed by hand at room temperature for 20 min. Digestion tubes were then capped and placed in the CEM Mars 6 microwave digester. Microwave digester conditions were kept as following: 20 minutes temperature ramp from room temperature to about 190° C.; holding all samples at 190° C. for 20 minutes. After the digestion was completed, all samples were cooled in a fume hood and vented. The digested solution was transferred to a 50 mL graduated centrifuge tube. The solutions were brought to a total volume of 35 mL with ICP grade type 1/MilliQ water having resistivity of 18 mega-ohm-cm. Samples were mixed and then transferred to an ICP sample tube and analyzed by ICP. The metal amounts that have been measured in the REF. 1 and 2 were averaged and marked as $REF_{aver}$. The data for all three samples was averaged and resulted averaged value was marked as $EXAM_{aver}$. The amount of metals and impurities measured for blank samples was subtracted from $EXAM_{aver}$, and the result labeled $EXAM^*_{aver}$. The results are presented in Tables 14-16.

TABLE 14

Metal Presence in the WL solids.

| SAMPLE ID | Al (ppm) | Ba (ppm) | Ca (ppm) | Cr (ppm) | Cu (ppm) | Fe (ppm) |
|---|---|---|---|---|---|---|
| $EXAM_{aver}$ | 1.8 | <DL | <DL | 2.6 | 2.67 | 8.47 |
| $EXAM^*_{aver}$ | 1.2 | <DL | <DL | 1.55 | 2.07 | 4.97 |
| $REF_{aver}$ | 0.6 | <DL | <DL | 1.05 | 0.6 | 3.5 |

**DL - Detection Limit

TABLE 15

Metal Presence in the WL solids.

| SAMPLE ID | K (ppm) | Li (ppm) | Mg (ppm) | Mn (ppm) | Mo (ppm) | Na (ppm) |
|---|---|---|---|---|---|---|
| $EXAM_{aver}$ | 0.47 | <DL | 1.1 | <DL | <DL | 126.17 |
| $EXAM^*_{aver}$ | 0.47 | <DL | 1.1 | <DL | <DL | 36.42 |
| $REF_{aver}$ | <DL | <DL | <DL | <DL | <DL | 89.75 |

**DL - Detection Limit

TABLE 16

Impurities Presence in the WL solids.

| SAMPLE ID | Ni (ppm) | P (ppm) | S (ppm) | Si (ppm) | Sr (ppm) |
|---|---|---|---|---|---|
| EXAM$_{aver}$ | <DL | <DL | 10.53 | 2.3 | 0.0 |
| EXAM*$_{aver}$ | <DL | <DL | 3.73 | 2.3 | 0.0 |
| REF$_{aver}$ | <DL | <DL | 6.8 | <DL | 0.0 |

DL: Detection Limit

Example 9

In this example, GPC molecular weight measurements were performed for two "white layers," similar to the GPC measurements of Example 4. Notably, the steps used to dissolve the cellulose "white layers" are different from, but similar to, the "first condition" used in Example 4. The GPC instrument is also different in this example.

The first sample, PWS-2 from Example 6, was dissolved according to a procedure adapted from Henniges et al. ("Dissolution behavior of different celluloses" *Biomacromolecules* 2011, 12, 871-879), hereby incorporated by reference in its entirety. Specifically, PWS-2 was dispersed in water, washed with ethanol, the solids dispersed in DMAc, and then left to solvent exchange overnight. The mixture was then filtered, the solids dispersed in 9% (w/v) LiCl/DMAc, and the mixture then placed on a laboratory shaker overnight for dissolution. After shaking overnight, the solution was diluted to a concentration of 0.9% (v/w) LiCl/DMAc and filtered through a 0.45 µm PTFE filter prior to GPC measurements.

The second sample, DSE-WL, is similar to the WL-1 sample from Example 1, except the DSE-WL is derived from digested steam exploded (DSE) material. DSE-WL was produced as follows. DSE material was first generated in a two-step process from ⅜" chips produced from a mixture of hardwood species. The first step in the process is the "digestion" portion, and the chips were mixed with water in a 6:1 water to dry solid ratio. That mixture was heated to about 180-205° C. at a pressure sufficient to keep the fluid in liquid form (generally less than about 240 psig) and held at that temperature for about 20-35 minutes in a horizontal screw digester. In the second step, the product from the first step was run through a steam mixing screw and horizontal screw digester, this time at a temperature of about 190-240° C. at a pressure of less than about 500 psig around for about 5-30 minutes residence time. The biomass was discharged through a blow line, causing the pressure to rapidly drop and the biomass to explode into smaller particles. The DSE material was used as the feed to a supercritical hydrolysis reactor. In that reactor, an aqueous slurry of DSE biomass was subjected to a temperature of about 350-400° C. for a period of less than about 10 sec under a pressure sufficient to keep the fluid in liquid or supercritical form (generally less than about 250 bar). The resulting mixture was then centrifuged in a disc centrifuge two times to obtain the DSE-WL sample.

GPC measurements were performed on instrumentation similar to that disclosed in Henniges et al. Specifically, the following components were used: online degasser, Dionex DG-2410; Kontron 420 pump, pulse damper; auto sampler, HP 1100; column oven, Gynkotek STH 585; multiple-angle (16-18) laser light scattering (MALLS) detector, Wyatt Dawn DSP with argon ion laser ($\lambda_0$=488 nm); fluorescence detector, Shimadzu RF 535 ($\lambda_{ex}$: 280 nm, $\lambda_{em}$: 312 nm); and refractive index (RI) detector, Shodex RI-71. Half of the MALLS detectors were equipped with interference filters (488±10 nm) that were used when appropriate. Data evaluation was performed with standard Astra, GRAMS/32, Chromeleon, and Origin software. The following parameters were used in the GPC measurements: flow: 1.00 mL/min; columns: four PL gel mixedA LS, 20 µm, 7.5×300 mm; injection volume: 100 µL; run time: 45 min; and N,N-dimethylacetamide/lithium chloride (0.9% v/w), filtered through a 0.02 µm filter, was used as the mobile phase. The amount of dissolved material was determined from the RI signal using a dn/dc of 0.136 mL/g and a detector constant of $5.3200\times10^{-5}$ $V^{-1}$.

Figure 14:
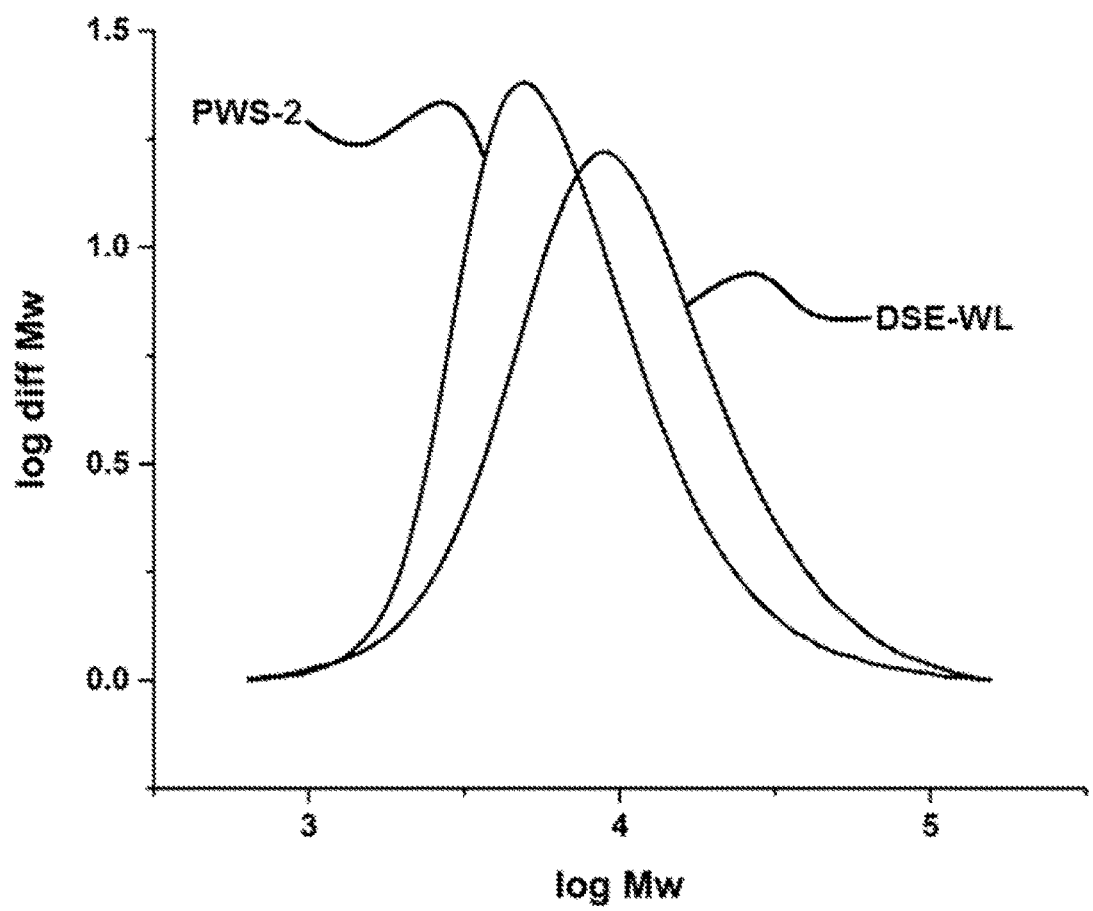
FIG. 14 shows the molar mass distribution of PWS-2 and DSE-WL samples (see examples).

The results of the GPC measurements are reported in Table 17 below, and the GPC trace is shown in FIG. 14.

TABLE 17

The molar mass distributions of cellulose in WL samples

| Sample | $\overline{Mw}$ (g/mol) | $\overline{Mn}$ (g/mol) | $\overline{Mz}$ (g/mol) | PDI | *DP |
|---|---|---|---|---|---|
| PWS-2 | 8,910 | 5,110 | 20,240 | 1.744 | 55 |
| DSE-WL | 13,790 | 7,160 | 27,680 | 1.924 | 85 |

*DP is calculated using Mw and is based on the anhydroglucose monomer (with MW = 162 g/mol; glucose-water)

Example 10

This example demonstrates the production and testing of various materials containing cellulose product and lignin for use with adhesive resins in the manufacture of engineered wood products (e.g., plywood).

Supercritical hydrolysis residue containing about 70 wt. % lignin and about 30 wt. % glucan (in which glucan is at least a portion of the cellulose product) was prepared as follows. Size-reduced biomass comprising hardwood was mixed with water to form a slurry. The slurry was reacted at a temperature of about 190-250° C. and a pressure of about 30-80 bar for a period of about 1 minute to about 20 minutes (termed "the HH process" for hemi-hydrolysis). After the reaction, the reaction mixture was then filtered using a filter press. The solids were collected and re-slurried with water. The liquids correspond to the xylo-oligosaccharide (XOS) stream.

The slurry was contacted with sub-critical, near-critical, or supercritical water having a temperature of about 340° C. to about 500° C. and a pressure of about 180 bar to about 350 bar (termed "the SH process" for supercritical hydrolysis), sufficient to bring the slurry to reaction conditions. The reaction mixture was maintained at a temperature of about 340° C. to about 420° C. for a residence time of about 0.1 sec to about 10 sec. The resulting reaction mixture was subjected to a filter press to obtain SH solids (SHR) and a liquid gluco-oligosaccharide (GOS) stream. SHR solids with different proportions of glucan and lignin can be prepared by varying the reaction conditions: generally higher temperature and/or longer residence time lead to higher lignin content (since more cellulose is hydrolyzed), and generally lower temperature and/or shorter residence times lead to lower lignin content (since more cellulose remains unhydrolyzed).

The compositional analysis of SHR-70 was performed according to the standard NREL protocol for biomass analysis (NREL/TP-510-42618, herein incorporated by reference in its entirety). The results are shown in Table 18. The sugars listed in Table 18 are xylan, glucan, arabinan, galactan, rhamnan, and mannan. The glucan content corresponds to a portion of the cellulose product.

TABLE 18

Compositional analysis of samples

| Sample | % Ash | % Xyl | % Glu | % Ara | % Gal | % Rha | % Man | Total sugar % | Total Lignin | Total |
|---|---|---|---|---|---|---|---|---|---|---|
| SHR-70 | 0.21 | 0.5 | 29.4 | 0.04 | 0.05 | 0.05 | 0.13 | 30.2 | 68.1 | 98.5 |

A commercial liquid PF resin (resol type) was sourced and used in combination with SHR-70 for Automatic Bond Evaluation System (ABES) tests. The ABES system is commercially available testing equipment from Adhesive Evaluation Systems, Inc. The commercial resin had a solids content of 44% (including about 8.5% NaOH) and a viscosity of about 750 cps at 25° C., suitable for softwood plywood manufacture.

To prepare SHR-70 for the ABES tests, the moisture content was first determined by the oven-drying method. SHR-70 in the solid form was ground into a fine powder and then mixed manually and thoroughly with a commercial liquid PF resin at a weight ratio of 45 wt. % on a dry solids basis.

Sliced maple veneers 117 mm×20 mm×0.8 mm (conditioned at 50% HR & 20 C) were used for the test. The mixture of SHR-70 and commercial PF resin was applied in a way to form bonding area of 20 mm×5 mm on the sliced maple veneers. A cure speed test was performed at 120° C. at selected press time points. Almost immediately after each bond was cured to the required level, the glued wood was tested to destruction in shear mode. Tensile load was monitored digitally during bond pulling and shear-stress-to-failure (area corrected peak load) was calculated. A control PF resin without any SHR-70 was also tested. Five replicates were performed for each sample. The results are shown in FIG. 15.

Figure 15:
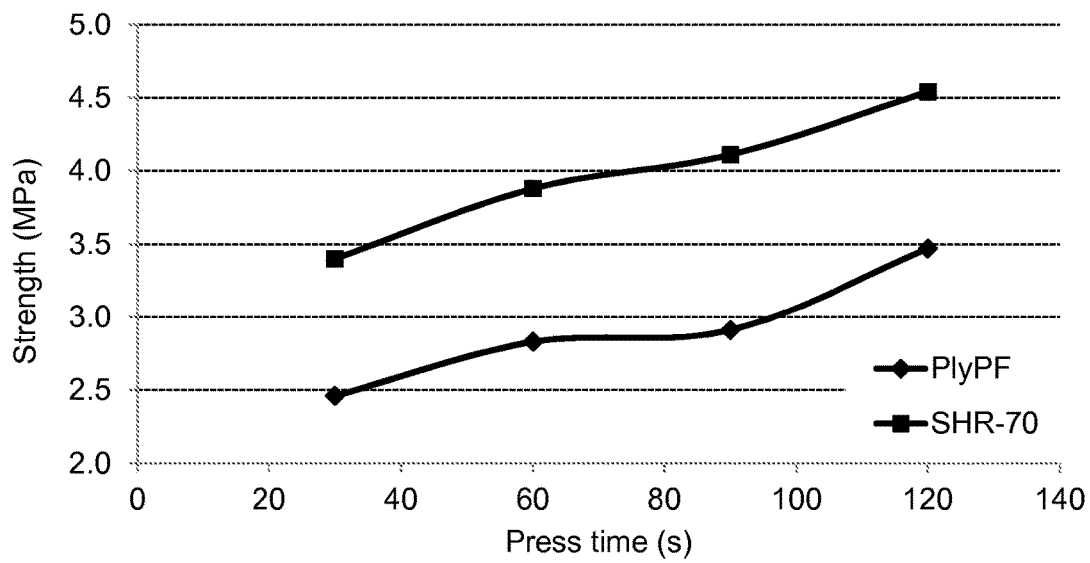
FIG. 15 shows the cure speed for various PF resin mixtures, in which a portion of the plywood PF resin has been substituted with a composition containing cellulose product (see Example 12).

FIG. 15 shows improved performance of a composition containing cellulose product versus commercial phenol-formaldehyde (PF) resin. Therefore, the carbohydrate component of the SHR (e.g., the cellulose product, having a crystalline character) may play a role in the performance of the compositions of the invention.

Example 11

This example demonstrates that the total combined yield of glucose monomer and oligomer can be increased by incorporating a recycling step. Material exiting the supercritical hydrolysis reactor is subjected to one or more separating steps, such as a squeeze press, a hydrocyclone, a centrifuge, gravity separation, or any combination thereof. The cellulosic solids are then recycled back to fresh feedstock that is fed to the supercritical hydrolysis reactor.

Yields can be calculated in at least two different ways in this example, shown by the "control volume" boxes 107 and 108 shown in FIG. 16. In control volume 1 (107), yield is calculated based on the amount of water-soluble glucose and glucose oligomer exiting the cooling step 104, relative to the total cellulose input to the supercritical hydrolysis reactor 103. In control volume 2, represented by box 108 in FIG. 16, yield is calculated based on total amount of water-soluble glucose and glucose oligomer in the liquids exiting separation step 105, relative to the total cellulose in feedstock 101 input to the system (i.e., input into control volume 2).

The supercritical hydrolysis process shown in FIG. 16 was performed in three different ways (Runs 1, 2, and 3).

Figure 17:
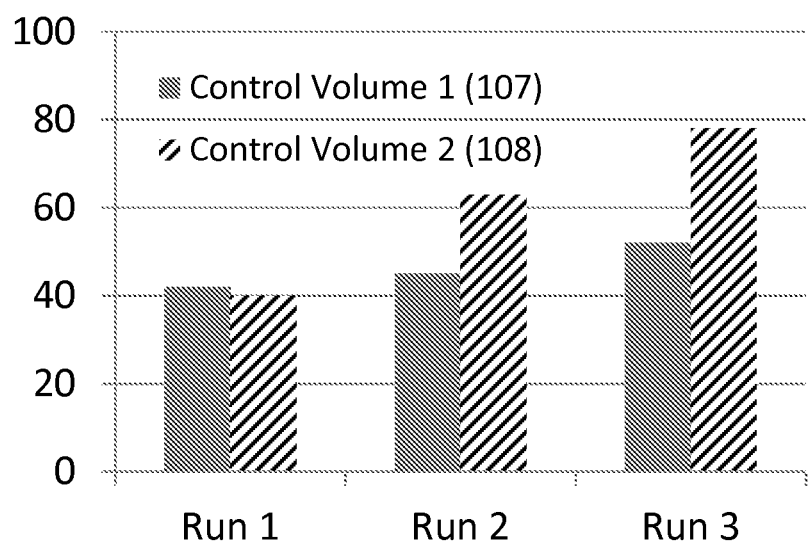
FIG. 17 shows different yields that can be calculated using different control volumes and with or without a recycle loop, as shown in FIG. 16 (also see examples).

The results of each Run are shown in FIG. 17. In Run 1, feedstock 101 was fed into feed tank 102, the feedstock was mixed with water to form a slurry in feed tank 102, the slurry was subjected to near-critical or supercritical conditions (103), the reaction mixture was cooled in cooling step 104, and a solid/liquid separation was performed in step 105. A recycle loop from separation step 105 to feed tank 102 was not employed in Run 1.

Run 2 is similar to Run 1, except Run 2 also employed a recycle loop, whereby the solids from separation step 105 were reslurried and fed to a second separation step 106 to separate cellulosic solids from the lignin solids, followed by feeding the separated cellulosic solids from second separation step 106 to feed tank 102. In feed tank 102, the cellulosic solids combine with fresh feedstock 101, and the hydrolysis process was repeated. It was on this repeat cycle that the yields were measured, rather than on the initial cycle of Run 2 (such that the recycled cellulosic solids figure in to the yield calculations).

Run 3 was similar to Run 2, except a more enhanced separation process was employed in separation step 106, such that even better separation of cellulosic solids from lignin was achieved than in Run 2, prior to combining the separated cellulosic solids with the fresh feedstock in feed tank 102. As in Run 2, the yield in Run 3 was calculated on the repeat cycle, rather than on the initial cycle that formed the recycled cellulosic solids (such that the recycled cellulosic solids figure in to the yield calculations).

As seen from the data in FIG. 17, the yields of both control volume 1 and 2 increase when the recycle loop is employed. The yield calculations for control volume 1 already account for the increased amount of cellulose in the feed tank during when the recycle loop is employed, such that the increase in yields cannot be attributed to simply re-running the cellulose output to further break it down. Without wishing to be bound by theory, it is hypothesized that running the cellulosic feedstock through the near-critical or supercritical hydrolysis process once makes the cellulose more susceptible to hydrolysis in a subsequent cycle, compared to the hydrolysis susceptibility of raw biomass. It is also clear that the recycled material can be largely converted to glucose and soluble oligomers, rather than over-converted to byproducts, because the yield for control volume 2 also increases significantly and is substantially due to the recycle loop.

Example 12

This example demonstrates the rheology modification properties of the cellulose product. A slurry of DSE material (prepared as described elsewhere herein) having a solids content of about 17.1 wt. % was pumped at a flow rate of about 1800 kg/hr at a temperature of about 40° C. Based on the measured pressure drop, a viscosity of about 3680 cP was calculated. A similar slurry of DSE material was also prepared, except cellulose product was added in an amount of about 35 wt. % based on the total weight of the slurry on a dry basis. The total solids content of the slurry, however, was increased to about 19.5 wt. %. The flow rate was measured for this higher solids content slurry (which includes cellulose product) to be about 1800 kg/hr at about 40° C., but the viscosity calculated from the measured pressure drop was only about 3660 cP.

As this example demonstrate, the addition of cellulose product to a slurry of DSE material allowed the solids content of the DSE slurry to be increased by about 2.4% while achieving a comparable viscosity. A fit to previously measured DSE samples suggests that the viscosity and pressure drop more than double when the solids content of a slurry of DSE material (without any cellulose product) is increased from about 17.1 wt. % to 19.5 wt. %. However, as shown in this example, a slight decrease in viscosity was observed, demonstrating that the addition of cellulose product tempers the negative effects of increasing slurry solids content.

Example 13

This example relates to analysis of the cellulose present in WL samples derived from digested steam exploded (DSE) material. The two DSE samples (DSE-WL-2 and DSE-WL-3) were prepared similarly to the DSE-WL sample of Example 9, except instead of using a disc centrifuge after the supercritical hydrolysis reactor, the solids were instead separated from the liquids by filtration, followed by extra gravity separation and washing steps.

The solids obtained from the supercritical hydrolysis reactor (Example 9) were subjected to filtration, followed by separation using a series of three hydrocyclones to obtain a purer crop of cellulosic solids. The overs of each hydrocyclone comprise the cellulosic solids, and the overs of the first hydrocyclone were sent to the second hydrocyclone, and the overs from this second hydrocyclone were sent to a third hydrocyclone. The overs from this third hydrocyclone were filtered and the resulting solids (cellulose) were then extracted with methanol for 24 h at 40° C. at 1:50 solids to liquid ratio (S:L), followed by 0.1 M NaOH extraction for 48 h at the same temperature at 1:60 S:L ratio. Between the extraction steps, the solids were separated from the solvent used in the extraction and washed with the same solvent. The washing solvents were combined with the separation effluents and dried until no weight-change was observed in a 50° C. oven, indicating that all extractables were removed from the solids with the given extraction solvent. In the 0.1 M NaOH extraction, prior to drying, the effluents were acidified to pH 3, and the solids were separated and washed with water to remove salts. The solid residue after methanol and NaOH extractions was neutralized (pH 7) and washed 3 times at 1:200 S:L before drying. Two samples were prepared with this procedure, DSE-WL-2 and DSE-WL-3. These cellulose-rich samples were subsequently analyzed by GPC.

The DSE-WL-2 and DSE-WL-3 samples, as well as a comparative sample of commercially obtained microcrystalline cellulose ("MCC"—Acros Organics, cellulose microcrystalline, extra pure, average particle size 90 μm, product #382310010), were activated/solubilized according to the "first condition": (i) swelling the cellulose product twice in DI water for 1 hour each while stirring at room temperature (filter and re-suspend solids in fresh DI water after each swelling), (ii) activating the resulting solids twice in methanol for 45 minutes each at room temperature while stirring (filter and re-suspend solids in fresh methanol after each activating), (iii) activating the resulting solids in N,N-Dimethylacetamide (DMAc) (without LiCl) overnight at room temperature with stirring (followed by filtration of solids), (iv) stirring the resulting solids in 8% by weight LiCl in DMAc for 24 hours at room temperature, followed by (v) subjecting the same LiCl/DMAc mixture (without any filtration) at 2-8° C. for up to 3 days without stirring. All of the steps of the first condition are performed at ambient pressure. Over 80 wt. % of the DSE cellulosic solids were solubilized when subjected to the first condition, whereas all of the MCC was solubilized.

The solutions at 8% by weight LiCl in DMAc were diluted to a concentration of 0.8 wt. % LiCl in DMAc and analyzed on a Viscotek GPCMax equipped with LT6000L columns and the TDA 305 detector array, with LALLS, RALLS, RI and Intrinsic Viscosity detectors. The eluent was the same as the sample solvent and the elution speed was kept at 1.0 ml/min. Standards were 65k and 95 k Da PMMA standards from Malvern. The software for MMD calculations was the OmniSEC program (ver. 4.7) and all samples were prepared in the ~2-5 mg/ml concentration range. The average dn/dc was calculated to be 0.1577 ml/g with 0.0017 ml/g standard deviation, such that the 0.1577 value was used as the dn/dc in this example.

Measurements were performed in triplicate and the resulting values averaged. Most of the values were calculated and reported by the GPC instrument software. The viscosity average molecular weights ($M_v$) were calculated according to Sasaaki et al. ("Kinetics of cellulose conversion at 25 MPa in sub- and supercritical water." AIChE J., 50(1), 192 (2004)), hereby incorporated by reference in its entirety, using the intrinsic viscosity (IV) and Mark-Houwink constants (a and K) measured by GPC in this example (see Table 19). The results (triplicate averages) are shown below in Table 19.

TABLE 19

Comparison of MCC and DSE-derived cellulosic samples

|  | MCC | DSE-WL-2 | DSE-WL-3 |
|---|---|---|---|
| $M_n$ - (Daltons) | 10529 | 3944 | 4077 |
| $M_w$ - (Daltons) | 43046 | 5452 | 5977 |
| $M_z$ - (Daltons) | 163316 | 10694 | 15456 |
| $M_p$ - (Daltons) | 31957 | 3009 | 3084 |
| $M_w/M_n$ (PD) | 4.14 | 1.38 | 1.46 |
| $DP_w$ | 266 | 34 | 37 |
| $R_h(w)$ - (nm) | 9.5 | 2.4 | 2.5 |
| a | 0.638 | 0.373 | 0.403 |
| logK | −2.598 | −2.148 | −2.254 |
| IV - (dl/g) | 1.793 | 0.176 | 0.184 |
| $M_v$ - (Daltons) | 29307 | 5581 | 6027 |
| dn/dc - (ml/g) | 0.1577 | 0.1577 | 0.1577 |

$DP_w$: degree of polymerization (DP) calculated from $M_w$ using the anhydroglucose molar weight (162 g/mol)
$R_h(w)$: the hydrodynamic radius calculated from $M_w$ in nanometers
a and K: Mark-Houwink constants calculated using the intrinsic viscosity (IV) relationship with $M_w$, Malvern OmniSEC software (ver. 4.7)
$M_v$: viscosity average molecular weight calculated from IV and the Mark-Houwink constants as detailed herein Notably, the molecular weights of the DSE-WL samples in this example, which employed digested steam exploded starting material, are lower than the molecular weights of WL samples in previous examples, which employed comminuted wood. The molecular weight values, and other properties, described herein apply to either materials derived from comminuted biomass, digested steam exploded biomass, or both, as will be clear from context.

The dn/dc values shown in Table 19, which were calculated by the GPC instrument in this analysis, appeared to be somewhat higher than typical values (which generally are in the range of about 0.135 ml/g to 0.145 ml/g in <1 wt. % LiCl in DMAc solvent systems). As a result, using known dn/dcs of 0.147 ml/g (for 0.5 wt. % LiCl in DMAc) and 0.136 ml/g (for 0.9 wt. % LiCl in DMAc), a dn/dc of 0.139 ml/g was calculated for this example using a literature method (Potthast et al., *Cellulose*, "Comparison testing of methods for gel permeation chromatography of cellulose: coming closer to a standard protocol," DOI 10.1007/s10570-015-0586-2, published online Mar. 13, 2015, hereby incorporated by reference in its entirety). The parameters for this example were recalculated using this new dn/dc value of 0.139 ml/g, and the results are set forth in Table 20 below. The footnotes of Table 19 also apply to Table 20.

TABLE 20

Parameters of Table 19 recalculated using a dn/dc of 0.139 ml/g

|  | MCC | DSE-WL-2 | DSE-WL-3 |
|---|---|---|---|
| $M_n$ - (Daltons) | 13561 | 6743 | 6144 |
| $M_w$ - (Daltons) | 56259 | 9283 | 9493 |
| $M_z$ - (Daltons) | 221285 | 18046 | 26072 |
| $M_p$ - (Daltons) | 41298 | 5151 | 4587 |
| $M_w/M_n$ (PD) | 4.20 | 1.37 | 1.54 |
| $DP_w$ | 347 | 57 | 59 |
| $R_h(w)$ - (nm) | 10.39 | 3.12 | 2.98 |
| a | 0.634 | 0.358 | 0.385 |
| logK | −2.646 | −2.057 | −2.184 |
| IV - (dl/g) | 1.793 | 0.235 | 0.213 |
| $M_v$ - (Daltons) | 37714 | 9754 | 8421 |
| dn/dc - (ml/g) | 0.139 | 0.139 | 0.139 |

While the absolute values of the various parameters change when comparing Tables 19 and 20, it is important to note that the trend is the same. MCC has a higher molecular weight and a higher DP than the two DSE-WL samples.

Example 14

This example demonstrates the measurement of carbonyl content (CO) and molecular weights for cellulose product using a combination of fluorescence labeling and GPC. The HHR, SHR-50, and SHR-80 samples of Example 5, prior to any extraction or washing, were used in this example. In addition, DSE material similar to that produced in Example 9 was employed (prior to subjecting to the supercritical hydrolysis reactor). Moreover, the material similar to that in Example 9 remaining after subjecting the DSE material to the supercritical hydrolysis reactor also was employed in this example, except instead of using a disc centrifuge on the material exiting the supercritical hydrolysis reactor, the solids were simply filtered from the liquids to obtain the solids (DSE-SHR). In other words, the samples used in this example are the total solids remaining after the indicated reaction process, without any fractionation of the solids (e.g., into higher and lower molecular weight fractions, which may sometimes be achieved used gravity separation techniques). As such, the measurements herein are performed on the full (unfractionated) cellulose in the sample. Previous examples herein utilize some sort of gravity separation (e.g., centrifugation or hydrocyclones), and thus represent fractionated cellulose samples.

Each of these samples was exhaustively washed with water to remove residual water soluble matter and exhaustively extracted with 80% (volume/volume) aqueous dioxane at room temperature. The solids remaining after extraction were subjected to a sodium chlorite extraction as follows: 1 g of solids was mixed with 200 mL of 0.2 M sodium chlorite solution. This mixture was combined with 200 mL of 0.2 M sodium acetate buffer (pH of 5). The resulting mixture was agitated by shaking for 48 hours. After 48 hours, the solids were filtered and then washed with water and ethanol. This chlorite extraction was repeated once to remove impurities and obtain pure cellulose. The obtained cellulose (designated in the table below by "-x") was prepared for analysis by using the second condition (described elsewhere herein) and the prepared sample measured for CO content and molecular weight by GPC according to Röhrling et al. "A Novel Method for the Determination of Carbonyl Groups in Cellulosics by Fluorescence Labeling. 2. Validation and Applications," (*Biomacromolecules* (2002) 3, 969-975), hereby incorporated by reference in its entirety. The results are shown below in Table 21.

TABLE 21

Carbonyl contents and molecular weights of various pure cellulose samples produced herein.

|  | $M_w$ (kg/mol) | $M_n$ (kg/mol) | $M_z$ (kg/mol) | PDI (kg/mol) | CO (μmol/g) |
|---|---|---|---|---|---|
| DSE-x | 418 | 98.2 | 1330 | 4.3 | 36.9 |
| HHR-x | 368.2 | 86.3 | 1129 | 4.3 | 50.7 |
| SHR-50-x | 28.7 | 20.2 | 43.8 | 1.4 | 97.3 |
| SHR-80-x | 96.5 | 51.5 | 253.7 | 1.9 | 219.1 |
| DSE-SHR-x | 12.1 | 4.5 | 77.3 | 2.7 | 211.4 |

While the preferred forms of the invention have been disclosed, it will be apparent to those skilled in the art that various changes and modifications may be made that will achieve some of the advantages of the invention without departing from the spirit and scope of the invention. Therefore, the scope of the invention is to be determined solely by the claims to be appended.

When ranges are used herein for physical properties, such as temperature ranges and pressure ranges, or chemical properties, such as chemical formulae, all combinations, and sub-combinations of ranges specific embodiments therein are intended to be included.

The disclosures of each patent, patent application, and publication cited or described in this document are hereby incorporated herein by reference, in their entirety.

Those skilled in the art will appreciate that numerous changes and modifications may be made to the preferred embodiments of the invention and that such changes and modifications may be made without departing from the spirit of the invention. It is, therefore, intended that the appended claims cover all such equivalent variations as fall within the true spirit and scope of the invention.

What is claimed:

1. A method comprising:
    providing a feedstock comprising a type-I cellulose;
    converting at least a portion of the type-I cellulose by contacting the feedstock with a fluid comprising a near critical or a supercritical water at a temperature above about 300° C. to form a cellulose product comprising a type-II cellulose; and
    hydrolyzing at least a portion of the type-II cellulose to form a hydrolyzed cellulose product.

2. The method of claim 1, wherein the cellulose product comprises an unconverted type-I cellulose and the type-II cellulose.

3. The method of claim 2, wherein at least one of conditions (1) and (2) is satisfied:

(1) the cellulose product comprises cellulose having a weight-average molecular weight of about 3,000 g/mol to about 25,000 g/mol as determined on a sample of the cellulose product that has been prepared for gel-permeation chromatography analysis according to a first condition; and (2) cellulose in the cellulose product has a carbonyl content of at least about 60 µmol/g, as determined on a sample of the cellulose product that has been prepared for gel-permeation chromatography analysis according to a second condition.

4. The method of claim 2, wherein the composition further comprises lignin.

5. The method of claim 2, wherein the cellulose product has a weight-average molecular weight that is less than about 0.5 times the weight-average molecular weight of microcrystalline cellulose.

6. The method of claim 2, further comprising separating the lignin from the cellulose product using a hydrocyclone; wherein at least a portion of the lignin is removed in an underflow of the hydrocyclone and at least a portion of the cellulose product is removed in an overflow of the hydrocyclone.

7. The method of claim 1, wherein the hydrolyzing is carried out at a lower temperature than the converting.

8. The method of claim 1, wherein the hydrolyzing comprises employing a fluid comprising hot compressed water.

9. The method of claim 1, wherein the hydrolyzing is carried out using thermal energy originating from the converting.

10. The method of claim 1, wherein the converting is conducted at a temperature above 100° C., and the type-II cellulose produced in the converting is maintained at a temperature above 100° C. prior to the hydrolyzing, and optionally during the hydrolyzing.

11. The method of claim 1, wherein the converting produces a stream at a first temperature, and the method further comprises:
lowering the first temperature of the stream to a second temperature;
maintaining the stream at the second temperature for a period of time, and changing the stream to a third temperature prior to the hydrolyzing;
wherein the hydrolyzing is conducted at a fourth temperature that is the same as or different from the third temperature.

12. The method of claim 1, wherein the hydrolyzing comprises acid hydrolysis.

13. The method of claim 2, further comprising hydrolyzing the type-II cellulose, wherein the type-II cellulose is selectively hydrolyzed over the unconverted type-I cellulose.

14. The method of claim 2, further comprising recovering the unconverted type-I cellulose.

15. The method of claim 1, wherein the cellulose product acts as a rheology modifier.

16. The method of claim 2, further comprising employing at least a portion of the cellulose product as at least a portion of the feedstock, and repeating the method at least one time.

17. The method of claim 1, wherein at least a portion of the feedstock is fractionated biomass.

18. The method of claim 1, further comprising incorporating the hydrolyzed cellulose product into an adhesive selected from the group consisting of a phenolic resin, a phenol-formaldehyde resin, or a combination thereof.

19. A method comprising:
providing a feedstock comprising a type-I cellulose;
converting at least a portion of the type-I cellulose by contacting the feedstock with a fluid comprising a sub-critical, near-critical, or a supercritical water to form a composition comprising a cellulose product, wherein the cellulose product comprises unconverted type-I cellulose and a type-II cellulose, and
hydrolyzing, in a different step from the converting, at least a portion of the unconverted type-I cellulose at the same or different conditions as the converting.

20. A method comprising:
providing a feedstock comprising a type-I cellulose;
converting at least a portion of the type-I cellulose to a type-II cellulose; and
hydrolyzing at least a portion of the type-II cellulose;
wherein the converting produces a composition comprising a cellulose product, wherein the cellulose product comprises an unconverted type-I cellulose and the type-II cellulose; and wherein the uncoverted type-I cellulose is recovered.

* * * * *